United States Patent
Geiger et al.

(10) Patent No.: US 11,167,015 B2
(45) Date of Patent: Nov. 9, 2021

(54) ARGININE AND ITS USE AS A T CELL MODULATOR

(71) Applicant: INSTITUTE FOR RESEARCH IN BIOMEDICINE, Bellinzona (CH)

(72) Inventors: Roger Geiger, Bellinzona (CH); Antonio Lanzavecchia, Porza (CH); Federica Sallusto, Porza (CH)

(73) Assignee: INSTITUTE FOR RESEARCH IN BIOMEDICINE, Bellinzona (CH)

(*) Notice: Subject to any disclaimer, the term of this patent is extended or adjusted under 35 U.S.C. 154(b) by 236 days.

(21) Appl. No.: 16/340,337

(22) PCT Filed: Oct. 12, 2017

(86) PCT No.: PCT/EP2017/076123
§ 371 (c)(1),
(2) Date: Apr. 8, 2019

(87) PCT Pub. No.: WO2018/069471
PCT Pub. Date: Apr. 19, 2018

(65) Prior Publication Data
US 2019/0307856 A1 Oct. 10, 2019

(30) Foreign Application Priority Data
Oct. 12, 2016 (EP) .................................. 16193598

(51) Int. Cl.
| | | |
|---|---|---|
| A61K 31/164 | (2006.01) |
| A61K 38/43 | (2006.01) |
| A61P 35/00 | (2006.01) |
| A61K 31/198 | (2006.01) |
| A61K 35/17 | (2015.01) |
| A61K 38/17 | (2006.01) |
| A61K 38/18 | (2006.01) |
| C07K 14/47 | (2006.01) |
| A61P 31/00 | (2006.01) |
| A61K 31/00 | (2006.01) |

(Continued)

(52) U.S. Cl.
CPC .............. *A61K 38/43* (2013.01); *A61K 31/00* (2013.01); *A61K 31/198* (2013.01); *A61K 35/17* (2013.01); *A61K 38/1709* (2013.01); *A61K 38/18* (2013.01); *A61K 48/005* (2013.01); *A61P 31/00* (2018.01); *A61P 31/02* (2018.01); *A61P 35/00* (2018.01); *C07K 14/4702* (2013.01)

(58) Field of Classification Search
CPC .................................................... A61K 31/164
See application file for complete search history.

(56) References Cited

FOREIGN PATENT DOCUMENTS

| WO | 2012019127 A2 | 2/2012 | |
|---|---|---|---|
| WO | WO-2012019127 A2 * | 2/2012 | ........... A61K 31/198 |

OTHER PUBLICATIONS

Munder M. et al., "L-Arginine deprivation impairs Leishmania Major-specific T-cell responses," Eur. J. of Immunology, 2009, 39(8): 2161-2172.

(Continued)

*Primary Examiner* — Rosanne Kosson
(74) *Attorney, Agent, or Firm* — Harness Dickey & Pierce P.L.C.

(57) ABSTRACT

The present invention provides novel uses and methods for T cell based immunotherapies. Specifically, the invention relates to novel ligands, targets and nucleic acids and vectors encoding said targets that are useful for modulating T cell responses.

10 Claims, 31 Drawing Sheets

Specification includes a Sequence Listing.

(51) Int. Cl.
   *A61P 31/02*  (2006.01)
   *A61K 48/00*  (2006.01)

(56) References Cited

OTHER PUBLICATIONS

Narita Y. et al., "The Key Role of IL-6-Arginase Cascade for Inducing Dendritic Cell-Dependent CD4+ T Cell Dysfunction in Tumor-Bearing Mice," The Journal of Immunology, 2012, 190(2): 812-820.
French J.D. et al., "Germline polymorphisms in an enhancer of PSIP1 are associated with progression-free survival in epithelial ovarian cancer," Impact Journals, 2016, 7(6): 6353-6368.
Fadel H.J. et al., "TALEN Knockout of PSIP1 Gene in Human Cells: Analyses of HIV-1 Replication and Allosteric Integrase Inhibitor Mechanism," Journal of Virology, 2014, 88(17): 9704-9717.
Meng J. et al., "WSTF promotes proliferation and invasion of lung cancer cells by inducing EMT via PI3K/Akt and IL-6/STAT3 signaling pathways," Cellular Signalling, 2016, 28(11): 1673-1682.
International Search Report and Written Opinion for PCT Application No. PCT/EP2017/076123 dated Jan. 22, 2018.

\* cited by examiner

Figure 1:
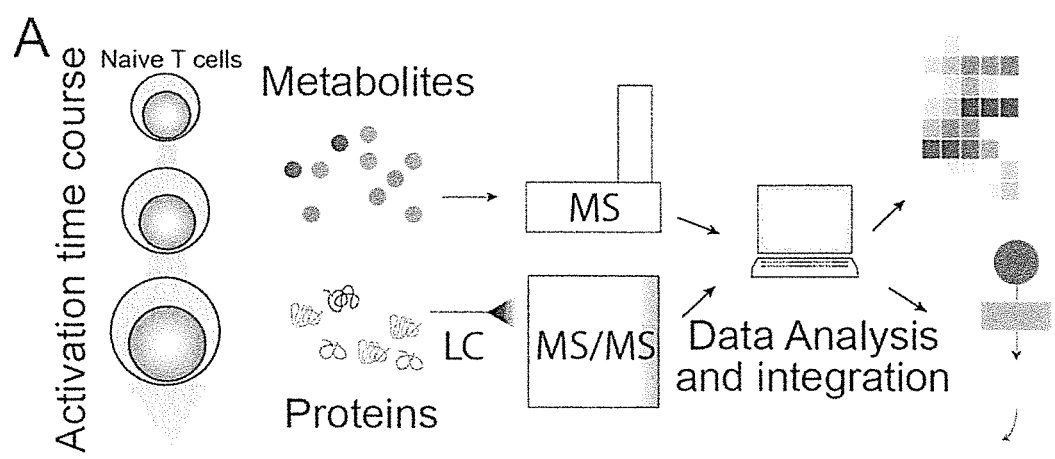

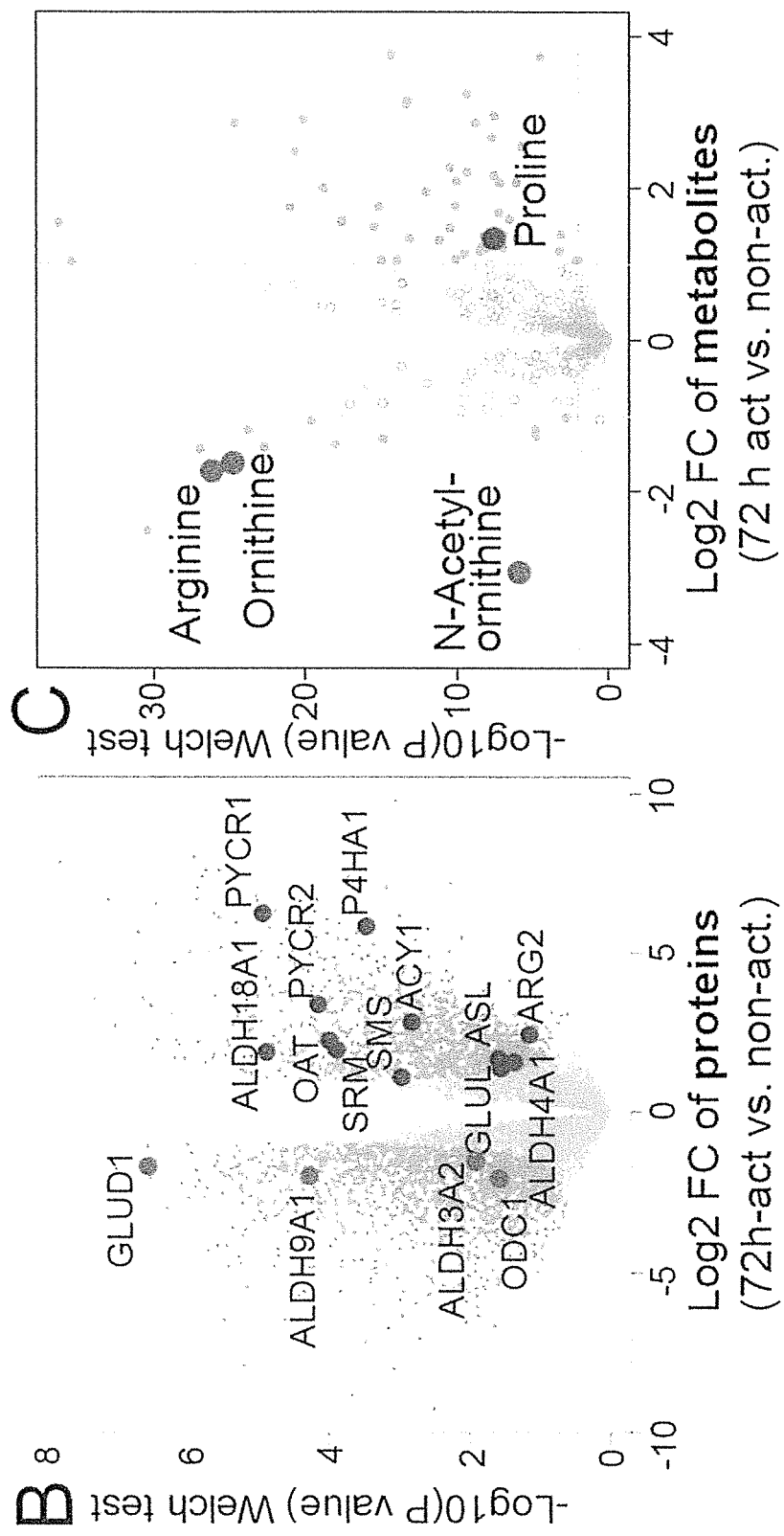
Figure 1 (c'td)

Figure 2:
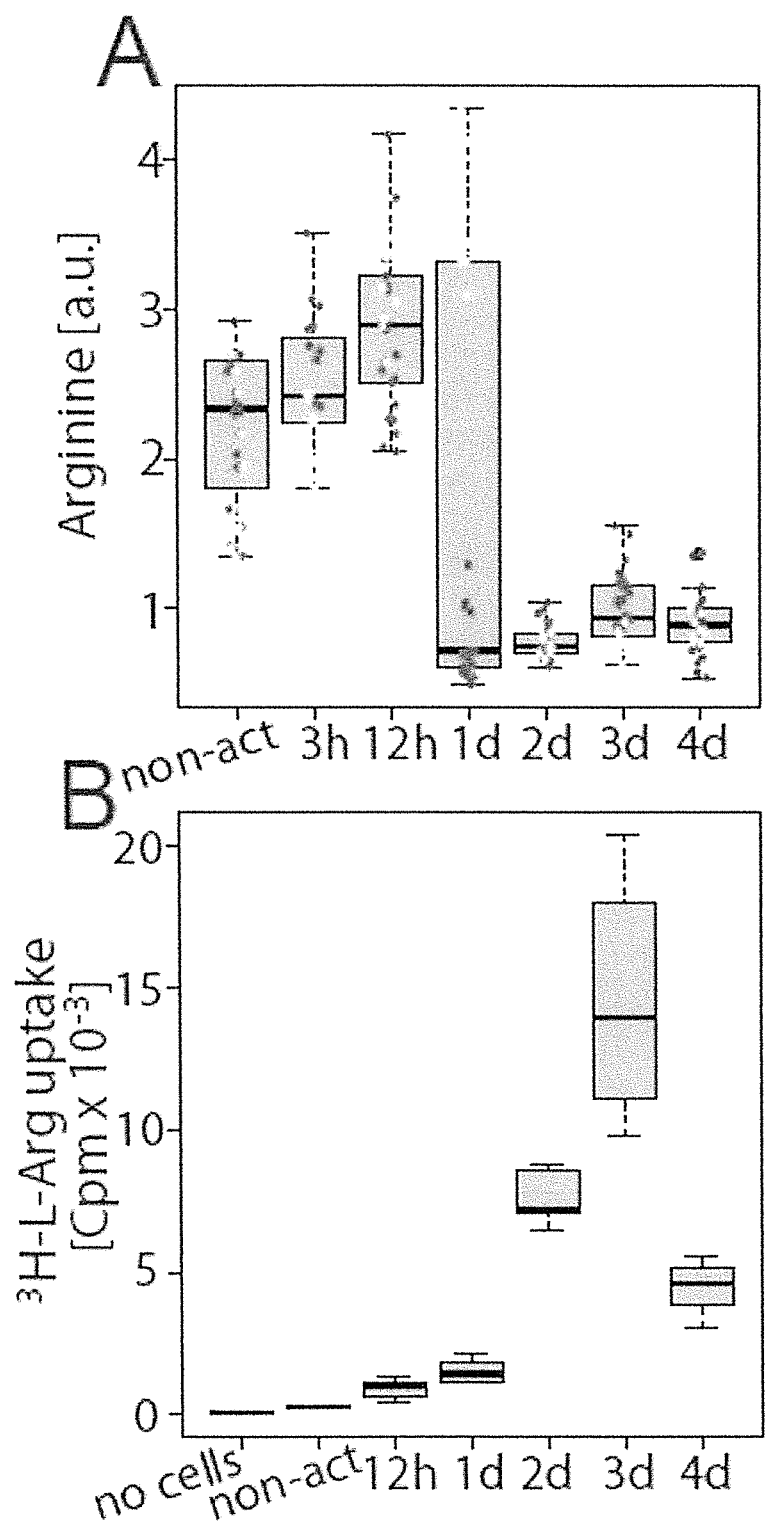

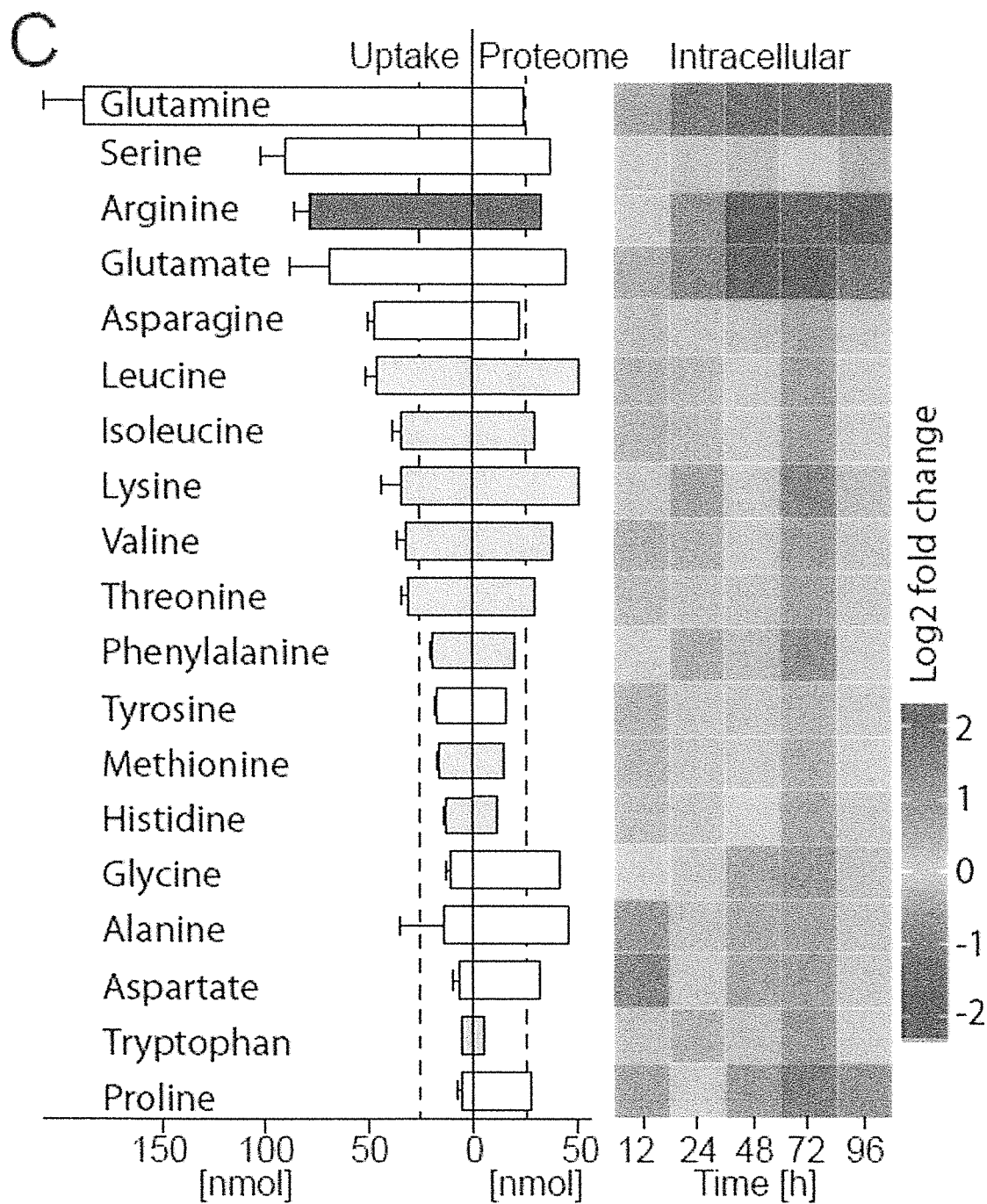
Figure 2 (c'td)

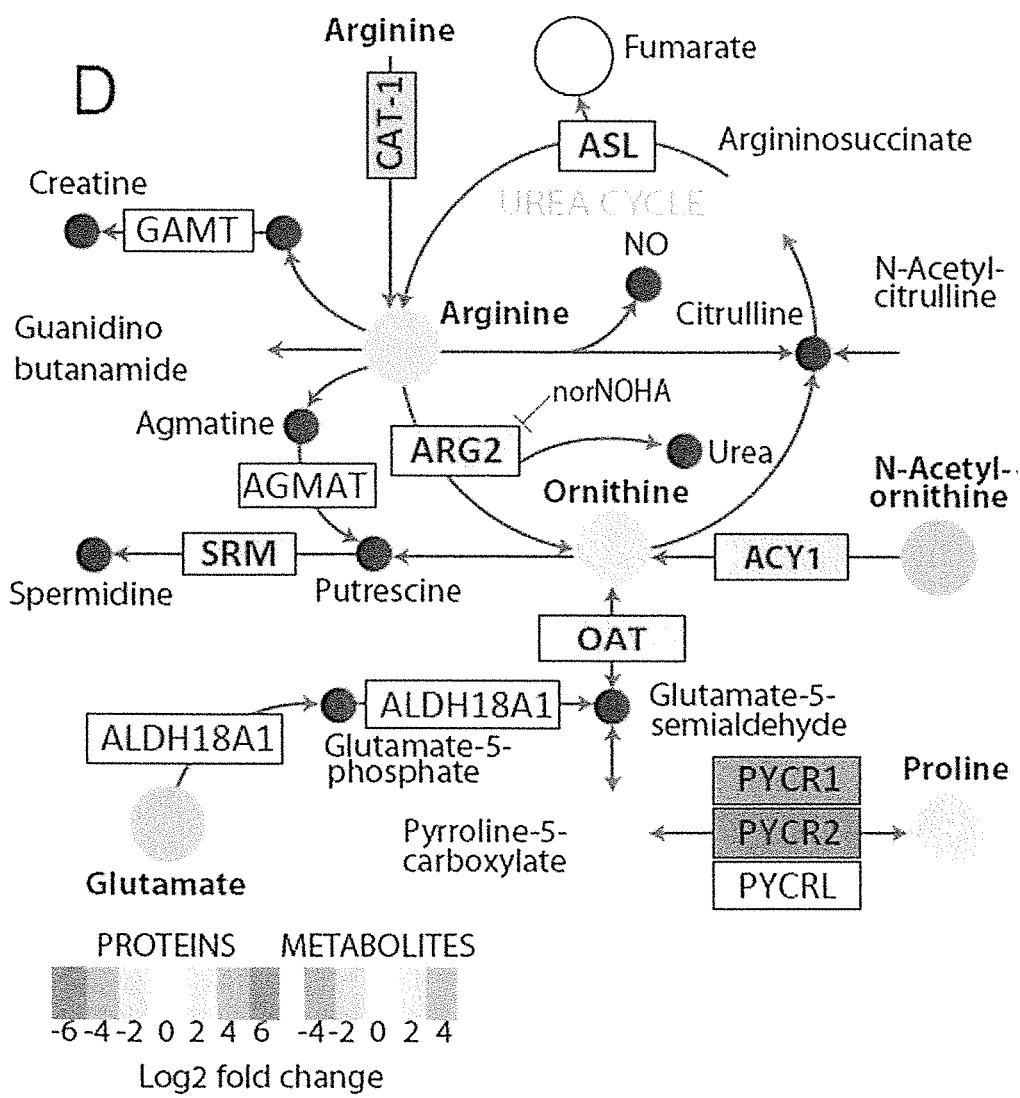
Figure 2 (c'td)

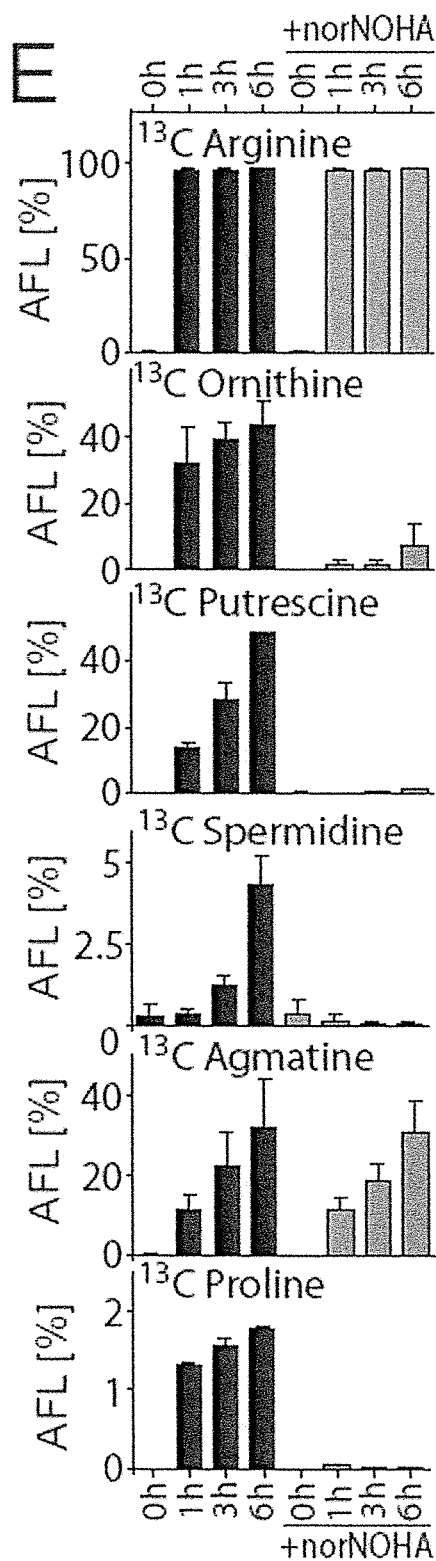
Figure 2 (c'td)

Figure 3:
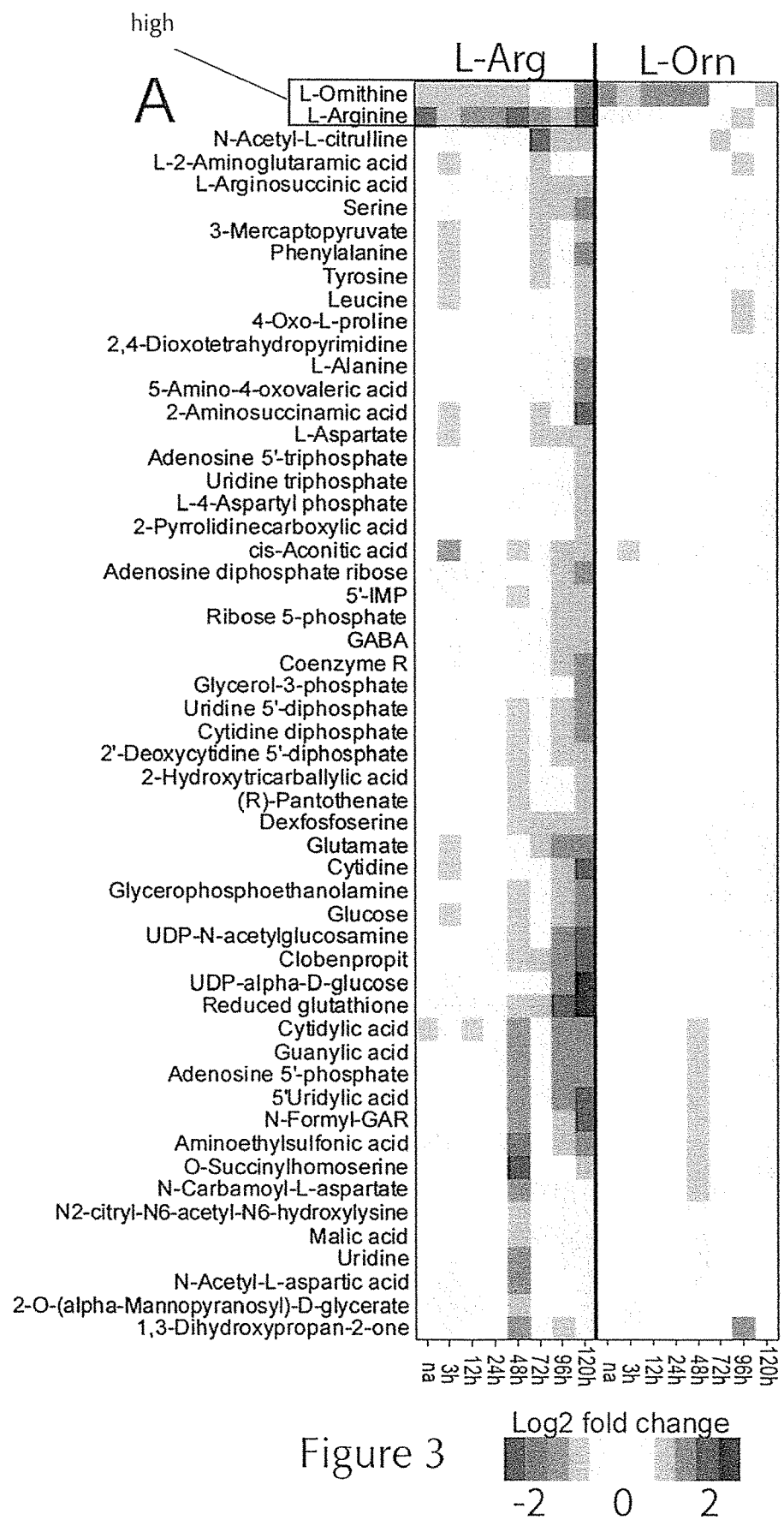

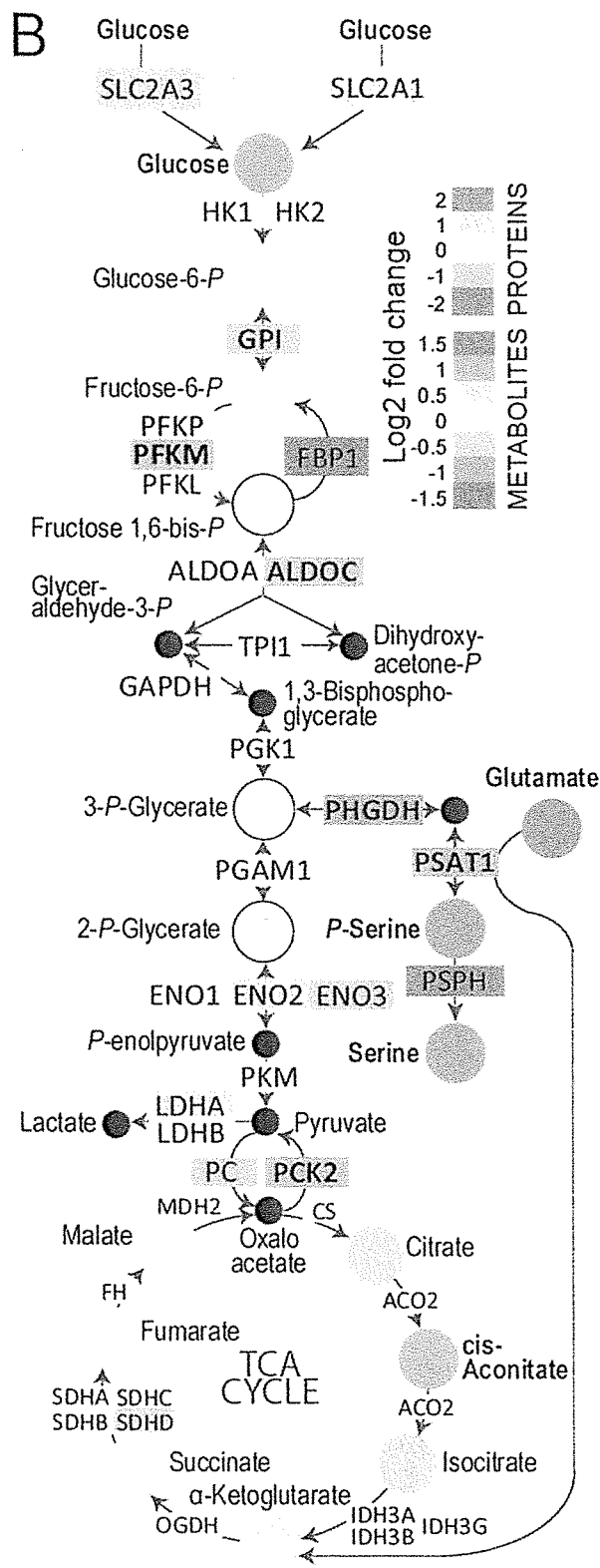
Figure 3 (c'td)

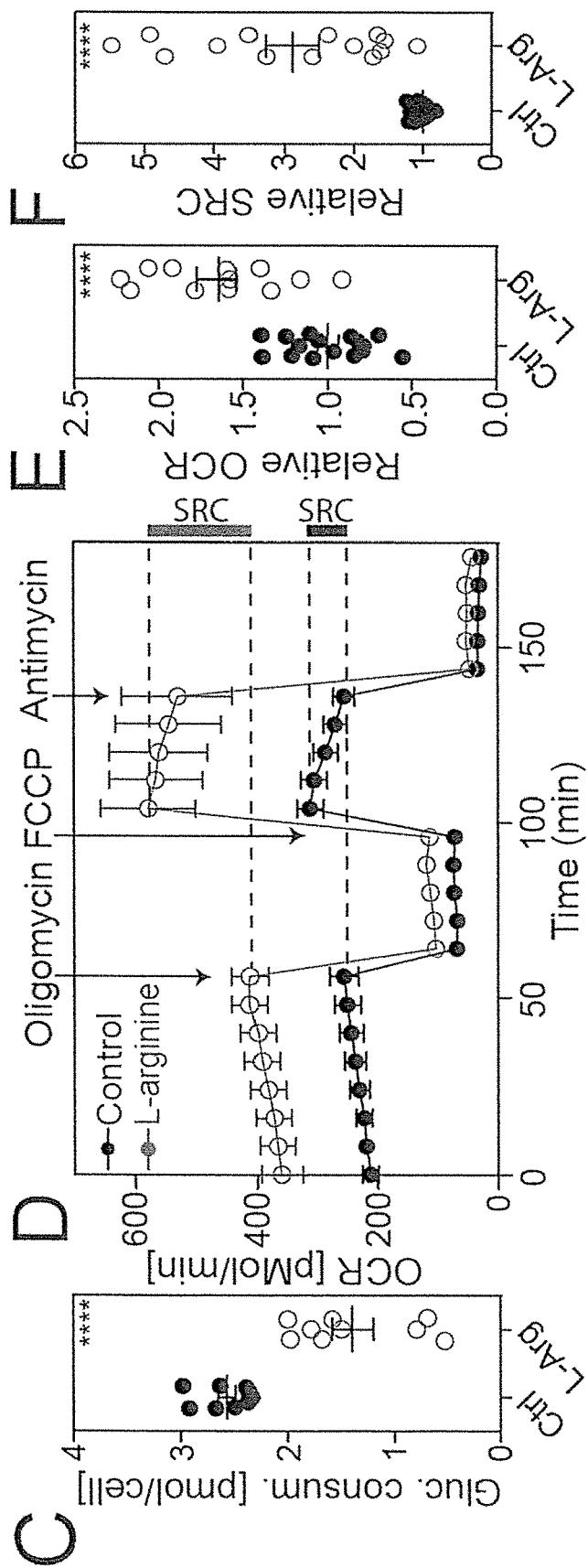
Figure 3 (c'td)

Figure 4:
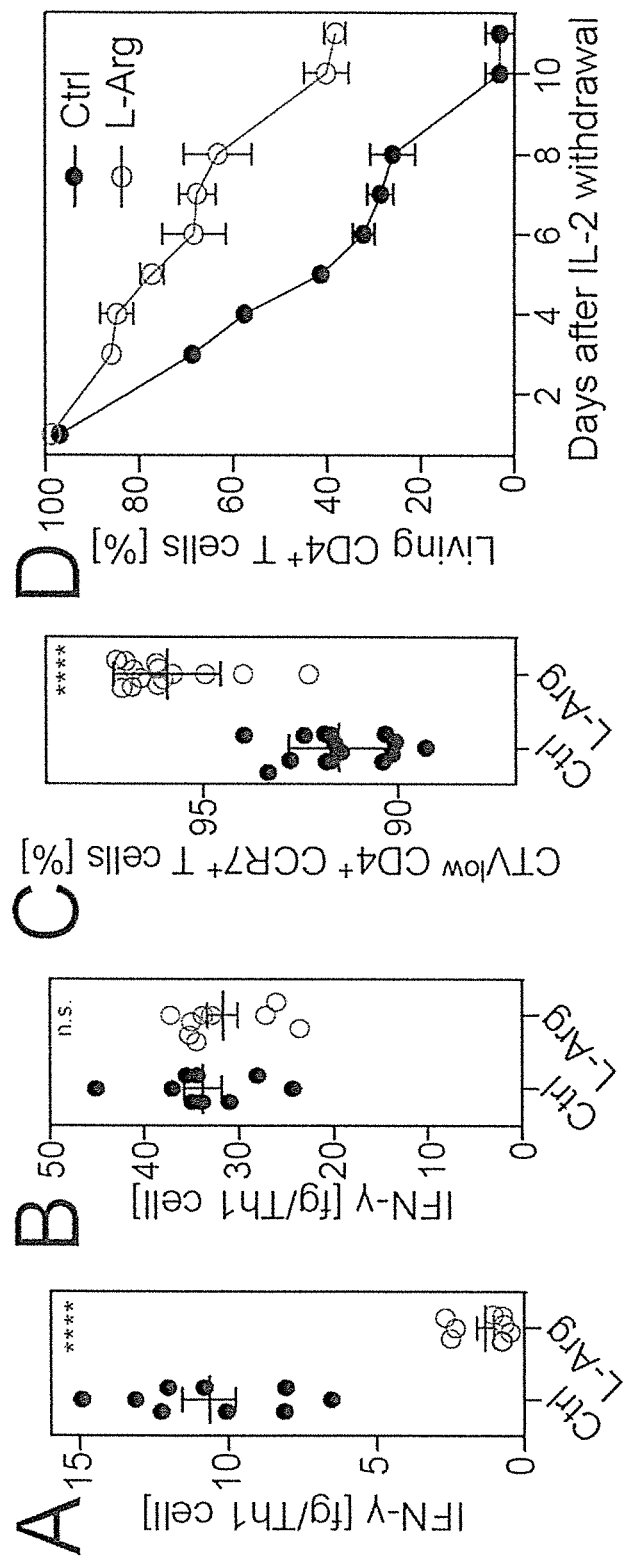

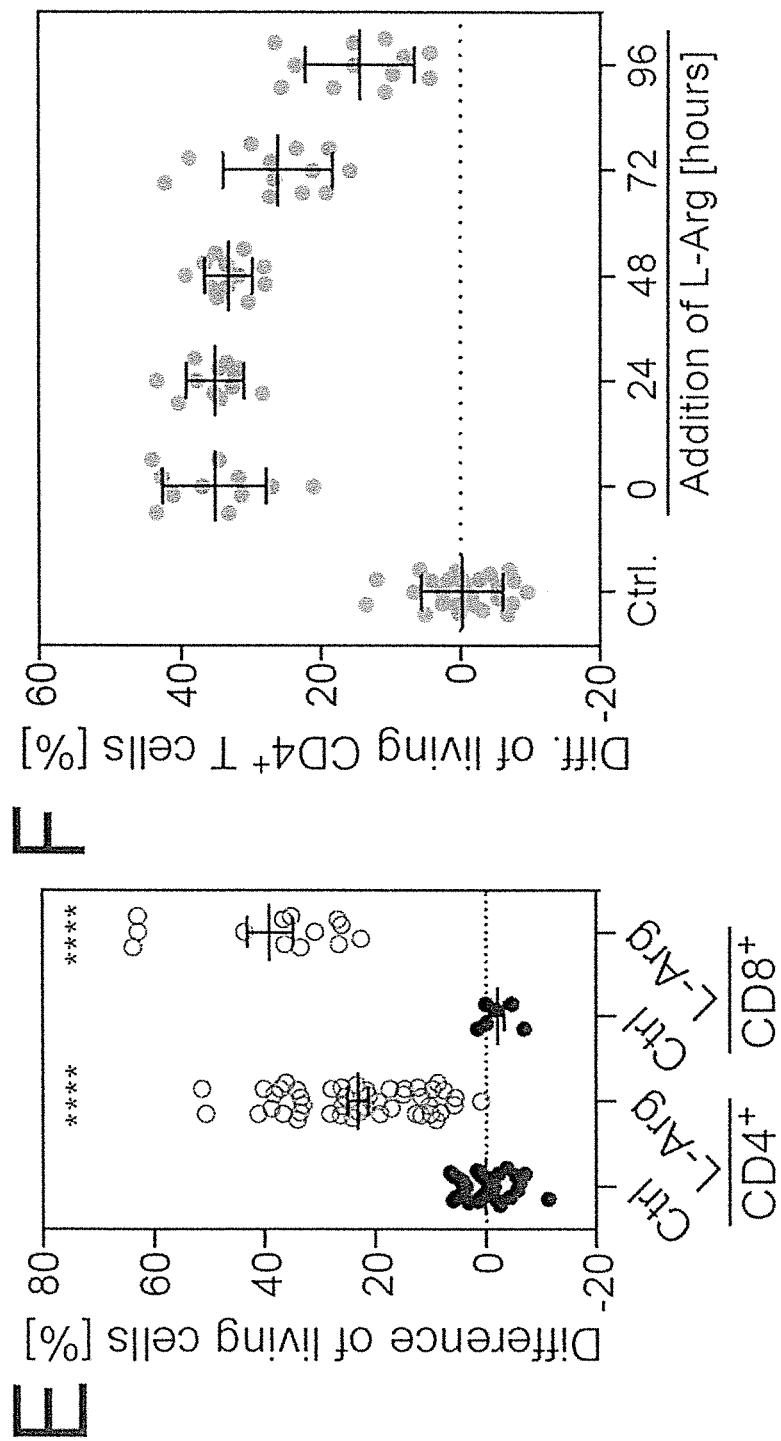
Figure 4 (c'td)

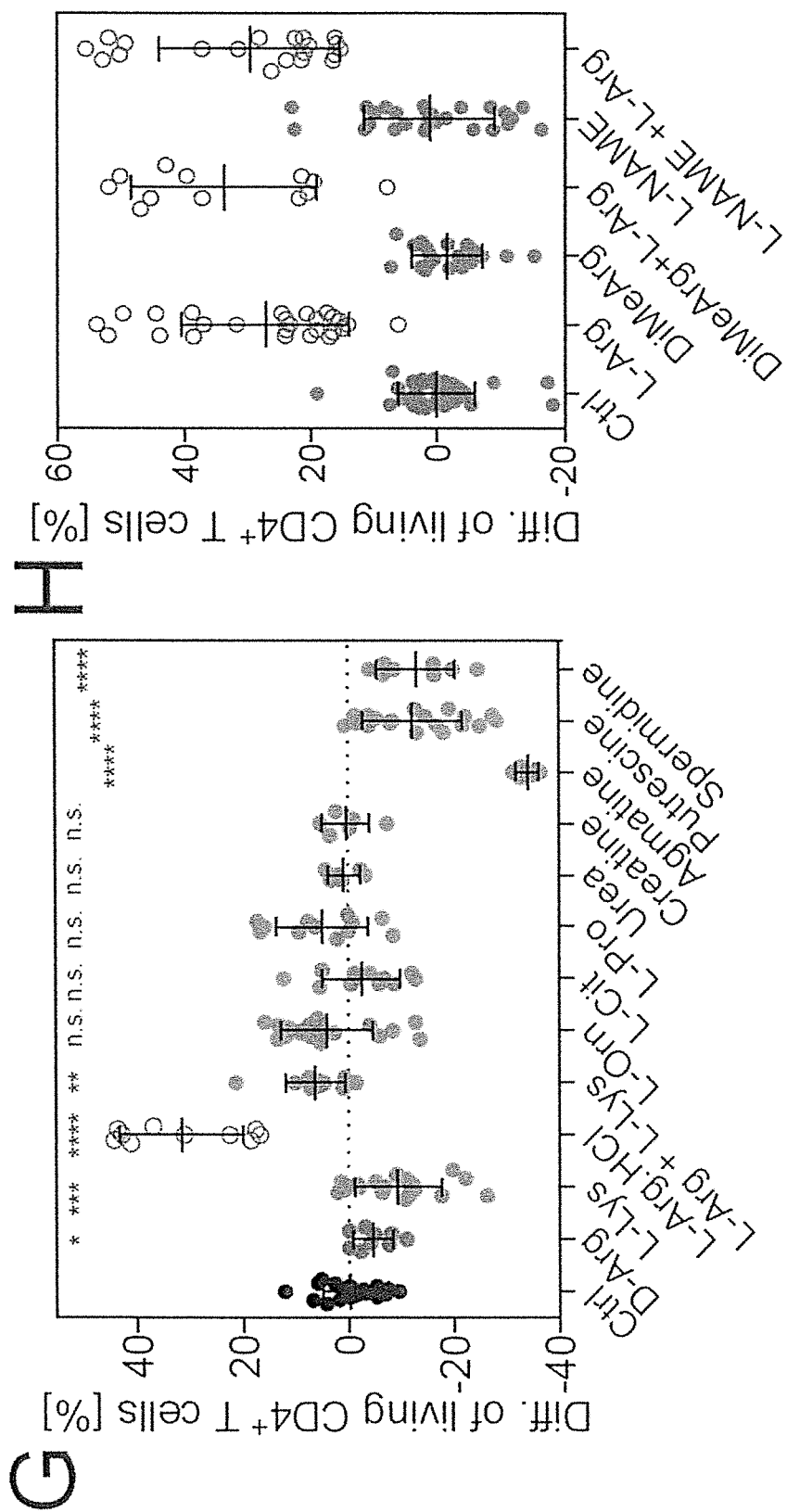
Figure 4 (c'td)

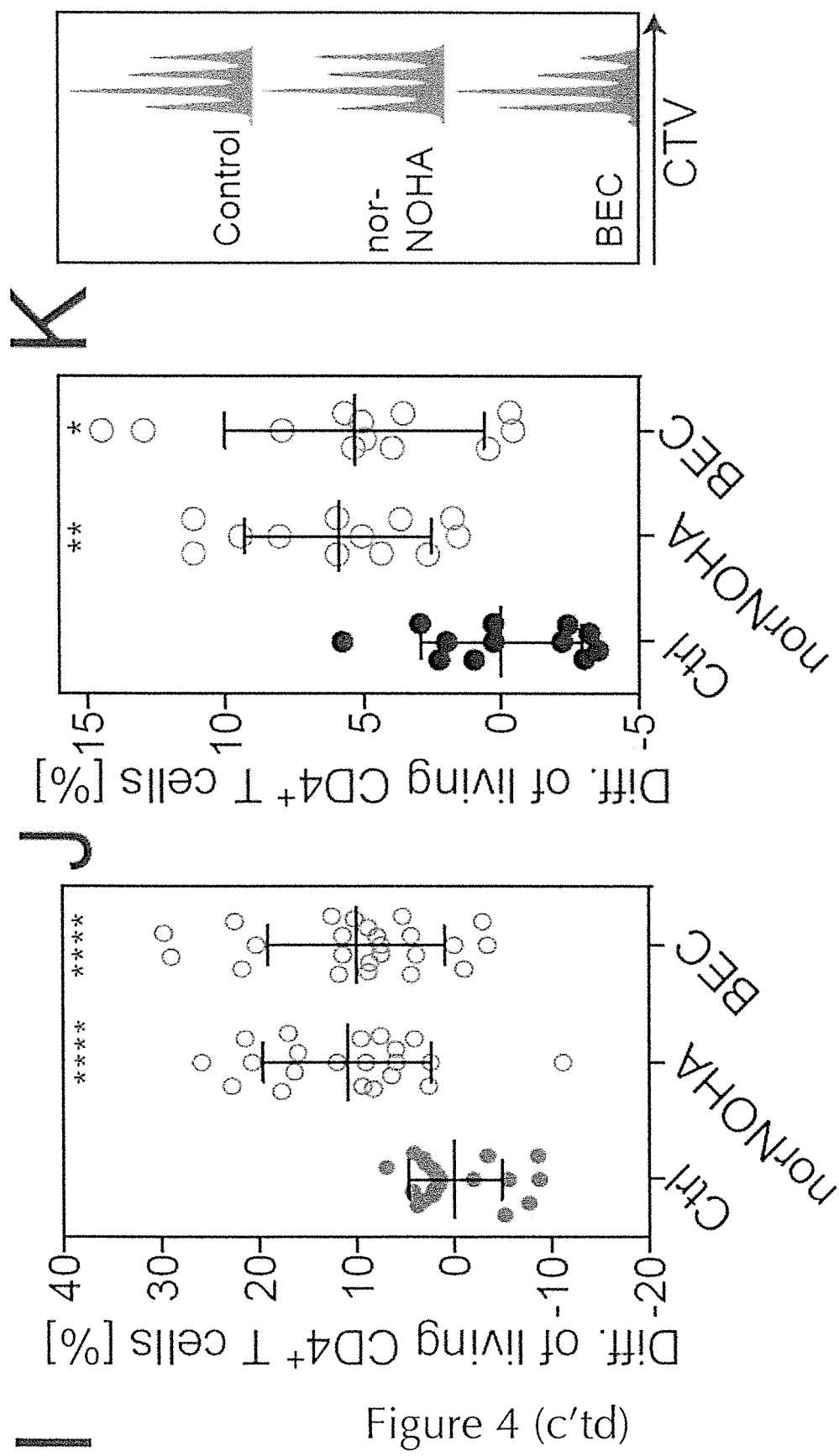
Figure 4 (c'td)

Figure 6:
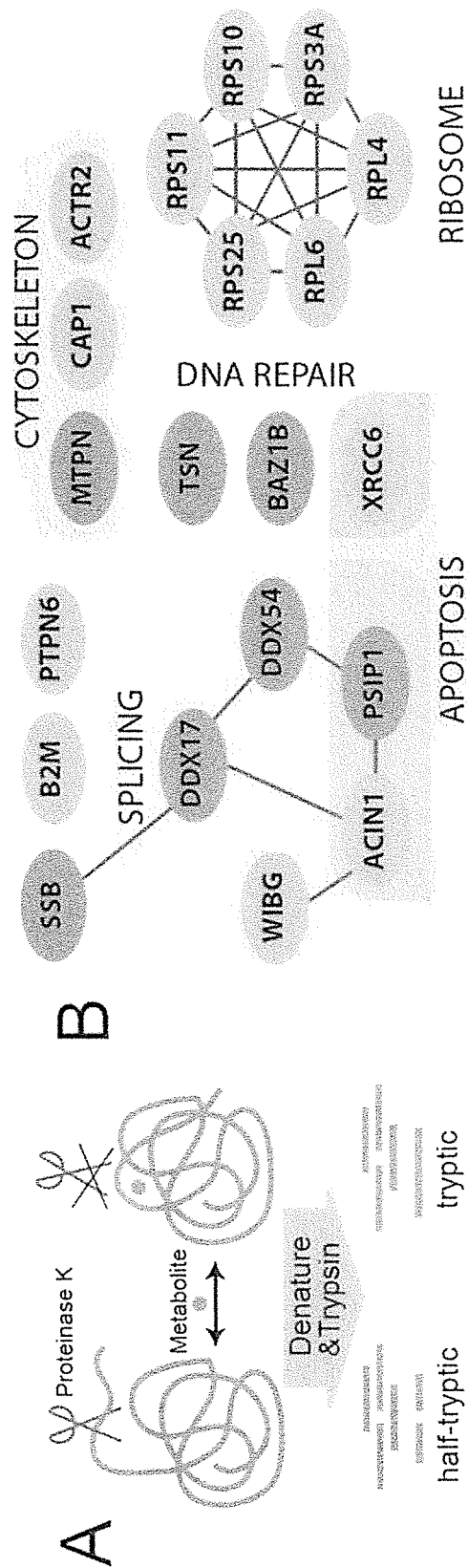

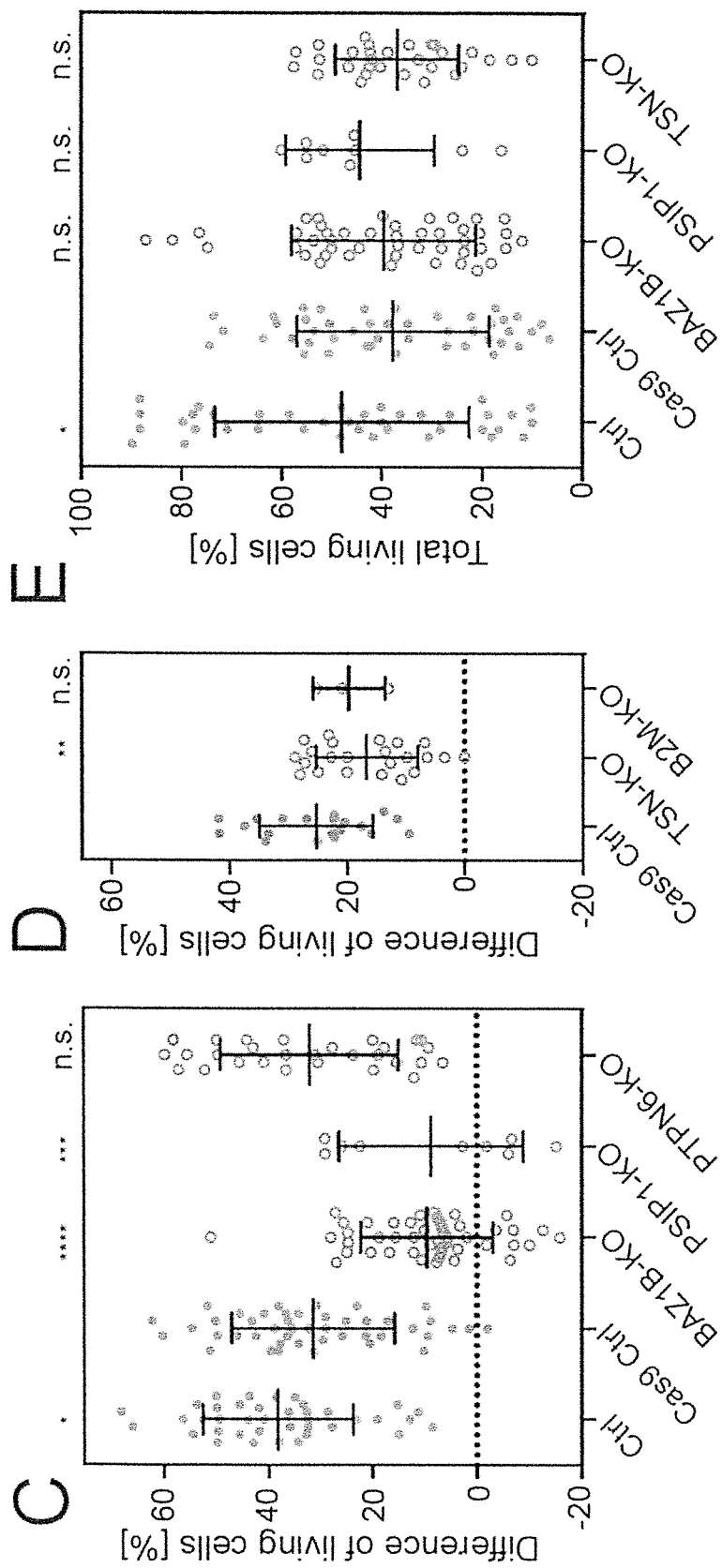
Figure 6 (c'td)

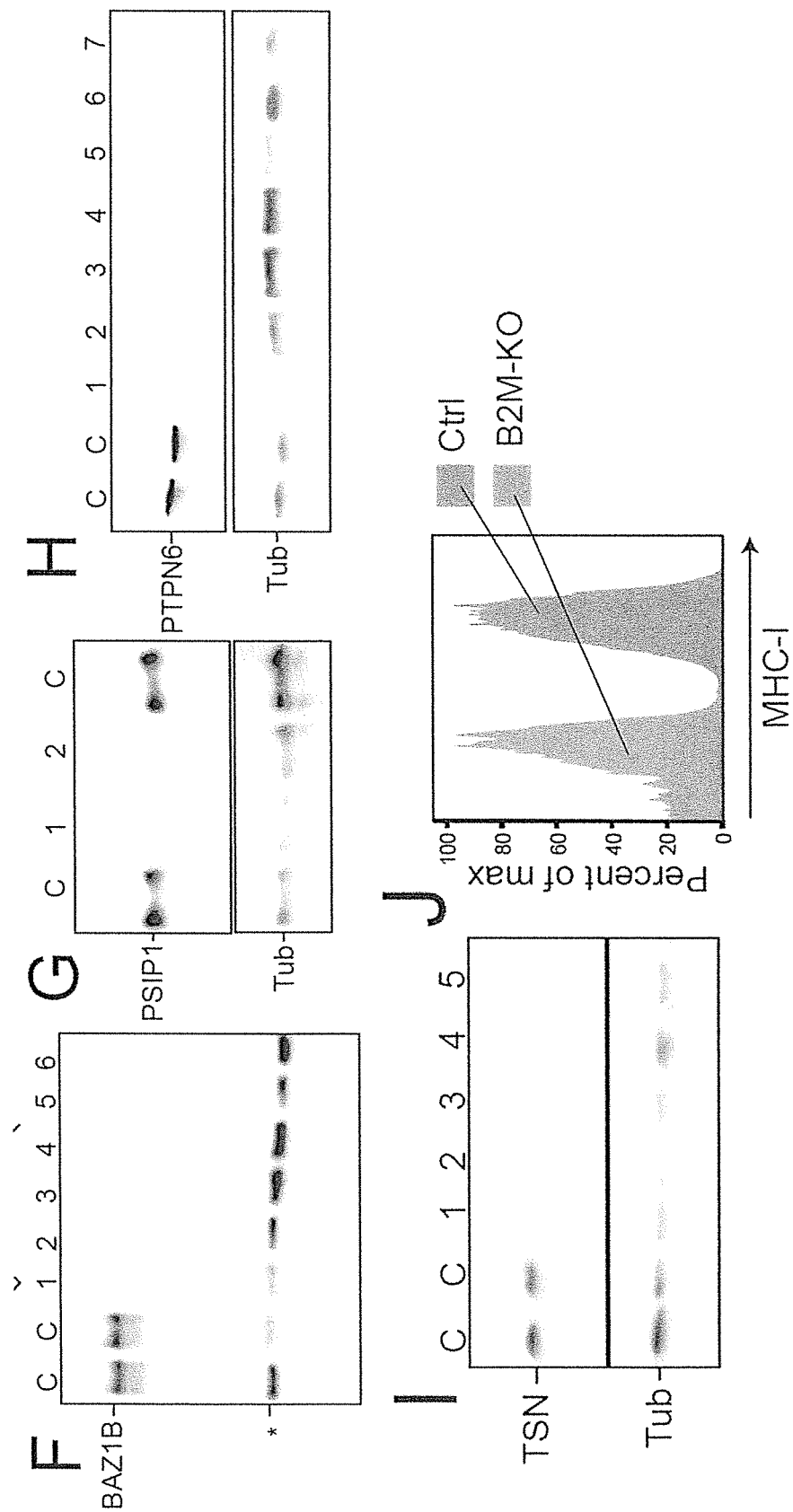
Figure 6 (c'td)

Figure 7:
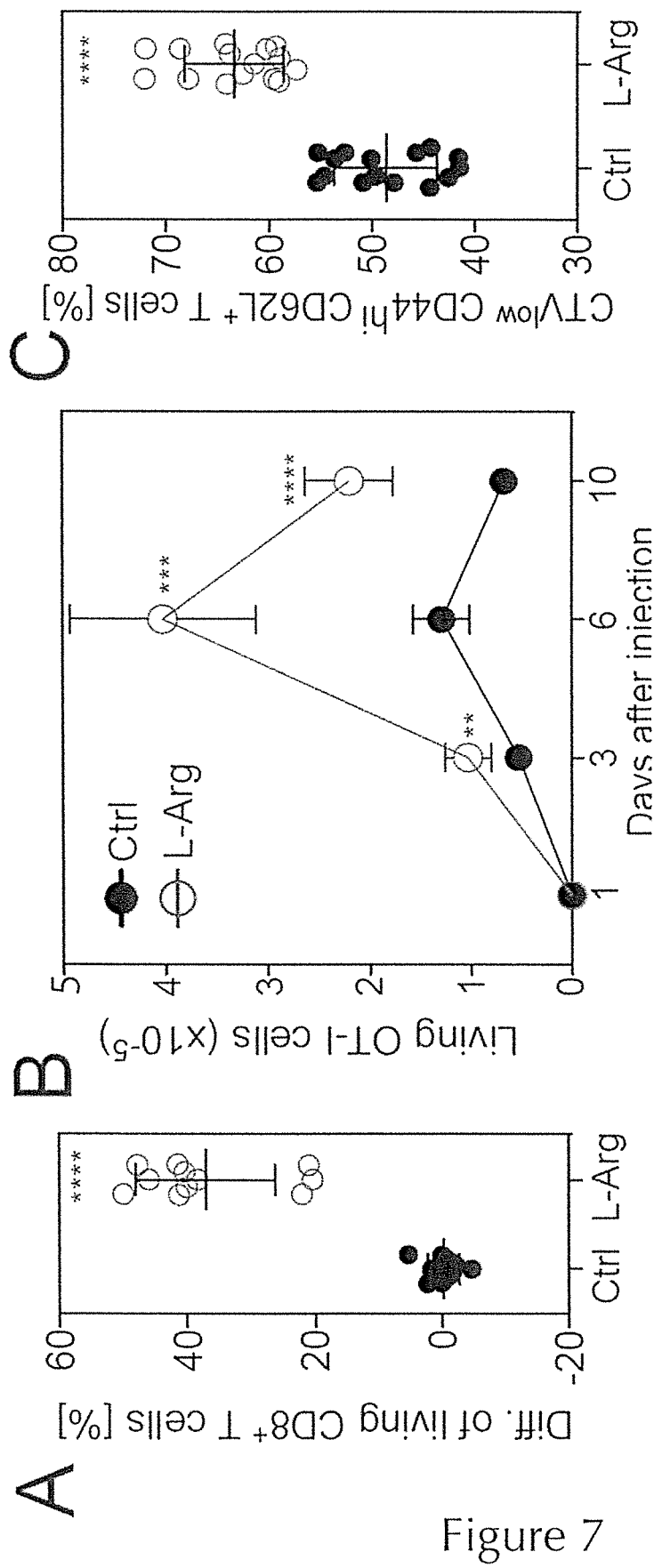

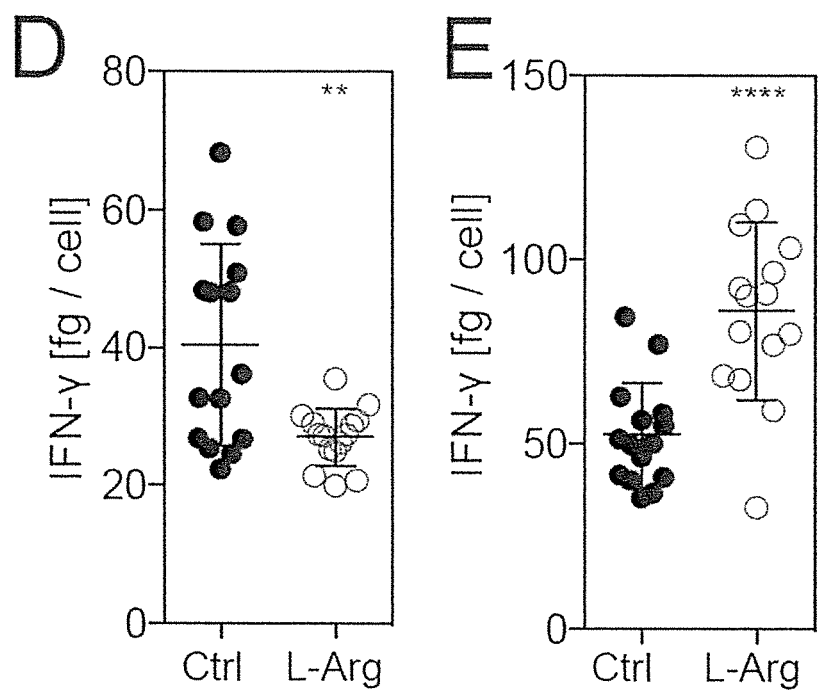
Figure 7 (c'td)

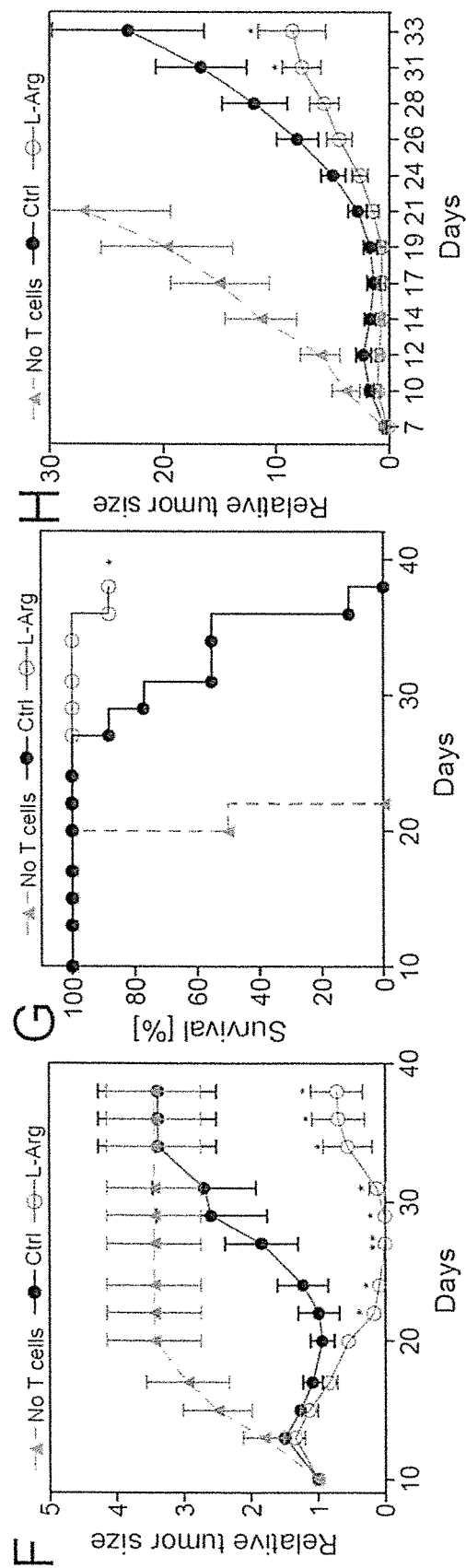
Figure 7 (c'td)

Figure 8:
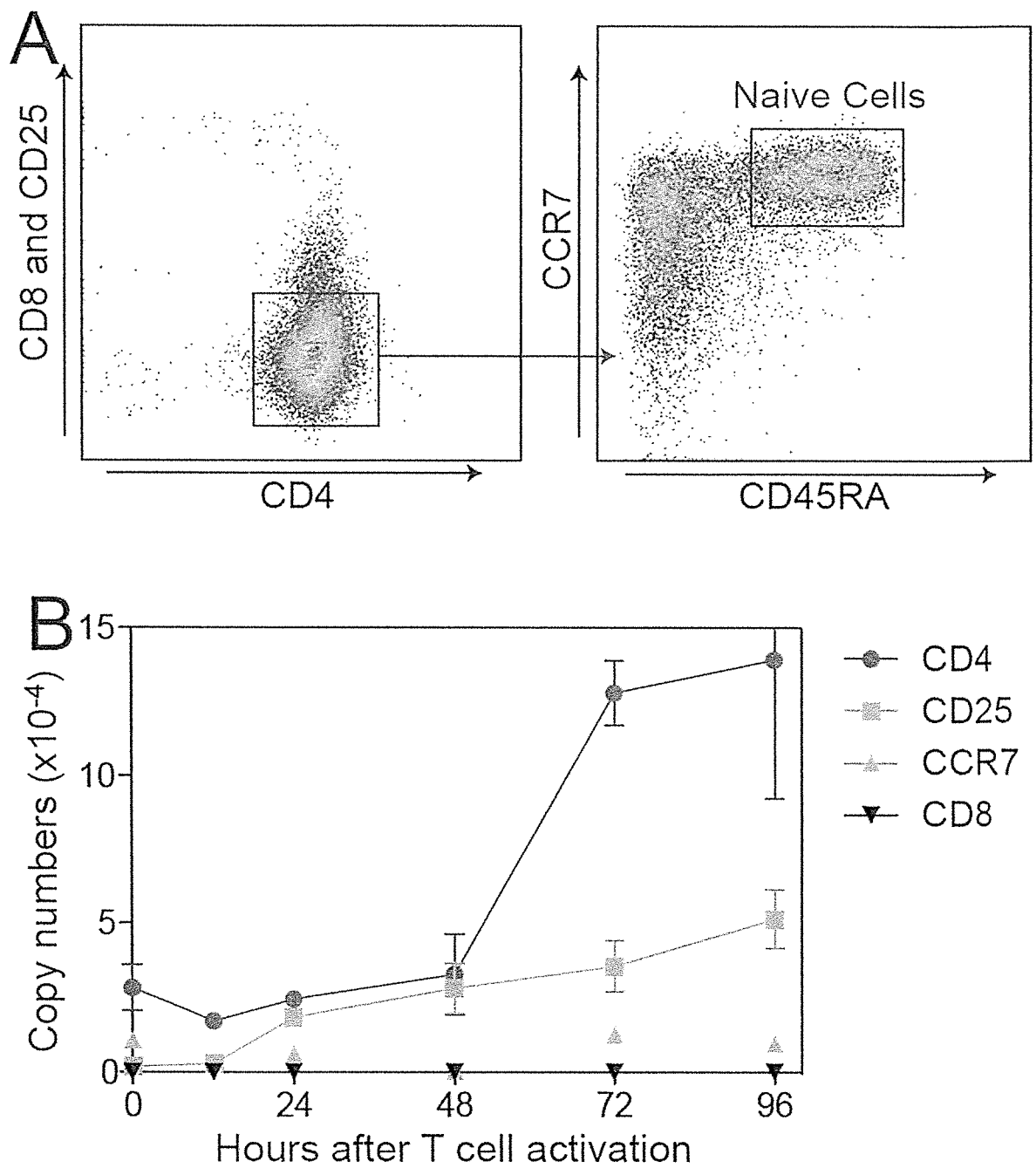

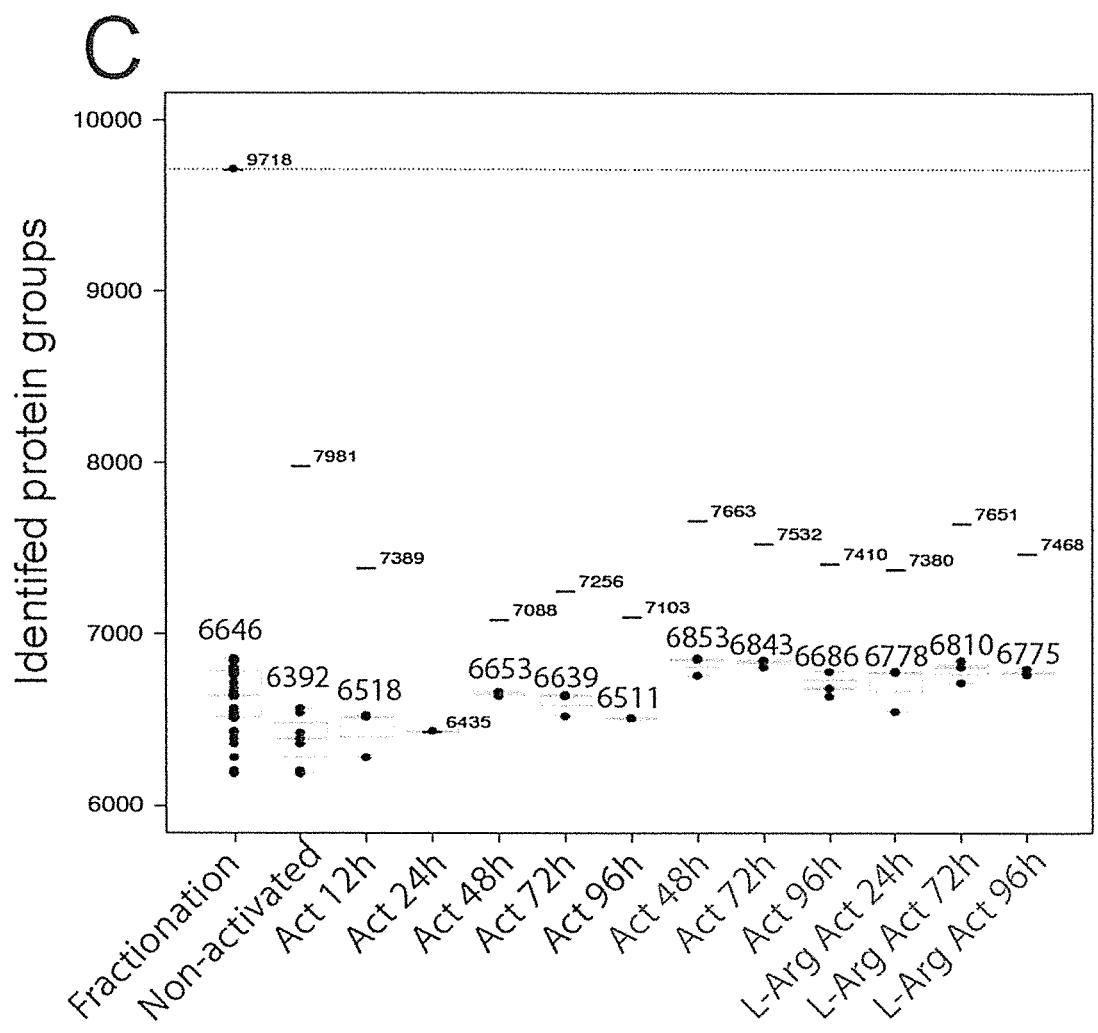
Figure 8 (c'td)

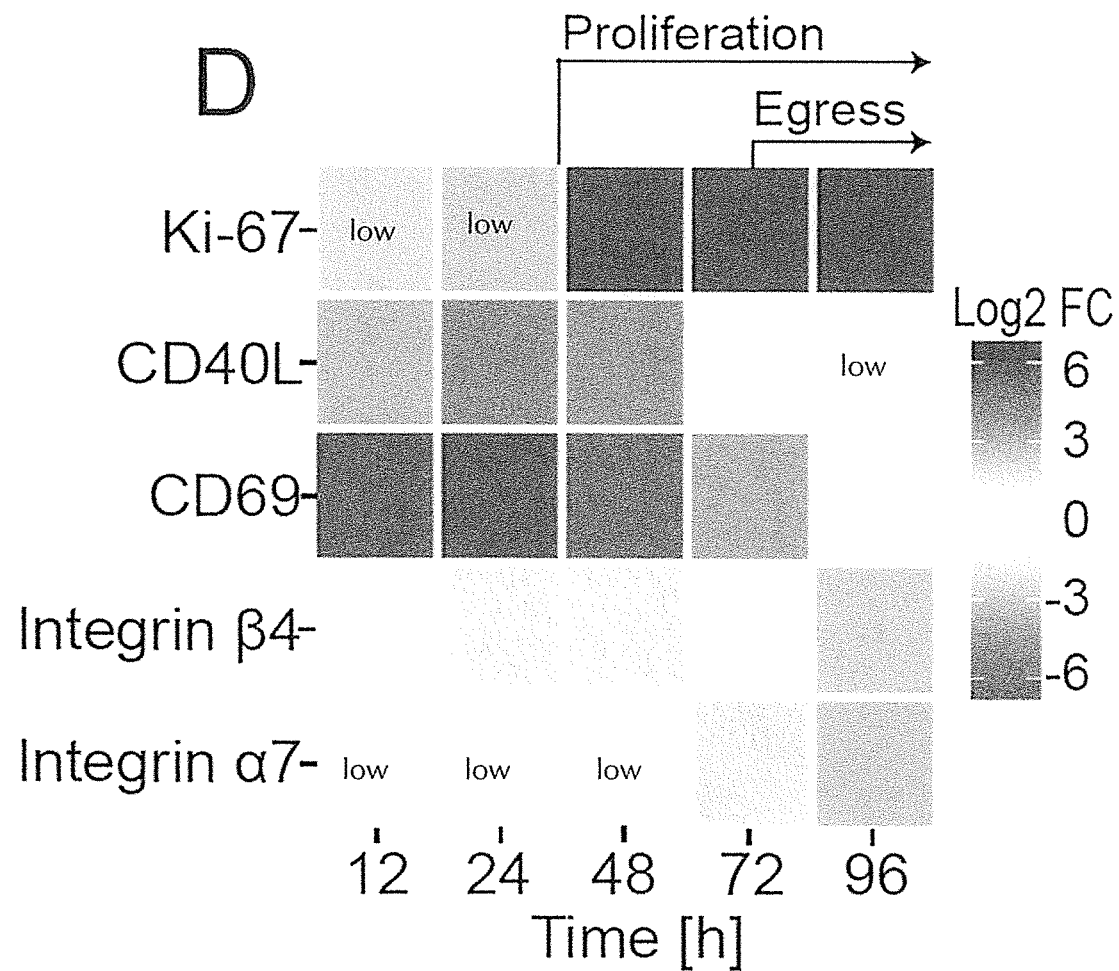
Figure 8 (c'td)

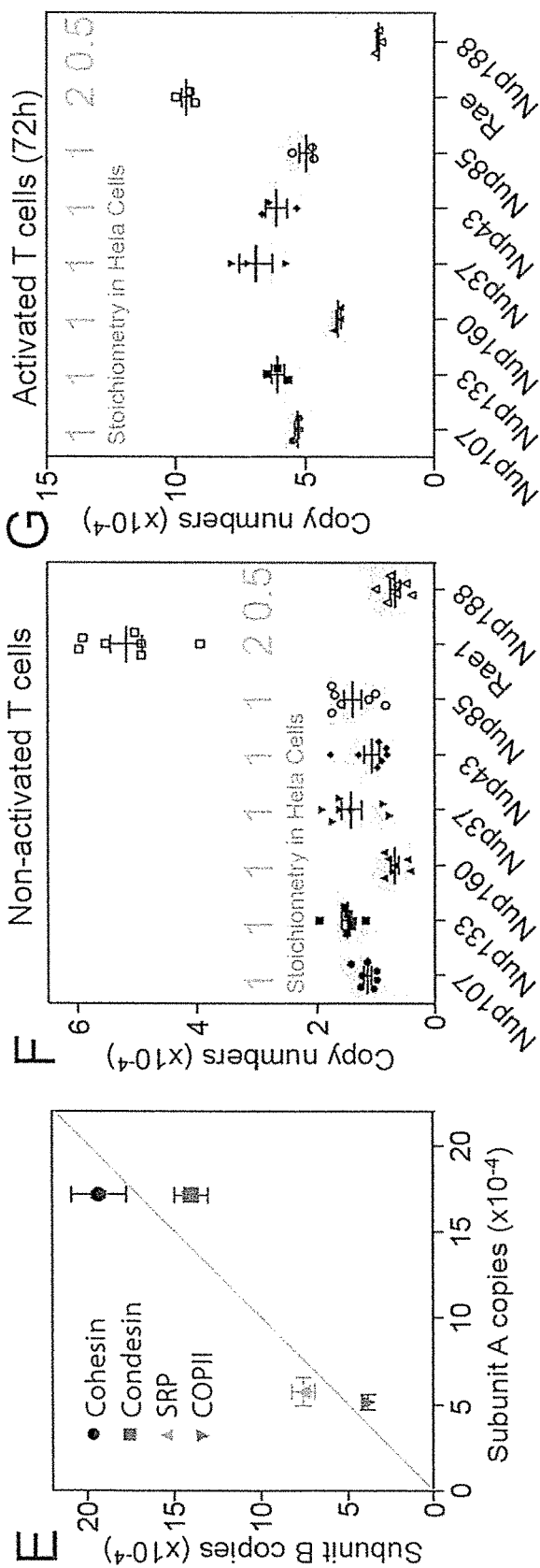
Figure 8 (c'td)

Figure 9:
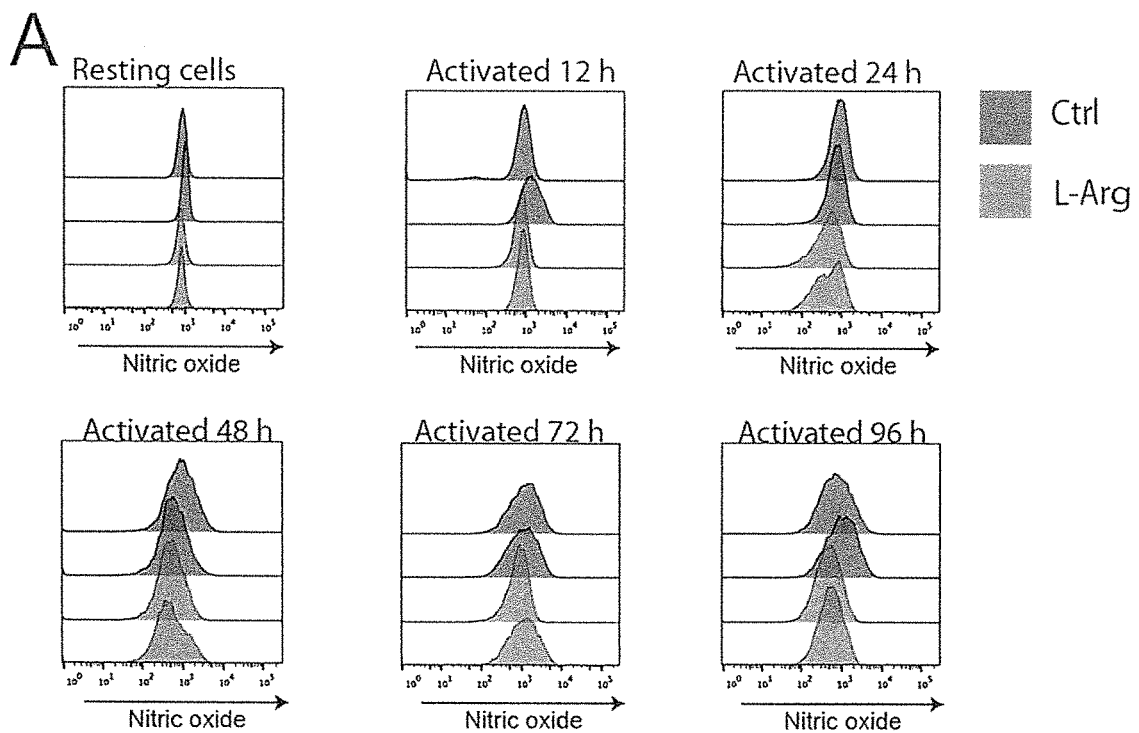

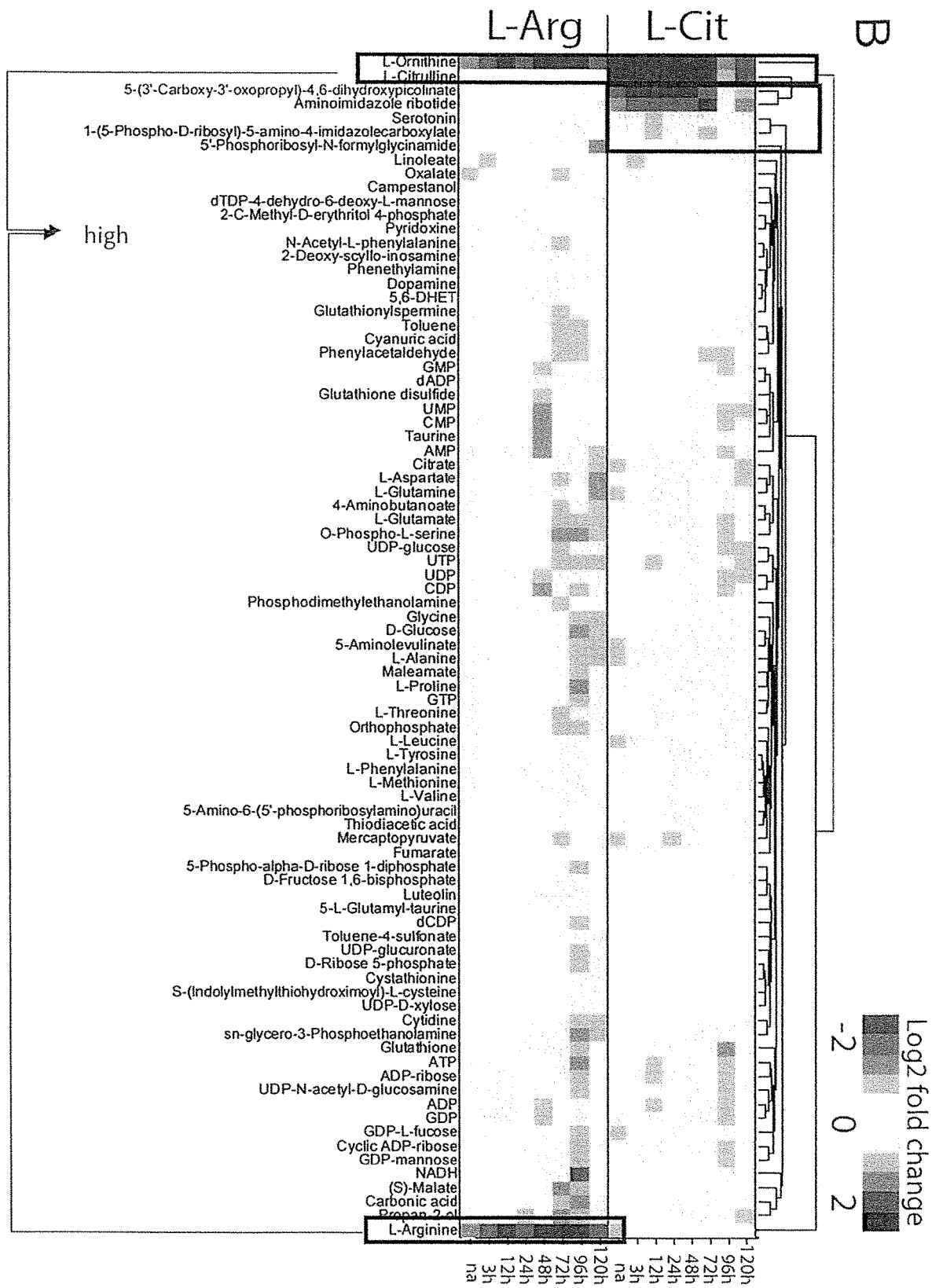
Figure 9 (c'td)

Figure 11:
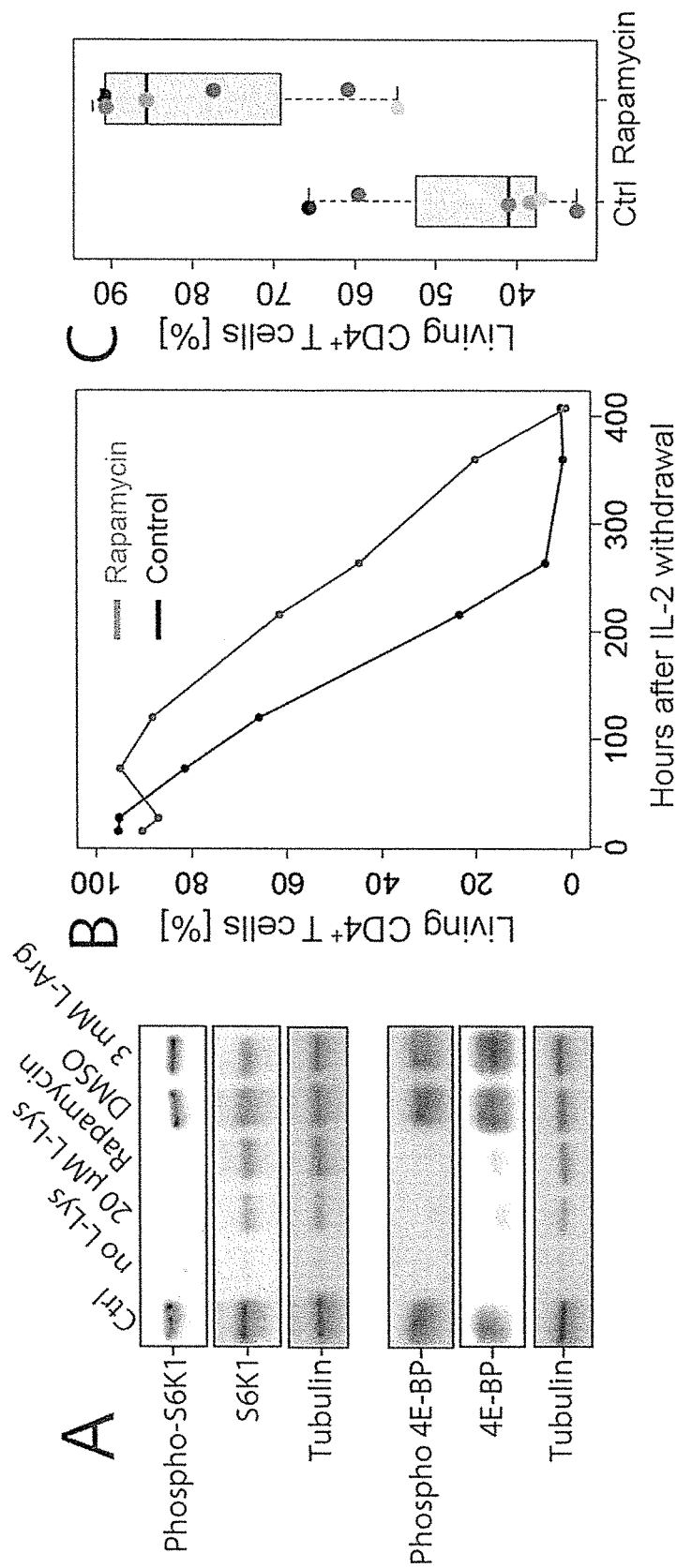

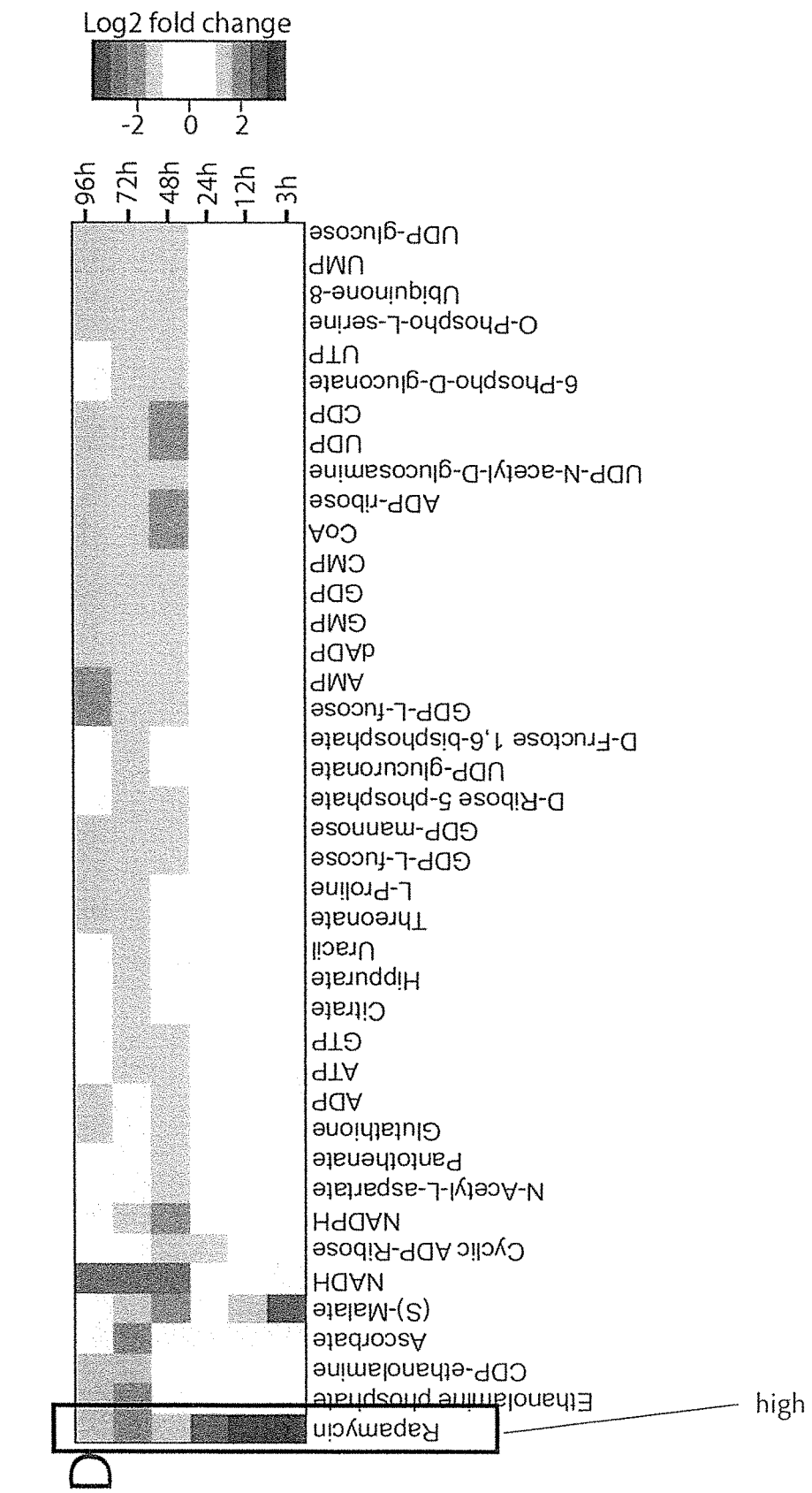
Figure 11 (c'td)

SEQUENCE LISTING

<160> NUMBER OF SEQ ID NOS: 27

<210> SEQ ID NO 1
<211> LENGTH: 1483
<212> TYPE: PRT
<213> ORGANISM: Homo sapiens

<400> SEQUENCE: 1

```
Met Ala Pro Leu Leu Gly Arg Lys Pro Phe Pro Leu Val Lys Pro Leu
1               5                   10                  15

Pro Gly Glu Glu Pro Leu Phe Thr Ile Pro His Thr Gln Glu Ala Phe
            20                  25                  30

Arg Thr Arg Glu Glu Tyr Glu Ala Arg Leu Glu Arg Tyr Ser Glu Arg
        35                  40                  45

Ile Trp Thr Cys Lys Ser Thr Gly Ser Ser Gln Leu Thr His Lys Glu
    50                  55                  60

Ala Trp Glu Glu Glu Gln Glu Val Ala Glu Leu Leu Lys Glu Glu Phe
65                  70                  75                  80

Pro Ala Trp Tyr Glu Lys Leu Val Leu Glu Met Val His His Asn Thr
                85                  90                  95

Ala Ser Leu Glu Lys Leu Val Asp Thr Ala Trp Leu Glu Ile Met Thr
            100                 105                 110

Lys Tyr Ala Val Gly Glu Glu Cys Asp Phe Glu Val Gly Lys Glu Lys
        115                 120                 125

Met Leu Lys Val Lys Ile Val Lys Ile His Pro Leu Glu Lys Val Asp
    130                 135                 140

Glu Glu Ala Thr Glu Lys Lys Ser Asp Gly Ala Cys Asp Ser Pro Ser
145                 150                 155                 160

Ser Asp Lys Glu Asn Ser Ser Gln Ile Ala Gln Asp His Gln Lys Lys
                165                 170                 175

Glu Thr Val Val Lys Glu Asp Glu Gly Arg Arg Glu Ser Ile Asn Asp
            180                 185                 190

Arg Ala Arg Arg Ser Pro Arg Lys Leu Pro Thr Ser Leu Lys Lys Gly
        195                 200                 205

Glu Arg Lys Trp Ala Pro Pro Lys Phe Leu Pro His Lys Tyr Asp Val
    210                 215                 220

Lys Leu Gln Asn Glu Asp Lys Ile Ile Ser Asn Val Pro Ala Asp Ser
225                 230                 235                 240

Leu Ile Arg Thr Glu Arg Pro Asn Lys Glu Ile Val Arg Tyr Phe
                245                 250                 255

Ile Arg His Asn Ala Leu Arg Ala Gly Thr Gly Glu Asn Ala Pro Trp
            260                 265                 270

Val Val Glu Asp Glu Leu Val Lys Lys Tyr Ser Leu Pro Ser Lys Phe
        275                 280                 285

Ser Asp Phe Leu Leu Asp Pro Tyr Lys Tyr Met Thr Leu Asn Pro Ser
    290                 295                 300

Thr Lys Arg Lys Asn Thr Gly Ser Pro Asp Arg Lys Pro Ser Lys Lys
305                 310                 315                 320

Ser Lys Thr Asp Asn Ser Ser Leu Ser Ser Pro Leu Asn Pro Lys Leu
                325                 330                 335

Trp Cys His Val His Leu Lys Lys Ser Leu Ser Gly Ser Pro Leu Lys
            340                 345                 350

Val Lys Asn Ser Lys Asn Ser Ser Pro Glu Glu His Leu Glu Glu
        355                 360                 365
```

```
Met Met Lys Met Met Ser Pro Asn Lys Leu His Thr Asn Phe His Ile
370                 375                 380
Pro Lys Lys Gly Pro Pro Ala Lys Lys Pro Gly Lys His Ser Asp Lys
385                 390                 395                 400
Pro Leu Lys Ala Lys Gly Arg Ser Lys Gly Ile Leu Asn Gly Gln Lys
                405                 410                 415
Ser Thr Gly Asn Ser Lys Ser Pro Lys Lys Gly Leu Lys Thr Pro Lys
                420                 425                 430
Thr Lys Met Lys Gln Met Thr Leu Leu Asp Met Ala Lys Gly Thr Gln
            435                 440                 445
Lys Met Thr Arg Ala Pro Arg Asn Ser Gly Gly Thr Pro Arg Thr Ser
450                 455                 460
Ser Lys Pro His Lys His Leu Pro Pro Ala Ala Leu His Leu Ile Ala
465                 470                 475                 480
Tyr Tyr Lys Glu Asn Lys Asp Arg Glu Asp Lys Arg Ser Ala Leu Ser
                485                 490                 495
Cys Val Ile Ser Lys Thr Ala Arg Leu Leu Ser Ser Glu Asp Arg Ala
            500                 505                 510
Arg Leu Pro Glu Glu Leu Arg Ser Leu Val Gln Lys Arg Tyr Glu Leu
            515                 520                 525
Leu Glu His Lys Lys Arg Trp Ala Ser Met Ser Glu Glu Gln Arg Lys
            530                 535                 540
Glu Tyr Leu Lys Lys Lys Arg Glu Glu Leu Lys Lys Leu Lys Glu
545                 550                 555                 560
Lys Ala Lys Glu Arg Arg Glu Lys Glu Met Leu Glu Arg Leu Glu Lys
                565                 570                 575
Gln Lys Arg Tyr Glu Asp Gln Glu Leu Thr Gly Lys Asn Leu Pro Ala
            580                 585                 590
Phe Arg Leu Val Asp Thr Pro Glu Gly Leu Pro Asn Thr Leu Phe Gly
            595                 600                 605
Asp Val Ala Met Val Val Glu Phe Leu Ser Cys Tyr Ser Gly Leu Leu
610                 615                 620
Leu Pro Asp Ala Gln Tyr Pro Ile Thr Ala Val Ser Leu Met Glu Ala
625                 630                 635                 640
Leu Ser Ala Asp Lys Gly Gly Phe Leu Tyr Leu Asn Arg Val Leu Val
                645                 650                 655
Ile Leu Leu Gln Thr Leu Leu Gln Asp Glu Ile Ala Glu Asp Tyr Gly
            660                 665                 670
Glu Leu Gly Met Lys Leu Ser Glu Ile Pro Leu Thr Leu His Ser Val
            675                 680                 685
Ser Glu Leu Val Arg Leu Cys Leu Arg Arg Ser Asp Val Gln Glu Glu
690                 695                 700
Ser Glu Gly Ser Asp Thr Asp Asp Asn Lys Asp Ser Ala Ala Phe Glu
705                 710                 715                 720
Asp Asn Glu Val Gln Asp Glu Phe Leu Glu Lys Leu Glu Thr Ser Glu
                725                 730                 735
Phe Phe Glu Leu Thr Ser Glu Glu Lys Leu Gln Ile Leu Thr Ala Leu
            740                 745                 750
Cys His Arg Ile Leu Met Thr Tyr Ser Val Gln Asp His Met Glu Thr
            755                 760                 765
Arg Gln Gln Met Ser Ala Glu Leu Trp Lys Glu Arg Leu Ala Val Leu
770                 775                 780
Lys Glu Glu Asn Asp Lys Lys Arg Ala Glu Lys Gln Lys Arg Lys Glu
```

```
            785                 790                 795                 800
        Met Glu Ala Lys Asn Lys Glu Asn Gly Lys Val Glu Asn Gly Leu Gly
                        805                 810                 815
        Lys Thr Asp Arg Lys Lys Glu Ile Val Lys Phe Glu Pro Gln Val Asp
                        820                 825                 830
        Thr Glu Ala Glu Asp Met Ile Ser Ala Val Lys Ser Arg Arg Leu Leu
                        835                 840                 845
        Ala Ile Gln Ala Lys Lys Glu Arg Glu Ile Gln Glu Arg Glu Met Lys
                        850                 855                 860
        Val Lys Leu Glu Arg Gln Ala Glu Glu Arg Ile Arg Lys His Lys
        865                 870                 875                 880
        Ala Ala Ala Glu Lys Ala Phe Gln Glu Gly Ile Ala Lys Ala Lys Leu
                        885                 890                 895
        Val Met Arg Arg Thr Pro Ile Gly Thr Asp Arg Asn His Asn Arg Tyr
                        900                 905                 910
        Trp Leu Phe Ser Asp Glu Val Pro Gly Leu Phe Ile Glu Lys Gly Trp
                        915                 920                 925
        Val His Asp Ser Ile Asp Tyr Arg Phe Asn His His Cys Lys Asp His
                        930                 935                 940
        Thr Val Ser Gly Asp Glu Asp Tyr Cys Pro Arg Ser Lys Lys Ala Asn
        945                 950                 955                 960
        Leu Gly Lys Asn Ala Ser Met Asn Thr Gln His Gly Thr Ala Thr Glu
                        965                 970                 975
        Val Ala Val Glu Thr Thr Thr Pro Lys Gln Gly Gln Asn Leu Trp Phe
                        980                 985                 990
        Leu Cys Asp Ser Gln Lys Glu Leu Asp Glu Leu Leu Asn Cys Leu His
                        995                 1000                1005
        Pro Gln Gly Ile Arg Glu Ser Gln Leu Lys Glu Arg Leu Glu Lys
                    1010                1015                1020
        Arg Tyr Gln Asp Ile Ile His Ser Ile His Leu Ala Arg Lys Pro
                    1025                1030                1035
        Asn Leu Gly Leu Lys Ser Cys Asp Gly Asn Gln Glu Leu Leu Asn
                    1040                1045                1050
        Phe Leu Arg Ser Asp Leu Ile Glu Val Ala Thr Arg Leu Gln Lys
                    1055                1060                1065
        Gly Gly Leu Gly Tyr Val Glu Thr Ser Glu Phe Glu Ala Arg
                    1070                1075                1080
        Val Ile Ser Leu Glu Lys Leu Lys Asp Phe Gly Glu Cys Val Ile
                    1085                1090                1095
        Ala Leu Gln Ala Ser Val Ile Lys Lys Phe Leu Gln Gly Phe Met
                    1100                1105                1110
        Ala Pro Lys Gln Lys Arg Arg Lys Leu Gln Ser Glu Asp Ser Ala
                    1115                1120                1125
        Lys Thr Glu Glu Val Asp Glu Glu Lys Lys Met Val Glu Glu Ala
                    1130                1135                1140
        Lys Val Ala Ser Ala Leu Glu Lys Trp Lys Thr Ala Ile Arg Glu
                    1145                1150                1155
        Ala Gln Thr Phe Ser Arg Met His Val Leu Leu Gly Met Leu Asp
                    1160                1165                1170
        Ala Cys Ile Lys Trp Asp Met Ser Ala Glu Asn Ala Arg Cys Lys
                    1175                1180                1185
        Val Cys Arg Lys Lys Gly Glu Asp Asp Lys Leu Ile Leu Cys Asp
                    1190                1195                1200
```

```
Glu Cys Asn Lys Ala Phe His Leu Phe Cys Leu Arg Pro Ala Leu
    1205                1210                1215

Tyr Glu Val Pro Asp Gly Glu Trp Gln Cys Pro Ala Cys Gln Pro
    1220                1225                1230

Ala Thr Ala Arg Arg Asn Ser Arg Gly Arg Asn Tyr Thr Glu Glu
    1235                1240                1245

Ser Ala Ser Glu Asp Ser Glu Asp Asp Glu Ser Asp Glu Glu Glu
    1250                1255                1260

Glu Glu Glu Glu Glu Glu Glu Glu Glu Asp Tyr Glu Val Ala
    1265                1270                1275

Gly Leu Arg Leu Arg Pro Arg Lys Thr Ile Arg Gly Lys His Ser
    1280                1285                1290

Val Ile Pro Pro Ala Ala Arg Ser Gly Arg Arg Pro Gly Lys Lys
    1295                1300                1305

Pro His Ser Thr Arg Arg Ser Gln Pro Lys Ala Pro Pro Val Asp
    1310                1315                1320

Asp Ala Glu Val Asp Glu Leu Val Leu Gln Thr Lys Arg Ser Ser
    1325                1330                1335

Arg Arg Gln Ser Leu Glu Leu Gln Lys Cys Glu Glu Ile Leu His
    1340                1345                1350

Lys Ile Val Lys Tyr Arg Phe Ser Trp Pro Phe Arg Glu Pro Val
    1355                1360                1365

Thr Arg Asp Glu Ala Glu Asp Tyr Tyr Asp Val Ile Thr His Pro
    1370                1375                1380

Met Asp Phe Gln Thr Val Gln Asn Lys Cys Ser Cys Gly Ser Tyr
    1385                1390                1395

Arg Ser Val Gln Glu Phe Leu Thr Asp Met Lys Gln Val Phe Thr
    1400                1405                1410

Asn Ala Glu Val Tyr Asn Cys Arg Gly Ser His Val Leu Ser Cys
    1415                1420                1425

Met Val Lys Thr Glu Gln Cys Leu Val Ala Leu Leu His Lys His
    1430                1435                1440

Leu Pro Gly His Pro Tyr Val Arg Arg Lys Arg Lys Lys Phe Pro
    1445                1450                1455

Asp Arg Leu Ala Glu Asp Gly Asp Ser Glu Pro Glu Ala Val
    1460                1465                1470

Gly Gln Ser Arg Gly Arg Gln Lys Lys
    1475                1480

<210> SEQ ID NO 2
<211> LENGTH: 530
<212> TYPE: PRT
<213> ORGANISM: Homo sapiens

<400> SEQUENCE: 2

Met Thr Arg Asp Phe Lys Pro Gly Asp Leu Ile Phe Ala Lys Met Lys
1               5                   10                  15

Gly Tyr Pro His Trp Pro Ala Arg Val Asp Glu Val Pro Asp Gly Ala
            20                  25                  30

Val Lys Pro Pro Thr Asn Lys Leu Pro Ile Phe Phe Phe Gly Thr His
        35                  40                  45

Glu Thr Ala Phe Leu Gly Pro Lys Asp Ile Phe Pro Tyr Ser Glu Asn
    50                  55                  60

Lys Glu Lys Tyr Gly Lys Pro Asn Lys Arg Lys Gly Phe Asn Glu Gly
```

```
                65                  70                  75                  80
Leu Trp Glu Ile Asp Asn Asn Pro Lys Val Lys Phe Ser Ser Gln Gln
                    85                  90                  95

Ala Ala Thr Lys Gln Ser Asn Ala Ser Ser Asp Val Glu Val Glu Glu
                100                 105                 110

Lys Glu Thr Ser Val Ser Lys Glu Asp Thr Asp His Glu Glu Lys Ala
                115                 120                 125

Ser Asn Glu Asp Val Thr Lys Ala Val Asp Ile Thr Thr Pro Lys Ala
    130                 135                 140

Ala Arg Arg Gly Arg Lys Arg Lys Ala Glu Lys Gln Val Glu Thr Glu
145                 150                 155                 160

Glu Ala Gly Val Val Thr Thr Ala Thr Ala Ser Val Asn Leu Lys Val
                    165                 170                 175

Ser Pro Lys Arg Gly Arg Pro Ala Ala Thr Glu Val Lys Ile Pro Lys
                180                 185                 190

Pro Arg Gly Arg Pro Lys Met Val Lys Gln Pro Cys Pro Ser Glu Ser
                195                 200                 205

Asp Ile Ile Thr Glu Glu Asp Lys Ser Lys Lys Gly Gln Glu Glu
    210                 215                 220

Lys Gln Pro Lys Lys Gln Pro Lys Asp Glu Gly Gln Lys Glu
225                 230                 235                 240

Glu Asp Lys Pro Arg Lys Glu Pro Asp Lys Glu Gly Lys Lys Glu
                    245                 250                 255

Val Glu Ser Lys Arg Lys Asn Leu Ala Lys Thr Gly Val Thr Ser Thr
                260                 265                 270

Ser Asp Ser Glu Glu Glu Gly Asp Asp Gln Gly Glu Lys Lys Arg
    275                 280                 285

Lys Gly Gly Arg Asn Phe Gln Thr Ala His Arg Asn Met Leu Lys
290                 295                 300

Gly Gln His Glu Lys Glu Ala Ala Asp Arg Lys Arg Lys Gln Glu Glu
305                 310                 315                 320

Gln Met Glu Thr Glu Gln Gln Asn Lys Asp Glu Gly Lys Lys Pro Glu
                325                 330                 335

Val Lys Lys Val Glu Lys Lys Arg Glu Thr Ser Met Asp Ser Arg Leu
                340                 345                 350

Gln Arg Ile His Ala Glu Ile Lys Asn Ser Leu Lys Ile Asp Asn Leu
                355                 360                 365

Asp Val Asn Arg Cys Ile Glu Ala Leu Asp Glu Leu Ala Ser Leu Gln
    370                 375                 380

Val Thr Met Gln Gln Ala Gln Lys His Thr Glu Met Ile Thr Thr Leu
385                 390                 395                 400

Lys Lys Ile Arg Arg Phe Lys Val Ser Gln Val Ile Met Glu Lys Ser
                405                 410                 415

Thr Met Leu Tyr Asn Lys Phe Lys Asn Met Phe Leu Val Gly Glu Gly
                420                 425                 430

Asp Ser Val Ile Thr Gln Val Leu Asn Lys Ser Leu Ala Glu Gln Arg
    435                 440                 445

Gln His Glu Glu Ala Asn Lys Thr Lys Asp Gln Gly Lys Lys Gly Pro
450                 455                 460

Asn Lys Lys Leu Glu Lys Glu Gln Thr Gly Ser Lys Thr Leu Asn Gly
465                 470                 475                 480

Gly Ser Asp Ala Gln Asp Gly Asn Gln Pro Gln His Asn Gly Glu Ser
                485                 490                 495
```

Asn Glu Asp Ser Lys Asp Asn His Glu Ala Ser Thr Lys Lys Pro
            500                 505                 510

Ser Ser Glu Glu Arg Glu Thr Glu Ile Ser Leu Lys Asp Ser Thr Leu
            515                 520                 525

Asp Asn
    530

<210> SEQ ID NO 3
<211> LENGTH: 228
<212> TYPE: PRT
<213> ORGANISM: Homo sapiens

<400> SEQUENCE: 3

Met Ser Val Ser Glu Ile Phe Val Glu Leu Gln Gly Phe Leu Ala Ala
1               5                   10                  15

Glu Gln Asp Ile Arg Glu Ile Arg Lys Val Val Gln Ser Leu Glu
            20                  25                  30

Gln Thr Ala Arg Glu Ile Leu Thr Leu Leu Gln Gly Val His Gln Gly
        35                  40                  45

Ala Gly Phe Gln Asp Ile Pro Lys Arg Cys Leu Lys Ala Arg Glu His
    50                  55                  60

Phe Gly Thr Val Lys Thr His Leu Thr Ser Leu Lys Thr Lys Phe Pro
65                  70                  75                  80

Ala Glu Gln Tyr Tyr Arg Phe His Glu His Trp Arg Phe Val Leu Gln
                85                  90                  95

Arg Leu Val Phe Leu Ala Ala Phe Val Val Tyr Leu Glu Thr Glu Thr
            100                 105                 110

Leu Val Thr Arg Glu Ala Val Thr Glu Ile Leu Gly Ile Glu Pro Asp
        115                 120                 125

Arg Glu Lys Gly Phe His Leu Asp Val Glu Asp Tyr Leu Ser Gly Val
    130                 135                 140

Leu Ile Leu Ala Ser Glu Leu Ser Arg Leu Ser Val Asn Ser Val Thr
145                 150                 155                 160

Ala Gly Asp Tyr Ser Arg Pro Leu His Ile Ser Thr Phe Ile Asn Glu
                165                 170                 175

Leu Asp Ser Gly Phe Arg Leu Leu Asn Leu Lys Asn Asp Ser Leu Arg
            180                 185                 190

Lys Arg Tyr Asp Gly Leu Lys Tyr Asp Val Lys Lys Val Glu Glu Val
        195                 200                 205

Val Tyr Asp Leu Ser Ile Arg Gly Phe Asn Lys Glu Thr Ala Ala Ala
    210                 215                 220

Cys Val Glu Lys
225

<210> SEQ ID NO 4
<211> LENGTH: 6063
<212> TYPE: DNA
<213> ORGANISM: Homo sapiens

<400> SEQUENCE: 4
gaggagtcgt gactgccggc cgccgggacc cgaagcggag gtcggcgggg ggctgctggg      60
aggcgcggcg gtgtgcgcgg gagctctgcg ccgtggcgtt ccgctccatg actgtcgcgc     120
ggccgcgccg gcggtgaggg agccggagtt cgcgccgccc tctcacccct cccttccccc     180
accccacccc cgggcgcctg gcgctcgctc cgggccgcgg ggcctagtgc tgcgccgcgg     240

```
ggccggcccc agcagccgcc agtccccacc gccgccgccg cgatggcgcc gctcctgggc    300
cgcaagccct tcccgctggt gaagccgttg cccggagagg agccgctctt caccatcccg    360
cacactcagg aggccttccg cacccgggaa gagtatgaag cccgcttgga aaggtacagt    420
gagcgcattt ggacgtgcaa gagtactgga agcagtcagc taacacacaa ggaagcctgg    480
gaggaagaac aggaagttgc tgagcttttg aaggaggagt ttcctgcctg gtatgagaag    540
cttgttctgg aaatggttca ccataacaca gcctccttag agaagttagt agatactgct    600
tggttggaga tcatgaccaa atatgctgtg ggagaagagt gtgacttcga ggttgggaag    660
gagaaaatgc tcaaggtgaa gattgtgaag attcatcctt tggagaaagt ggatgaagag    720
gccactgaga agaaatctga tggtgcctgt gattctccat caagtgacaa agagaactcc    780
agtcagattg ctcaggacca tcagaagaag gagacagttg tgaaagagga tgaaggaagg    840
agagagagta ttaatgacag agcacgtaga tcgccacgaa aacttcctac ttcattaaaa    900
aaaggagaaa ggaaatgggc tcctccaaaa tttctgcctc acaaatatga tgtgaaacta    960
caaaatgaag ataagatcat cagtaacgtg ccagcagaca gcttgattcg tacagagcgc   1020
ccaccaaata aggagatagt tcgatacttt atacggcata atgcattacg agctggtact   1080
ggtgaaaatg caccttgggt cgtagaagat gaattggtga agaaatactc tctgcccagc   1140
aagttcagtg acttttact tgatccatac aagtatatga ctctcaaccc ttctactaag   1200
aggaagaata ctggatcccc agacaggaag ccctcaaaga aatccaagac agacaactct   1260
tctcttagtt caccactaaa tcctaagtta tggtgtcacg tacacttgaa gaagtcattg   1320
agtggctcgc cactcaaagt gaagaactca agaattccaa atctcctga agaacatcta    1380 gaagaaatga tgaagatgat gtcgcccaat aagctgcaca ctaactttca cattcctaaa   1440
aaaggcccac ctgccaagaa accagggaag cacagtgaca agcctttgaa ggcaaagggc   1500
agaagcaaag gcatcctgaa tggacagaaa tccacaggga attccaaatc tcccaaaaaa   1560
ggactgaaga ctcctaaaac caaaatgaag cagatgactt tgttggatat ggccaaaggc   1620
acgcagaaga tgacacgagc cccacggaat tctggggta cacctaggac ctctagtaaa   1680
cctcataaac atctgcctcc tgcagcccta cacctcattg catactacaa agaaaacaaa   1740
gacagggagg acaagaggag cgccctgtcc tgtgttatct ccaaaacagc tcgtcttctc   1800
tctagtgaag atagagctcg tctcccagaa gaattgcgaa gtcttgttca aaaacgctat   1860
gaacttctag agcacaaaaa gaggtgggct tctatgtctg aagaacaacg gaaagaatat   1920
ttgaaaaaga acgggagga gctgaaaaag aagttgaagg aaaaagccaa agaacgaaga   1980
gagaaagaaa tgcttgagag attagaaaaa cagaagcggt atgaggacca agagttaact   2040
ggcaaaaacc ttccagcatt cagattggtg gatacccctg aagggctgcc caacacgctg   2100
tttggggatg tggccatggt ggtggaattc ttgagctgtt attctgggct acttttacca   2160
gatgctcagt atcctattac tgctgtgtcc cttatggaag ccttgagtgc agataagggt   2220 ggcttttat accttaacag ggtgttggtc atcctcttac agaccctcct acaagatgag   2280
atagcagaag actatggtga attgggaatg aagctgtcgg aaatccccct gactctgcat   2340
tctgtttcag agctggtgcg gctctgcttg cgcagatctg atgttcagga ggaaagcgag   2400
ggctcagaca cagatgacaa taaagattca gctgcatttg aggataatga ggtacaagat   2460
gagttcctag aaaagctgga gacctctgaa tttttgagc tgacgtcaga ggagaagcta   2520
cagatcttga cagcactgtg ccaccggatc ctcatgacat actcagtgca agaccacatg   2580
gagaccagac agcagatgtc tgcagagttg tggaaggaac ggcttgctgt gttgaaggaa   2640
```

```
gaaaatgata agaagagagc agagaaacag aaacggaaag aaatggaagc caaaaataaa    2700
gaaaatggaa aagttgagaa tgggttaggc aaaactgata ggaaaaaaga aattgtgaag    2760
tttgagcccc aagtagatac agaagctgaa gacatgatta gtgctgtgaa gagcagaagg    2820
ttgcttgcca ttcaagctaa gaaggaacgg gaaatccagg aaagagaaat gaaagtgaaa    2880
ctggaacgcc aagctgaaga agaacgaata cggaagcaca aagcagctgc tgagaaagct    2940
ttccaggaag ggattgccaa ggccaaacta gtcatgcgca ggactcctat tggcacagat    3000
cgaaaccata atagatactg gctcttctca gatgaagttc caggattatt cattgaaaaa    3060
ggctgggtac atgacagcat tgactaccga ttcaaccatc actgcaaaga ccacacagtc    3120
tctggtgatg aggattactg tcctcgcagt aagaaagcaa acttaggtaa aaatgcaagc    3180
atgaacacac aacatggaac agcaacagaa gttgctgtag agacaaccac acccaaacaa    3240
ggacagaacc tatggttttt atgtgatagt caaaaggagc tggatgagtt gctaaactgt    3300
cttcaccctc agggaataag agaaagtcaa cttaaagaga gactagagaa gaggtaccag    3360
gacattattc actctattca tctagcacgg aagccaaatt tgggtctaaa atcttgtgat    3420
ggcaaccagg agcttttaaa cttccttcgt agtgatctca ttgaagttgc aacaaggtta    3480
caaaaaggag gacttggata tgtggaagaa acatcagaat ttgaagcccg ggtcatttca    3540
ttagagaaat tgaaggattt tggtgagtgt gtgattgccc ttcaggccag tgtcataaag    3600
aaatttctcc aaggcttcat ggctcccaag caaaagagaa gaaaactcca aagtgaagat    3660
tcagcaaaaa ctgaggaagt ggatgaagag aagaaaatgg tagaggaagc aaaggttgca    3720
tctgcactgg agaaatggaa gacagcaatc cgggaagctc agactttctc caggatgcac    3780
gtgctgcttg gatgcttga tgcctgtatc aagtgggata tgtccgcaga aaatgctagg    3840
tgcaaagttt gtcgaaagaa aggtgaggat gacaaattga tcttgtgtga tgagtgtaat    3900
aaagccttcc acctgttttg tctgaggccg gccctctatg aagtaccaga tggtgagtgg    3960
cagtgcccag cttgccagcc cgctactgcc aggcgcaact cccgtggcag gaactatact    4020
gaagagtctg cttctgagga cagtgaagat gatgagagtg atgaagagga ggaggaggaa    4080
gaagaggagg aggaggaaga agattatgag gtggctggtt tgcgattgag acctcgaaag    4140
accatccggg gcaagcacag cgtcatcccc cctgcagcaa ggtcaggccg gcgcccgggt    4200
aagaagccac actctaccag gaggtctcag cccaaggcac cacctgtgga tgatgctgag    4260
gtggatgagc tggtgcttca gaccaagcgg agctcccgga ggcaaagcct ggagctgcag    4320
aagtgtgaag agatcctcca caagatcgtg aagtaccgct tcagctggcc cttcaggggag   4380 cctgtgacca gagatgaggc cgaggactac tatgatgtga tcacgcaccc catggacttt    4440
cagacagtgc agaacaaatg ttcctgtggg agctaccgct ctgtgcagga gtttcttact    4500
gacatgaagc aagtgtttac caatgctgag gtttacaact gccgtggcag ccatgtgcta    4560
agctgcatgt tgaagacaga acagtgtcta gtggctctgt tgcataaaca ccttcctggc    4620
cacccatatg tccgcaggaa gcgcaagaag tttcctgata ggcttgctga agatgaaggg    4680
gacagtgagc cagaggccgt tggacagtcc aggggacgaa gacagaagaa gtagagaggc    4740
agggccgtgg tgacagtatc agtgagtgcc atacagaatt gtgtattcac cagcatcatg    4800
aaacagttgt ggtctttga gttgatcttg gcagagtaaa gggacgtgtc ctggagccat    4860
tcctgaatct ccccttcttt gtgacagctc ctcccacccc cccaaaaaat aaaaaaacca    4920
caaaaaacaa aaaaacaaaa ctaaggcact tcacttagag actggagtcc tgcttataat    4980
```

-continued

| | |
|---|---|
| catgcatata acctttactt tgatggatct ggccagaggg gtgttggagc ccagcccacc | 5040 |
| cacataccag tcaagctctt aggggagcag aagaaaagca ggaagaattt aaatgtttaa | 5100 |
| tttttttttt aaattgactt ttctagttat taaaagttgc ttgtttcagc agtgatattg | 5160 |
| tataaagaac atcttgtaag atactcctga catcttgctt tagcacatgt acagtacagt | 5220 |
| ttctatgata atgtgtttgc tctaacttcc ctggcttctc cttcagccca tccactctcc | 5280 |
| tctagagcag ttgggttgga ggctcattga ggcaagcagc aacattggag ggggagcagg | 5340 |
| gcagtgctgt gtctgctgcc tcccatgccc gttctgacct cagccttgga actcctcaag | 5400 |
| aacctgaaga ttccagtggt cagtgtcggt ggggggtggg aggagagagc ggcagagaag | 5460 |
| ctctgagagc cccttccccc acaacaaatc tagctctagt tgttatattt aggcaaaact | 5520 |
| ttgtagtctt ctttcccttt tatgatggat tttgataaaa gtacaaaaca gggttttttct | 5580 |
| tttttatcac ctttgaattt ggaaattttg agcacccaag ctcttctgta cctatttaaa | 5640 |
| gtccaccaag gggactgcag ctcctagaac atgagaatca agcctcttaa ttttaaactg | 5700 |
| cggaatgtgg cctctgcttc ctccgtcctc ctgcccaagg acgacgagga ttgctccagg | 5760 |
| gctgctgggt agtttaccgt cccttctata ggcatggagt tggcactgac atcacagctt | 5820 |
| cataaccccca ccaccgccag cttcccctgc ctcctacatc cagtctgttc ttgttcatag | 5880 |
| tgagaatcct gtgttcccac ttcagtgaca cctgaattgt ttgttgttgt tttttttttt | 5940 |
| tattgtcttc aaagaggaag ggccccatta aagggtgaac ttgtaataaa ttggaatttc | 6000 |
| aaataaacct catgtacttg tgtttataaa gaagaaacca ctctgaaaaa aaaaaaaaa | 6060 |
| aaa | 6063 |

<210> SEQ ID NO 5
<211> LENGTH: 1690
<212> TYPE: DNA
<213> ORGANISM: Homo sapient

<400> SEQUENCE: 5

| | |
|---|---|
| cgggcccggt agctgggccc gcgtccgccg cccgcatccc cgcgccgccg catctcctcg | 60 |
| ccgcctcccg ggcttcggac ccccggtctc gcccccgaaa catgactcgc gatttcaaac | 120 |
| ctggagacct catcttcgcc aagatgaaag gttatcccca ttggccagct cgagtagacg | 180 |
| aagttcctga tggagctgta aagccaccca caaacaaact acccattttc tttttttggaa | 240 |
| ctcatgagac tgcttttta ggaccaaagg atatatttcc ttactcagaa aataaggaaa | 300 |
| agtatggcaa accaaataaa agaaaaggtt taatgaagg tttatgggag atagataaca | 360 |
| atccaaaagt gaaattttca agtcaacagg cagcaactaa acaatcaaat gcatcatctg | 420 |
| atgttgaagt tgaagaaaag gaaactagtg tttcaaagga agataccgac catgaagaaa | 480 |
| aagccagcaa tgaggatgtg actaaagcag ttgacataac tactccaaaa gctgccagaa | 540 |
| gggggagaaa gagaaaggca gaaaaacaag tagaaactga ggaggcagga gtagtgacaa | 600 |
| cagcaacagc atctgttaat ctaaaagtga gtcctaaaag gacgacct gcagctacag | 660 |
| aagtcaagat tccaaaacca agaggcagac ccaaaatggt aaaacagccc tgtccttcag | 720 |
| agagtgacat cattactgaa gaggacaaaa gtaagaaaaa ggggcaagag gaaaacaac | 780 |
| ctaaaaagca gcctaagaag gatgaagagg gccagaagga agaagataag ccaagaaaag | 840 |
| agccggataa aaaagagggg aagaagaag ttgaatcaaa aaggaaaaat ttagctaaaa | 900 |
| caggggttac ttcaacctcc gattctgaag aagaaggaga tgatcaagaa ggtgaaaaga | 960 |
| agagaaaagg tgggaggaac tttcagactg ctcacagaag gaatatgctg aaaggccaac | 1020 |

```
atgagaaaga agcagcagat cgaaaacgca agcaagagga acaaatgaa actgagcacc    1080 aaacaacatg taatctacag taataaaaaa tatatctcat tttgggctca agcattaat    1140 ccagttactg aaaagagaat acaagtggag caaacaagag atgaagatct tgatacagac    1200
tcattggact gaatttcccc cttcccccca ttgatggaag aatgttccag attctaaatt    1260
gaggacttca ttattaatgg cattactgtg ttatgattaa caaatttcct gtaaggtaca    1320
cactacatac taaggtcggc catcattcct gttttttttt ttttttttt tttttaacca    1380 agcttaaaat gaagctttgt gtttgaaagt aataacaagc tcagacgaag atggtggttg    1440
tacattattc atctagaaaa tataaaaatt cattttgttt tgaagctagt tattaaactg    1500
gaatagcagt tatatccctg agaatggggc ccttctcttg acattccttt gttgtttaat    1560
tctttagaat cttaataaat gttttttaa tcctgagaga ttaaacagta gtagacttgt    1620
taagaatgaa actgtaacca aaattttaaa ataaagtttt ttttaaaaaa aaaaaaaaa    1680 aaaaaaaaa                                                           1690
```

<210> SEQ ID NO 6
<211> LENGTH: 3408
<212> TYPE: DNA
<213> ORGANISM: Homo sapiens

<400> SEQUENCE: 6

```
cctttggacg cgcgcctcgg ttccgaacgc agcggacggc gcctcaggca gcgcggcgga     60
cagcccgtcc tccggcgcgc cgcgagcctc ggaggaccct agcgacggtc gtggcgtaag    120
accgggggga cgcggcggta gcggcggccg ttgcgattga ttgcgctggt tgcctgcggc    180
gtccacttcc ttggccgccc ttgctacact ggctgattgt tgtgcagccg cgcgccatgtc    240 tgtgagcgag atcttcgtgg agctgcaggg ctttttggct gccgagcagg acatccgaga    300
ggaaatcaga aaagttgtac agagtttaga caaacagct cgagagattt taactctact    360
gcaaggggtc catcagggtg ctgggtttca ggacattcca aagaggtgtt tgaaagctcg    420
agaacatttt ggtacagtaa aaacacatct aacatctttg aagaccaaat ttcctgctga    480
acagtattac agatttcatg agcactggag gtttgtgttg cagcgcttgg tcttcttggc    540
agcatttgtt gtgtatttgg aaacagaaac actagtgact cgagaagcag ttacagaaat    600
tcttggcatt gagccagatc gggagaaagg atttcatctg gatgtagaag attatctctc    660
aggagttcta attcttgcca gtgaactgtc gaggctgtct gtcaacagcg tgactgctgg    720
agactactcc cgaccctcc acatctccac cttcatcaat gagctggatt ccggttttcg    780
ccttctcaac ctgaaaaatg actccctgag gaagcgctac gacggattga atatgacgt    840 gaagaaagta gaggaagtgg tctatgatct ctccatccgg ggctttaata aggagacggc    900
agcagcttgt gttgaaaaat aggaggctct ccttgctcct ggccttgctg acctcagcgg    960
ttgccaggaa ggggtgagca cagagtgcct cttacggtag ttaggatgct cagttgctaa    1020
acactgcgct ttatttttctt aaccagttgt ggtgtgagta tcagaattga aacacttttt    1080
tgggggtaaa aaatatagcc tttacatgga cagaattttt tttgttgttt cagtgaatat    1140
gcctgtaatt cagtgtattt cagttccgtc agaaagtgta aatgttagtt tcttggtaaa    1200
gtccttttct tgcttacctt gactgttgat gtactgattg agaagttcat tgtctcgttt    1260
gtgattcttc cagatgtgat gcttgatatt ttctatatgc gagttagcca tccacaccca    1320
ggcatagcct ggatacagta taaaaataga taattaaaaa gatggttgcc aagcaaggaa    1380
```

```
aacttattt  atattttccc  ttccttattt  taagcattgt  gagtaaatca  gatgttgaat     1440
tcttttgcca  agggaattat  agctgcaggt  tctctctcac  tgccatcaaa  ctgtaaaaga     1500
ttaaactgcg  aagtcaagct  caacagatta  ttttggaaag  ttttgtatt  aagggattta     1560 gtaacatcat  tttgttttcc  accaggcagg  gagtagggct  tagtgtttta  aaacacctct     1620
gctttctgat  gttgccttaa  tattctgcta  ttgcagcaat  taaaaattgt  cttcatgtac     1680
atttggaact  aacacgtgat  gtgatatatt  cctaaactat  gaaaccttt  tcctagtagt     1740 cagctagatc  atttgttctg  ggagtataaa  gccacccacg  taagttaata  agcaaaatcc     1800
tgactattat  gttgttagag  aaaaatgctt  tgctttgtct  ggaagaaaga  taaaatagtg     1860
aattataaat  aagtcaggcc  gggcgtggtg  gctcacacct  gtaatcccag  cacactggga     1920
ggccgaggca  gggggactgc  ttgagctcag  gagttcgaga  ccagcctggg  caacaaagtg     1980
agactccatc  tctatataaa  aacaaaaacc  acgaaagcac  acacaaaata  aatcagtggg     2040
atttggtaat  gtgttttaga  gtaagaaatt  tcaggttgtt  ggtgactatc  ccaacagtca     2100
tgttttaaat  gtacagtttg  gggcaagtca  tgtaaatact  gttggtggtc  ttccccacac     2160
gccccaattt  tcaggtagta  ctaagagtat  gtgccaggaa  actcttgcta  ttgaattgag     2220
atgattaaaa  tggtgactta  atccgtagtt  attttgcacc  cactgaaagg  aaagtgcttt     2280
ccagaataat  atgaagtatc  taaaagtgtc  accttttctt  gcctgatcaa  caatttgggc     2340
ttcctgtttg  tacaagggc  catttggcat  acctttcaca  gcttttatca  ggccaagtta     2400
aaggctgact  acatttttc  atcatgagga  aagcagttga  aatgaggcat  gagttactgt     2460
gcattgggat  tttagaacaa  ttttcttgtg  acagctcttt  ttgtgaagtt  aggttcttaa     2520
aagtgcccat  gatggtcact  taaaatgtgc  agtaatagca  ctgccaggat  caagcatgaa     2580
aggcttttaa  attagatcat  cccacagaca  atacgtttga  taatagtttt  ttcttttaac     2640
ctctttaagt  attgattctg  cttgagaata  ttgaagtact  tgccagaagt  tgtggatttc     2700
agttttaaca  aatgctatta  aagtggagaa  gcacactctg  gtcttggaat  tccatttgag     2760
gatttagaag  tgtcatgttt  ataactattc  agttgtgttt  gttgctggct  tgttgtaaag     2820
caataaaatt  ttttggtct  ttttgtaagt  gagtgtgctg  ctgtaagaaa  tctcccatgt     2880
gcataacaaa  ttctgaatat  ttttgaggc  taaagaagac  cggggtgaca  agcagatact     2940
gctgtgtaat  ggttacacta  accaaaagac  accagccact  cagagttcta  tactgtaaag     3000
cgcagataac  atttgtgtgt  tataccttga  ttggggaatt  aaaagtcatt  taactgaaga     3060
tgttgagaaa  cctgggctct  ggttttagta  taccggaatt  acttttttcc  aattttagaa     3120
aatcaagcag  gttagagaaa  atagagatga  attagggac  actgtcttat  ggattcattt     3180
ataagaagag  aaccagccat  atacacttgg  ggagatttgc  cacatcttaa  acttgaataa     3240
tagtatgagt  aatgcttaag  ggagtttaat  agagaaggaa  agctttggca  gtgttttgag     3300
aacttaagtg  gctaaagaga  tgagacaaac  atgcaggtcg  ctactggcat  agtttcataa     3360
ttgtgtactc  ggaaattaaa  gtttgcttgt  ttccttggtct  ggattaaa                  3408
```

<210> SEQ ID NO 7
<211> LENGTH: 20
<212> TYPE: DNA
<213> ORGANISM: homo sapiens

<400> SEQUENCE: 7

```
tcgtacaagt tgtcggccag                                                      20
```

```
<210> SEQ ID NO 8
<211> LENGTH: 20
<212> TYPE: DNA
<213> ORGANISM: Homo sapiens

<400> SEQUENCE: 8
cagattagta ggcggcttga                                               20

<210> SEQ ID NO 9
<211> LENGTH: 20
<212> TYPE: DNA
<213> ORGANISM: Homo sapiens

<400> SEQUENCE: 9
tacccagaac atagacacgc                                               20

<210> SEQ ID NO 10
<211> LENGTH: 20
<212> TYPE: DNA
<213> ORGANISM: Homo sapiens

<400> SEQUENCE: 10
gagttctgag tggtaatcga                                               20

<210> SEQ ID NO 11
<211> LENGTH: 20
<212> TYPE: DNA
<213> ORGANISM: Homo sapiens

<400> SEQUENCE: 11
ggtactcggg tccgtcccga                                               20

<210> SEQ ID NO 12
<211> LENGTH: 20
<212> TYPE: DNA
<213> ORGANISM: Homo sapiens

<400> SEQUENCE: 12
gagtagcgcg agcacagcta                                               20

<210> SEQ ID NO 13
<211> LENGTH: 20
<212> TYPE: DNA
<213> ORGANISM: Homo sapiens

<400> SEQUENCE: 13
cctgaatctt tggagtacgc                                               20

<210> SEQ ID NO 14
<211> LENGTH: 20
<212> TYPE: DNA
<213> ORGANISM: Homo sapiens

<400> SEQUENCE: 14
agtatgaagc ccgcttggaa                                               20

<210> SEQ ID NO 15
<211> LENGTH: 20
<212> TYPE: DNA
<213> ORGANISM: Homo sapiens

<400> SEQUENCE: 15
atttggacgt gcaagagtac                                               20
```

```
<210> SEQ ID NO 16
<211> LENGTH: 20
<212> TYPE: DNA
<213> ORGANISM: Homo sapiens

<400> SEQUENCE: 16
aacggcttca ccagcgggaa                                              20

<210> SEQ ID NO 17
<211> LENGTH: 20
<212> TYPE: DNA
<213> ORGANISM: Homo sapiens

<400> SEQUENCE: 17
aaaggtacag tgagcgcatt                                              20

<210> SEQ ID NO 18
<211> LENGTH: 20
<212> TYPE: DNA
<213> ORGANISM: Homo sapiens

<400> SEQUENCE: 18
ggtttcaccg agacctcagt                                              20

<210> SEQ ID NO 19
<211> LENGTH: 20
<212> TYPE: DNA
<213> ORGANISM: Homo sapiens

<400> SEQUENCE: 19
ggacacctcg gcccttgagc                                              20

<210> SEQ ID NO 20
<211> LENGTH: 20
<212> TYPE: DNA
<213> ORGANISM: Homo sapiens

<400> SEQUENCE: 20
ggacacctcg gcccttgagc                                              20

<210> SEQ ID NO 21
<211> LENGTH: 20
<212> TYPE: DNA
<213> ORGANISM: Homo sapiens

<400> SEQUENCE: 21
aaaagagccg gataaaaaag                                              20

<210> SEQ ID NO 22
<211> LENGTH: 20
<212> TYPE: DNA
<213> ORGANISM: Homo sapiens

<400> SEQUENCE: 22
tcctttagaa acttgtcccg                                              20

<210> SEQ ID NO 23
<211> LENGTH: 20
<212> TYPE: DNA
<213> ORGANISM: Homo sapiens

<400> SEQUENCE: 23
ggatgaaggc tgggtacctt                                              20
```

```
<210> SEQ ID NO 24
<211> LENGTH: 20
<212> TYPE: DNA
<213> ORGANISM: Homo sapiens

<400> SEQUENCE: 24
tgaaatcctt tctcccgatc                                               20

<210> SEQ ID NO 25
<211> LENGTH: 20
<212> TYPE: DNA
<213> ORGANISM: Homo sapiens

<400> SEQUENCE: 25
aacctgtaat actgttcagc                                               20

<210> SEQ ID NO 26
<211> LENGTH: 20
<212> TYPE: DNA
<213> ORGANISM: Homo sapiens

<400> SEQUENCE: 26
ctctgcttct tcatcgccct                                               20

<210> SEQ ID NO 27
<211> LENGTH: 20
<212> TYPE: DNA
<213> ORGANISM: Homo sapiens

<400> SEQUENCE: 27
atccgtggcc catcatgtct                                               20
```

ARGININE AND ITS USE AS A T CELL MODULATOR

This application is a national stage application under 35 U.S.C. § 371 of PCT International Application No. PCT/EP2017/076123, which has an international filing date of 12 Oct. 2017 and claims priority under 35 U.S.C. § 119 to EP 16193598.6 filed on 12 Oct. 2016. The contents of each application recited above are incorporated herein by reference in their entirety.

The present invention relates to the field of T cell based immunotherapies and specifically to novel uses and methods for modulating T cell function and activity.

The immune system of multicellular organisms has evolved as a guard against foreign infections that threaten host survival. T cells recognize foreign antigens derived from infective pathogens via their T cell receptor and effectively direct immune responses leading to destruction of the pathogens and/or infected cells. The finding that T cells are capable of recognizing tumor-associated antigens (TAA) and mediating anti-tumor responses has sparked the interest to exploit the intrinsic defense mechanisms of the immune system to combat not only infection but also cancer. T cells have numerous advantageous properties making them promising tools for immunotherapy: T cell responses are specific, and can thus be specifically directed at infected or cancerous cells; 2) T cells responses are robust, undergoing up to 1,000-fold clonal expansion after activation; 3) T cell response can traffic to the site of antigen, and eradicate infected or cancerous cells at distant parts of the body; and 4) T cell responses have memory, and are thus capable of maintaining a therapeutic effect for many years after initial treatment.

There have been various approaches for successfully establishing strategies for T cell-based immunotherapies. Although the basic principles mediating T cell immunity have been resolved, ongoing research is still trying to elucidate the complex underlying mechanisms regulating T cell function and activity. Upon antigenic stimulation, antigen-specific naive T cells proliferate extensively and acquire different types of effector functions. To support cell growth and proliferation, activated T cells adapt their metabolism to ensure the generation of sufficient biomass and energy (Fox et al., 2005). Unlike quiescent T cells, which require little nutrients and mostly use oxidative phosphorylation (OX-PHOS) for their energy supply, activated T cells consume large amounts of glucose, amino acids and fatty acids and adjust their metabolic pathways towards increased glycolytic and glutaminolytic activity (Blagih et al., 2015; Rolf et al., 2013; Sinclair et al., 2013; Wang et al., 2011).

At the end of the immune response, most T cells undergo apoptosis, while a few survive as memory T cells that confer long-term protection (Kaech and Cui, 2012; Sallusto et al., 2010). T cell survival is regulated by extrinsic and intrinsic factors. Prolonged or strong stimulation of the T cell receptor (TCR) of $CD4^+$ and $CD8^+$ T cells promotes 'fitness' by enhancing survival and responsiveness to the homeostatic cytokines IL-7 and IL-15, which in turn sustain expression of anti-apoptotic proteins (Gett et al., 2003; Schluns and Lefrancois, 2003; Surh et al., 2006). Metabolic activity is also critical to determine T cell fate and memory formation (MacIver et al., 2013; Pearce et al., 2013; Wang and Green, 2012). For instance, triglyceride synthesis is central in IL-7-mediated survival of memory $CD8^+$ ET cells (Cui et al., 2015), while increased mitochondrial capacity endows T cells with a bioenergetic advantage for survival and recall responses (van der Windt et al., 2012). Mitochondrial fatty acid oxidation is required for the generation of memory T cells (Pearce et al., 2009), while mTOR, a central regulator of cell metabolism, has been shown to control T cell memory formation (Araki et al., 2009).

Albeit T cell based immunotherapies have a huge potential as a tool for personalized and effective treatment of a variety of conditions—including cancer and infections, still some of the leading causes of death world-wide—a key problem that currently limits therapeutic application is the short persistence of antigen-specific T cells in the patient. Adoptive T cell therapy (ACT) approaches are still seriously hampered by the fact that T cells harnessed with highly antigen-specific T cell receptors ex vivo are rapidly cleared from the body after re-introduction into the patient. The factors regulating T cell clearance and apoptosis in the treated patient are still not completely understood. T cell based immunotherapies therefore often rely on the administration of cytokines or other (co-)stimulatory molecules in order to promote T cell survival and persistence—which however bears the risk of severe side effects in the treated patient.

In view of the above, it is the object of the present invention to overcome the drawbacks of current T cell based immunotherapies outlined above and to provide novel strategies for exploiting T cell immunity and particularly facilitating adoptive T cell therapy (ACT).

Although the present invention is described in detail below, it is to be understood that this invention is not limited to the particular methodologies, protocols and reagents described herein as these may vary. It is also to be understood that the terminology used herein is not intended to limit the scope of the present invention which will be limited only by the appended claims. Unless defined otherwise, all technical and scientific terms used herein have the same meanings as commonly understood by one of ordinary skill in the art.

In the following, the elements of the present invention will be described. These elements are listed with specific embodiments, however, it should be understood that they may be combined in any manner and in any number to create additional embodiments. The variously described examples and preferred embodiments should not be construed to limit the present invention to only the explicitly described embodiments. This description should be understood to support and encompass embodiments which combine the explicitly described embodiments with any number of the disclosed and/or preferred elements. Furthermore, any permutations and combinations of all described elements in this application should be considered disclosed by the description of the present application unless the context indicates otherwise.

Throughout this specification and the claims which follow, unless the context requires otherwise, the term "comprise", and variations such as "comprises" and "comprising", will be understood to imply the inclusion of a stated member, integer or step but not the exclusion of any other non-stated member, integer or step. The term "consist of" is a particular embodiment of the term "comprise", wherein any other non-stated member, integer or step is excluded. In the context of the present invention, the term "comprise" encompasses the term "consist of". The term "comprising" thus encompasses "including" as well as "consisting" e.g., a composition "comprising" X may consist exclusively of X or may include something additional e.g., X+Y.

The terms "a" and "an" and "the" and similar reference used in the context of describing the invention (especially in the context of the claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. No language in the specification should be construed as indicating any non-claimed element essential to the practice of the invention.

The word "substantially" does not exclude "completely" e.g., a composition which is "substantially free" from Y may be completely free from Y. Where necessary, the word "substantially" may be omitted from the definition of the invention.

The term "about" in relation to a numerical value x means x±10%.

The present inventors took advantage of recent developments in mass spectrometry to obtain dynamic proteome and metabolome profiles of human primary naïve T cells following activation and found several changes in metabolic pathways. Surprisingly, the inventors found that L-arginine is avidly taken up by activated T cells in amounts exceeding the requirements for protein synthesis, and controls glycolysis and mitochondrial activity. Strikingly, the inventors further discovered that L-arginine—presumably by interacting with or acting on the transcriptional regulators BAZ1B, PSIP1 and TSN—increases the survival of both activated CD4$^+$ and CD8$^+$ T cells and fosters the generation of central memory-like T ($T_{CM}$) cells with enhanced anti-tumor activity in a mouse model. Knockout of the transcriptional regulators BAZ1B, PSIP1 and TSN significantly reduced the beneficial effect of L-arginine on T cell survival, suggesting that BAZ1B, PSIP1 and TSN are pivotal inducers of the pro-survival program of activated T cells. In consequence, L-arginine and (other) ligands of BAZ1B, PSIP1 and/or TSN are considered promising tools for modulating various T cell responses and effector functions. L-arginine and (other) ligands of BAZ1B, PSIP1 and/or TSN are therefore attributed a central role in developing novel T cell based immunotherapies.

In a first aspect, the present invention therefore features a BAZ1B, PSIP1 and/or TSN ligand ("BPT ligand") for use in a method of modulating a T cell mediated immune response in a subject. A preferred BPT ligand of the invention is L-arginine. Accordingly, the present invention further provides L-arginine for use in a method of modulating a T cell mediated immune response in a subject. Said T cell mediated immune response is preferably enhanced. Said modulated or preferably enhanced T cell mediated immune response is preferably a T cell mediated anti-cancer response or a T cell mediated anti-infection response.

It should thus be acknowledged that the disclosure of the present invention relates to both BPT ligands (L-arginine being a preferred BPT ligand in accordance with the invention) and to L-arginine as such, i.e. irrespective of its mechanism of action on or interaction with BAZ1B, PSIP1 and/or TSN. Thus, throughout the present application the expression "L-arginine or (other) BPT ligands" is used to refer to (i) L-arginine irrespective of its mechanism of action (ii) L-arginine as a BPT ligand and/or (iii) (other) BPT ligands (different from L-arginine).

BAZ1B, PSIP1 and TSN

As discussed above, the present inventors reported for the first time that L-arginine is capable of effectively enhancing T cell survival and effector functions. The conducted experiments show that the transcriptional regulators BAZ1B, PSIP1 and TSN are capable of sensing intracellular L-arginine concentrations and—in response to increased L arginine levels—mediate favorable T cell responses in vitro and in vivo. BAZ1B, PSIP1 and TSN are expressed ubiquitously in the nucleus of many cell types, including T cells. As demonstrated in the appended Examples, different T cells (such as CD4+ and CD8+) are responsive to increased levels of L-arginine or (other) BPT ligands and therefore constitute promising targets for L-arginine or (other) BPT ligands in a variety of in vitro, ex vivo and in vivo applications.

The terms "protein" and "polypeptide" are used interchangeably herein to refer to (macro) molecules comprising at least two amino acids joined to each other by a peptide bond. When referring to BAZ1B, PSIP1 and/or TSN, the term "protein" or "polypeptide" preferably refers to the protein products encoded by the respective human wild-type genes indicated herein or allelic variants or orthologs thereof. An "allelic variant" is an alternative form of the same gene occupying a given position, or locus, on a chromosome. An "ortholog" is a homologous ("corresponding") gene found in different species.

The term "BAZ1B" (Bromodomain Adjacent To Zinc Finger Domain 1B) as used herein refers to the protein product of the human BAZ1B gene (NCBI Gene ID: 9031) or an allelic variant or ortholog thereof. It particularly refers to the "BAZ1B tyrosine-protein kinase" (UniProt Acc. No. Q9UIG0; entry version #163, sequence version #2 last modified Aug. 30, 2002) comprising or consisting of an amino acid sequence as depicted in SEQ ID NO: 1 below.

SEQ ID NO: 1

MAPLLGRKPFPLVKPLPGEEPLFTIPHTQEAFRTREEYEARLERYSERIW

TCKSTGSSQLTHKEAWEEEQEVAELLKEEFPAWYEKLVLEMVHHNTASLE

KLVDTAWLEIMTKYAVGEECDFEVGKEKMLKVKIVKIHPLEKVDEEATEK

KSDGACDSPSSDKENSSQIAQDHQKKETVVKEDEGRRESINDRARRSPRK

LPTSLKKGERKWAPPKFLPHKYDVKLQNEDKIISNVPADSLIRTERPPNK

EIVRYFIRHNALRAGTGENAPWVVEDELVKKYSLPSKESDELLDPYKYMT

LNPSTKRKNTGSPDRKPSKKSKTDNSSLSSPLNPKLWCHVHLKKSLSGSP

LKVKNSKNSKSPEEHLEEMMKMMSPNKLHTNFHIPKKGPPAKKPGKHSDK

PLKAKGRSKGILNGQKSTGNSKSPKKGLKTPKTKMKQMTLLDMAKGTQKM

TRAPRNSGGTPRTSSKPHKHLPPAALHLIAYYKENKDREDKRSALSCVIS

KTARLLSSEDRARLPEELRSLVQKRYELLEHKKRWASMSEEQRKEYLKKK

REELKKKLKEKAKERREKEMLERLEKQKRYEDQELTGKNLPAFRLVDTPE

GLPNTLFGDVAMVVEFLSCYSGLLLPDAQYPITAVSLMEALSADKGGFLY

LNRVINILLQTLLQDEIAEDYGELGMKLSEIPLTLHSVSELVRLCLRRSD

VQEESEGSDTDDNKDSAAFEDNEVQDEFLEKLETSEFFELTSEEKLQILT

ALCHRILMTYSVQDHMETRQQMSAELWKERLAVLKEENDKKRAEKQKRKE

MEAKNKENGKVENGLGKTDRKKEIVKFEPQVDTEAEDMISAVKSRRLLAI

QAKKEREIQEREMKVKLERQAEEERIRKHKAAAEKAFQEGIAKAKLVMRR

TPIGTDRNHNRYWLFSDEVPGLFIEKGWVHDSIDYRFNHHCKDHTVSGDE

DYCPRSKKANLGKNASMNTQHGTATEVAVETTTPKQGQNLWFLCDSQKEL

DELLNCLHPQGIRESQLKERLEKRYQDIIHSIHLARKPNLGLKSCDGNQE

LLNFLRSDLIEVATRLQKGGLGYVEETSEFEARVISLEKLKDFGEOVIAL

-continued

```
QASVIKKFLQGFMAPKQKRRKLQSEDSAKTEEVDEEKKMVEEAKVASALE

KWKTAIREAQTFSRMHVLLGMLDACIKWDMSAENARCKVCRKKGEDDKLI

LCDECNKAFHLFCLRPALYEVPDGEWQCPACQPATARRNSRGRNYTEESA

SEDSEDDESDEEEEEEEEEEEEEDYEVAGLRLRPRKTIRGKHSVIPPAAR

SGRRPGKKPHSTRRSQPKAPPVDDAEVDELVLQTKRSSRRQSLELQKCEE

ILHKIVKYRFSWPFREPVTRDEAEDYYDVITHPMDFQTVQNKCSCGSYRS

VQEFLTDMKQVFTNAEVYNCRGSHVLSCMVKTEQCLVALLHKHLPGHPYV

RRKRKKFPDRLAEDEGDSEPEAVGQSRGRRQKK
```

BAZ1B is known as a transcriptional regulator containing a PHD-type zinc finger domain that supposedly binds to methylated histones. It has been suggested to play a role in chromatin remodeling. The term "BAZ1B" encompasses proteins comprising or consisting of the amino acid sequence depicted in SEQ ID NO: 1 or isoforms or functional variants thereof comprising or consisting of an amino acid sequence which is at least 75%, preferably at least 80%, preferably at least 85%, preferably at least 90%, more preferably at least 95%, more preferably at least 96%, more preferably at least 97%, more preferably at least 98%, most preferably at least 99% or most preferably 100% identical to SEQ ID NO: 1.

The term "PSIP1" as used herein refers to the protein product of the human PISP1 gene (NCBI Gene ID: 11168) or an allelic variant or ortholog thereof. It particularly refers to the "PC4 and SERS1-interacting protein" (UniProt Acc. No. O75475; entry version #155, sequence version #1 last modified Nov. 1, 1998) comprising or consisting of an amino acid sequence as depicted in SEQ ID NO: 2 below.

```
                                          SEQ ID NO: 2
MTRDFKPGDLIFAKMKGYPHWPARVDEVPDGAVKPPTNKLPIFFFGTHET

AFLGPKDIFPYSENKEKYGKPNKRKGENEGLWEIDNNPKVKFSSQQAATK

QSNASSDVEVEEKETSVSKEDTDHEEKASNEDVTKAVDITTPKAARRGRK

RKAEKQVETEEAGVVTTATASVNLKVSPKRGRPAATEVKIPKPRGRPKMV

KQPCPSESDIITEEDESKKKGQEEKQPKKQPKKDEEGQKEEDKPRKEPDK

KEGKKEVESKRKNLAKTGVTSTSDSEEEGDDQEGEKKRKGGRNFQTAHRR

NMLKGQHEKEAADRKRKQEEQMETEQQNKDEGKKPEVKKVEKKRETSMDS

RLQRIHAEIKNSLKIDNLDVNRCIEALDELASLQVTMQQAQKHTEMITTL

KKIRRFKVSQVIMEKSTMLYNKFKNMFLVGEGDSVITQVLNKSLAEQRQH

EEANKTKDQGKKGPNKKLEKEQTGSKTENGGSDAQDGNQPQHNGESNEDS

KDNHEASTKKKPSSEERETEISLKDSTLDN
```

PSIP1 is known as a transcriptional co-activator and has been attributed a role in coordinating pre-mRNA splicing. The term "PSIP1" encompasses proteins comprising or consisting of the amino acid sequence depicted in SEQ ID NO: 2 or isoforms or functional variants thereof comprising or consisting of an amino acid sequence which is at least 75%, preferably at least 80%, preferably at least 85%, preferably at least 90%, more preferably at least 95%, more preferably at least 96%, more preferably at least 97%, more preferably at least 98%, most preferably at least 99% or most preferably 100% identical to SEQ ID NO: 2.

The term "TSN" as used herein refers to the protein product of the human TSN gene (NCBI Gene ID: 7247) or an allelic variant or ortholog thereof. It particularly refers to the "Translin" protein (UniProt Acc. No. Q15631; entry version #145, sequence version #1 last modified Nov. 1, 1996) comprising or consisting of an amino acid sequence as depicted in SEQ ID NO: 3 below.

```
SEQ ID NO: 3:
MSVSEIFVELQGFLAAEQDIREEIRKVVQSLEQTAREILTLLQGVHQGAG

FQDIPKRCLKAREHFGTVKTHLTSLKTKFPAEQYYRFHEHWRFVLQRLVF

LAAFVVYLETETLVTREAVTEILGIEPDREKGFRLDVEDYLSGVLILASE

LSRLSVNSVTAGDYSRPLHISTFINELDSGFRLLNLKNDSLRKRYDGLKY

DVKKVEEVVYDLSIRGFNKETAAACVEK
```

TSN is a small DNA and RNA binding protein that is reportedly involved in DNA repair, regulation of mRNA expression and RNA interference. The term "TSN" encompasses proteins comprising or consisting of the amino acid sequence depicted in SEQ ID NO: 3 or isoforms or functional variants thereof comprising or consisting of an amino acid sequence which is at least 75%, preferably at least 80%, preferably at least 85%, preferably at least 90%, more preferably at least 95%, more preferably at least 96%, more preferably at least 97%, more preferably at least 98%, most preferably at least 99% or most preferably 100% identical to SEQ ID NO: 3.

"Isoforms" are generally to be understood as proteins or polypeptides encoded by the same gene (or an allelic variant thereof located at the same position, or genetic locus, on a chromosome) but being different e.g. in terms of chemistry, activity, localization, interaction, conformation and/or amino acid sequence. Isoforms can emerge from variations in the protein-encoding gene sequences. Many genetic variations occur in non-coding regions of the genome or do not result in a change in amino acid sequence of the encoded protein ("silent mutation"), but some affect the amino acids in the protein-coding parts of a particular gene. Such genetic variations can result in substitutions, insertions, additions and/or deletions of amino acid residues in a protein sequence. It will therefore be acknowledged that the terms "isoform" and "sequence variant" may overlap to some extent. Isoforms can also result from post-translational modifications (PTM) resulting, e.g., in covalent modifications of a given protein. Common post-translational modifications include glycosylation, phosphorylation, ubiquitinylation, S-nitrosylation, methylation, N-acetylation, lipidation, disulfide bond formation, sulfation, acylation, deamination etc., alternative splicing (by exon skipping, use of alternative donor or acceptor sites or intron retention) or proteolytic cleavage. Whether resulting from genetic variations or PTMs, proteins encompassed by the term "isoform" as used herein preferably exhibit the same biological function as their canonical counterparts, (which are typically the most prevalent isoforms)—e.g. BAZ1B as depicted in SEQ ID NO: 1; PSIP1 as depicted in SEQ ID NO: 2 and TSN as depicted in SEQ ID NO: 3.

The term "sequence variant" or "variant" as used herein refers to polypeptides or polynucleotides comprising an altered sequence as compared to a "reference" (or "parent") sequence, i.e. for instance one of the polynucleotide sequences shown in SEQ ID NO: 1-3 or one of the polynucleotide sequences shown in SEQ ID NO: 4-6. The sequence variant can be derived from, isolated from, related to, based on or homologous to the parent sequence. A sequence variant is termed "functional" if it retains the desired biological function (or activity) of the reference (or parent) sequence. For instance, functional variants of BAZ1B, PSIP1 or TSN are still capable of modulating T cell function in a manner that is comparable to the reference proteins evaluated in the appended examples. Sequence variants also include fragments (portions or subsequences) of a reference sequence. A sequence variant can have 100% sequence identity with the reference (parent) sequence, or alternatively, can have less than 100% sequence identity with the reference (parent) sequence. In particular, a sequence variant is envisaged to comprise at least one amino acid or nucleotide deletion, substitution or insertion as compared to the reference (parent) sequence. As a result of the alterations, the sequence variant has a sequence which is at least 75%, preferably at least 80%, preferably at least 85%, preferably at least 90%, more preferably at least 95%, more preferably at least 96%, more preferably at least 97%, more preferably at least 98%, most preferably at least 99% or most preferably 100% identical to the reference sequence, whereby sequence identity is calculated as described below. Sequence variants include sequences comprising the entire parent sequence, and further comprising additional fused sequences.

In the context of the present invention, a reference sequence (e.g. any one of the sequences shown in SEQ ID NO: 1-6 herein) "sharing a sequence identity" of at least, for example, 95% to a sequence variant (e.g. identifying a sequence variant of any one of the sequences shown in SEQ ID NO: 1-6 herein), is intended to mean that the sequence of the sequence variant is identical to the reference sequence except that the sequence variant may include up to five alterations per each 100 amino acids or nucleotides of the query sequence. In other words, to obtain a sequence having a sequence of at least 95% identity to a reference sequence, up to 5% (5 of 100) of the amino acid residues or nucleotides in the sequence variant may be deleted or substituted or up to 5% of the amino acid residues or nucleotides in the sequence variant may be added or inserted The "% identity" of two amino acid sequences or two nucleic acid sequences can be or is generally determined by aligning the sequences for optimal comparison purposes (e.g., gaps can be introduced in either sequences for best alignment with the other sequence) and comparing the nucleotides at corresponding positions. The "best alignment" is an alignment of two sequences that results in the highest percent identity. The percent identity is determined by the number of identical nucleotides in the sequences being compared (i.e., % identity=# of identical positions/total # of positions×100). The determination of percent identity between two sequences can be accomplished using a mathematical algorithm known to those of skill in the art.

Ligands

The present inventors identified BPT ligands and in particular L-arginine as potent modulators of T cell function.

The term "ligand" refers to a molecule that can specifically bind to its target (e.g. BAZ1B, PSIP1 and/or TSN) and upon binding preferably modulates a biological function or activity of its target. The term "biological function" (or "biological activity") is used herein to refer to the desired effect mediated by an entity in a biological (for instance, without limitation, in its natural or native) environment. When referring to T cells, the term "T cell function" or "T cell response" is used herein to refer to the biological function of a T cell. The term "effector function" is used to refer to desirable (therapeutic) effect of a T cell on a target cell, which can e.g. be another immune cell or a cancer cell or infected cell.

The term "ligand" may also include encompasses a molecule capable of specifically modulating the biological function of its respective target molecule upon binding to a different (or "intermediate") target molecule (e.g. different from BAZ1B, PSIP1 and/or TSN). In other words, in said aspects the term "ligand" encompasses in particular directly binding ligands as well as indirectly binding ligands. In this regard, a "directly binding" ligand means a ligand capable of specifically modulating the biological function of its target by directly interacting with said target (e.g. BAZ1B, PSIP1 and/or TSN). An "indirectly binding" ligand means a ligand capable of specifically modulating the biological function of its target by interacting with a different ("intermediate") target which in turn acts on the target (e.g. BAZ1B, PSIP1 and/or TSN) as such.

L-arginine and (other) BPT ligands according to the invention are therefore preferably capable of (1) specifically binding to and/or specifically modulating the biological function of at least one of BAZ1B, PSIP1 and/or TSN and (2) modulating a T cell mediated immune response. The term "specifically" means that (a) the binding interaction between the ligand and its (intermediate) target or (b) its effect on the biological function of its target is detectable over non-specific (e.g. background) interactions or effects as measured by a quantifiable assay. For instance, binding specificity can be determined by various ligand binding assays such as Radioactive Ligand Binding Assays, ELISA, fluorescence based techniques (e.g. Fluorescence Polarization (FP), Fluorescence Resonance Energy Transfer (FRET)), or surface plasmon resonance. Specific modulation of a biological function can be assessed by choosing relevant endpoints (e.g. survival, activation, proliferation, expression of specific marker molecules) and comparing the action of L-arginine or (other) BPT ligands to the effect of untreated controls (such as PBS). A ligand "modulates" a biological function of its target if it totally or partially reduces, inhibits, interferes with, enhances, activates, stimulates, increases, reinforces or supports said biological function.

In the context of the present invention, L-arginine and (other) BPT ligands are therefore envisaged to modulate the biological functions of BAZ1B, PSIP1 and/or TSN. Said biological functions may include, without limitation, modulation of (a) T cell survival; (b) T cell differentiation; (c) T cell metabolism; (d) T cell cytokine secretion; (e) T cell expression of effector molecules; and/or (f) T cell effects on target cell differentiation, proliferation or apoptosis. Specifically, the present inventors demonstrated that L-arginine is capable of (1) enhancing T cell survival and (2) driving T cell differentiation towards a $T_{CM}$-like fate. Said effects are also envisioned for BPT ligands as described herein. T cell survival can be readily evaluated using routine methods known in the art such as annexin V staining and FACS analysis as described in the appended Examples. T cell differentiation is typically accompanied by the expression and release of specific cytokines. The cytokine profile of a T cell population thus gives information about its fate in terms of differentiation. For instance, central memory T cells ($T_{CM}$) express L-selectin and CCR7, they secrete IL-2, but not IFN-gamma or IL-4, whereas effector memory T cells ($T_{EM}$) do not express L-selectin or CCR7 but produce effector cytokines like IFN-gamma and IL-4. The present inventors found that L-arginine is capable of inducing a $T_{CM}$ like state characterized by the expression of L-selectin and CCR7 but not IFN-gamma.

As set out above, the present inventors discovered that L-arginine acts on and modulates the biological functions of BAZ1B, PSIP1 and/or TSN—which have been shown by the present inventors to enhance T cell survival and effector functions. BPT ligands for the use in a method of modulating a T cell mediated immune response in a subject according to the invention are therefore particularly envisaged to enhance said T cell mediated immune responses. L-arginine is a preferred BPT ligand of the invention. Accordingly, the invention further provides L-arginine for use in a method of modulating a T cell mediated immune response in a subject, wherein said immune response is enhanced.

A "ligand" can be essentially any type of molecule such as an amino acid, peptide, polypeptide, nucleic acid, carbohydrate, lipid, or small organic compound. The term "ligand" refers both to a molecule capable of binding to a target (or "intermediate" target in the context of the present invention) and to a portion or fragment of such a molecule, if that portion of a molecule is capable of binding to said target. Pharmaceutically acceptable derivatives, analogues, and mimetic compounds also are included within the definition of this term.

L-arginine—which has been shown to interact with (e.g. bind to) and/or act upon BAZ1B, PSIP1 and/or TSN and being a potent modulator of T cell mediated immune responses—is considered a preferred BPT ligand.

Further ligands of BAZ1B, PSIP1 and TSN (and thus candidate regulators of T cell function) can readily be identified. The skilled person is aware of a number of approaches for predicting target-ligand interactions in silico (e.g. reviewed in Sliwoski et al. Pharmacol Rev. 2014 January; 66(1): 334-395). Structure-based methods are in principle analogous to high-throughput screening in that both target and ligand structure information is imperative. Structure-based approaches include ligand docking, pharmacophore, and ligand design methods. Ligand clocking predicts the preferred orientation by conformation searching and energy minimization. Another structure-based approach relies on comparing target similarities, which compares the targets of a given ligand by sequences, EC number, domains, 3D structures, etc. Ligand-based methods such as ligand-based pharmacophores, molecular descriptors, and quantitative structure-activity relationships (QSAR), use only ligand information for predicting activity depending on its similarity/dissimilarity to previously known active ligands. Identification of potential ligands typically involves the screening of virtual compound libraries, also known as virtual high-throughput screening (vHTS). Such libraries can be prepared by enriching ligands from target/ligand data bases. Target Data Bases (such as the Protein Data Bank (PDB)) provide information regarding the structure of the target protein as determined by X-ray crystallography or NMR spectroscopy. When an experimentally determined structure of a protein is not available, it is often possible to create a comparative model ("homology model") based on the experimental structure of a related protein. Ligand Databases (such as PubChem, PDBeChem, Zinc, LIGAND, DrugBank, ChemDB and others) are often constructed by enriching ligands for certain desirable geometric or physiochemical properties suitable for the target of interest and/or by searching for ligands that are similar to known active ligands. Once a candidate ligand has been identified, it can be evaluated for its ability to modulate T-cell mediated immune responses.

In a further aspect, the present invention therefore provides a method of identifying a BAZ1B, PSIP1 and/or TSN ligand which is capable of modulating a T-cell mediated immune response, comprising the following steps of: i) cultivating a T cell population in a suitable cell culture medium the presence of IL-2 and a candidate ligand ii) removing IL-2 and said candidate ligand from the cell culture medium; and iii) determining the level of T cell survival in the presence of the candidate ligand as compared to an untreated control.

The method may comprise additional steps such as activating the T cells by contacting the T cells with (optionally immobilized) anti-CD3 antibody and/or anti-CD28 antibody. Suitable cell culture media are described in the context of the in vitro applications below.

IL-2 is a potent T cell growth factor and its removal from the cell culture medium is known to induce growth arrest and/or trigger cell death due to apoptosis. The level of T cell survival upon IL-2 withdrawal in the presence of the candidate ligand is determined by routine methods known in the art (e.g. annexin V staining and subsequent FACS analysis as described in the appended Examples) and compared to the level of survival in the absence of the candidate ligand (e.g. in the presence of a control). When T cell survival is significantly less or significantly higher in the presence of the candidate ligand than in its absence, the candidate ligand is identified as a modulator of T-cell mediated immune responses. It will be understood that IL-2 is preferably added to the cell culture medium in step (i) of the method in a concentration that supports T cell proliferation and survival, preferably in a concentration of 50-500 units per ml.

BPT Ligands

As indicated previously, the term "ligand" encompasses pharmaceutically acceptable derivatives. The term "pharmaceutically acceptable derivative" as used herein includes any derivative of said BPT ligand or any other compound which, upon administration to the recipient, is capable of providing (directly or indirectly) said BPT ligand or an active metabolite or residue thereof. For instance, useful derivatives are those that optimize the desired pharmacokinetic properties of said BPT ligand, e.g. increase its stability, bioavailability, absorption; optimize its distribution and/or reduce its clearance (if desired).

The specific nature of a derivative depends on the ligand itself. Useful derivatives of small organic molecule BPT ligands (including amino acid BPT ligands) may include pharmaceutically acceptable salts. Such salts can be prepared from an inorganic acid or from an organic acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, arylaliphatic, heterocyclic, carboxylic and sulfonic classes of organic acids, example of which are acetic, adipic, algenic, anthranilic, ascorbic, aspartic, benzoic, benzenesulfonic, butyric, camphoric, camphorsulfonic, citric, cyclopentanepropionic, cyclohexylaminosulfonic, digluconic, dodecylsulfonic, ethanesulfonic, formic, fumaric, galactaric, galacturonic, glycolic, gluconic, glucuronic, glucoheptanoic, glutamic, glycerophosphonic, heptanoic, hexanoic, 4-hydroxybenzoic, 2-hydroxyethanesulfonic, β-hydroxybutyric, lactic, malic, maleic, mandelic, mesylic, methanesulfonic, nicotinic, 2-naphthalenesulfonic, oxalic, palmoic, pectinic, pivalic, persulfuric, 2-phenylpropionic, picric, pyruvic, propionic, phenylacetic, embonic (pamoic), cyclopentane proprionic, pantothenic, toluenesulfonic, salicylic, sulfanilic, stearic, succinic, tartaric, thiocyanic, and undecanoic acid. Further suitable salts include metallic salts, such as salts made from alkali metals and alkaline earth metals including, for example, aluminum, calcium, lithium, magnesium, potassium, sodium and zinc, or salts made from organic bases including primary, secondary and tertiary amines, substituted amines including cyclic amines, such as caffeine, arginine, diethylamine, N-ethyl piperidine, histidine, glucamine, isopropylamine, lysine, morpholine, N-ethyl morpholine, piperazine, piperidine, ammonia, triethylamine, trimethylamine. All of these salts may be prepared by conventional means from the corresponding ligand by reacting, for example, the appropriate acid or base with said ligand. Other derivatives of small organic molecule BPT ligands include esters or other covalently modified molecules.

The term "BPT ligand" for instance also encompasses conjugates comprising moieties introduced to increase serum half-life and stability and/or to reduce immunogenicity of the ligand. Exemplary moieties that are particularly useful for coupling to protein or peptide BPT ligands include polyethylene glycol (PEG), dextrans, polysialic acids (PSAs), hyaluronic acid (HA), dextrin, hydroxyethyl-starch (HES), poly(2-ethyl 2-oxazoline) (PEOZ), or polypeptides (XTEN technology, PASylation) or fatty acids (lipidation). These moieties can be chemically or enzymatically coupled to the respective protein or peptide BPT ligand. Protein or peptide BPT ligands can also be genetically fused to antibody Fc domains and human serum albumin (HAS) or subjected to alternative glycosylation in order to generate useful derivatives within the scope of the present invention. In any case the BPT ligand derivatives for the uses according to the invention are preferably functional derivatives which retain their function of (1) specifically binding to and/or modulating the biological function of BAZ1B, PSIP1 and/or TSN and (2) modulating, preferably enhancing, T cell mediated immune responses. It will be acknowledged that L-arginine is a preferred BPT ligand according to the invention.

L-Arginine

As demonstrated in the appended Examples, the present inventors surprisingly identified L-arginine as a potent modulator of T cell survival and effector functions.

L-arginine is classified as a semiessential or conditionally essential amino acid. It is synthesized from citrulline in arginine and proline metabolism by the sequential action of the cytosolic enzymes argininosuccinate synthetase (ASS) and argininosuccinate lyase (ASL). With a pKa of 12.48, arginine is positively charged in neutral, acidic, and even most basic environments, and thus exhibits basic chemical properties. The structural formula of L-Arginine is depicted in formula (I) below:

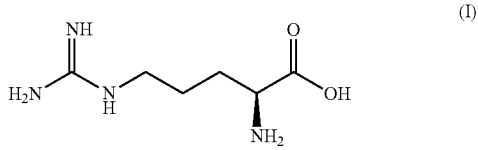 [SMILES: N=C(N)NCCC[C@H](N)C(=O)O]

(I)

The term "L-arginine" includes pharmaceutically acceptable derivatives. The term "pharmaceutically acceptable derivative" as used herein includes any derivative of L-arginine, which, upon administration to the recipient, is capable of providing (directly or indirectly) L-arginine or an active metabolite thereof. For instance, useful derivatives are those that optimize the desired pharmacokinetic properties of L-arginine, e.g. increase its stability, bioavailability or absorption; optimize its distribution and/or reduce its clearance (if desired).

Useful derivatives of L-arginine include pharmaceutically acceptable salts thereof. Such salts can be prepared from an inorganic acid or from an organic acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, arylaliphatic, heterocyclic, carboxylic and sulfonic classes of organic acids, example of which are acetic, adipic, algenic, anthranilic, ascorbic, aspartic, benzoic, benzenesulfonic, butyric, camphoric, camphorsulfonic, citric, cyclopentanepropionic, cyclohexylaminosulfonic, digluconic, dodecylsulfonic, ethanesulfonic, formic, fumaric, galactaric, galacturonic, glycolic, glucosic, glucuronic, glucoheptanoic, glutamic, glycerophosphonic, heptanoic, hexanoic, 4-hydroxybenzoic, 2-hydroxyethanesulfonic, β-hydroxybutyric, lactic, malic, maleic, mandelic, mesylic, methanesulfonic, nicotinic, 2-naphthalenesulfonic, oxalic, palmoic, pectinic, pivalic, persulfuric, 2-phenylpropionic, picric, pyruvic, propionic, phenylacetic, embonic (pamoic), cyclopentane proprionic, pantothenic, toluenesulfonic, salicylic, sulfanilic, stearic, succinic, tartaric, thiocyanic, and undecanoic acid. Further suitable salts include metallic salts, such as salts made from alkali metals and alkaline earth metals including, for example, aluminum, calcium, lithium, magnesium, potassium, sodium and zinc, or salts made from organic bases including primary, secondary and tertiary amines, substituted amities including cyclic amines, such as caffeine, arginine, diethylamine, N-ethyl piperidine, histidine, glucamine, isopropylamine, lysine, morpholine, N-ethyl morpholine, piperazine, piperidine, ammonia, triethylamine, trimethylamine. All of these salts may be prepared by conventional means from L-arginine by reacting, for example, the appropriate acid or base with L-arginine.

It will be acknowledged that with a $pK_a$ of 12.48, L-arginine is positively charged in neutral, acidic, and even most basic environments, and thus has basic chemical properties in most environments. Therefore, pharmaceutically acceptable salts derived from acids, including inorganic and organic acids, are particularly envisaged.

Other useful L-arginine derivatives include pharmaceutically acceptable esters, such as L-arginine methyl ester or L-arginine ethyl ester. Esters can be prepared by reacting L-arginine with carboxylic acids and alcohols.

Preferred L-arginine derivatives within the context of the present invention include, without limitation, L-arginine hydrochloride, L-arginine malate, L-arginine methyl ester, L arginine ethyl ester, and combinations thereof.

The term "L-arginine" however also encompasses otherwise covalently modified derivatives, analogues, and mimetic compounds exhibiting comparable or even improved characteristics as compared to L-arginine evaluated in the appended Examples.

L-arginine and its derivatives, in particular its pharmaceutically acceptable salts and esters, have the considerable advantages of being readily available, easy to store and handle, and relatively inexpensive. L-arginine or (other) BPT ligands can simply be added to the cell culture medium to increase T cell survival and immune responses in vitro/ex vivo. In addition, L-arginine can be orally administered which has the advantages of being convenient, cheap, does not require sterilization, and can be accomplished with a variety of dosage forms. Said features and benefits are particularly advantageous in ACT applications that have previously been hampered by the rapid clearance and low survival of re-infused T cells in vivo.

In Vitro Applications

T Cell Cultivation

The present inventors demonstrated that L-arginine is inter alia capable of effectively promoting T cell survival in vitro. The present invention thus further relates to an in vitro method of contacting an (isolated) T cell with L-arginine or (other) BPT ligands. The method is considered to be particularly useful for in vitro cultivation of T cells for a variety of applications. Such methods comprise contacting an (isolated) T cell with a L-arginine or (other) BPT ligands in a suitable cell culture medium. Preferably, said (other) BPT ligands are selected from L-arginine (or derivatives thereof).

As used herein, the term "isolated" generally means 1) separated from at least some of the components with which it is usually associated in nature; 2) prepared or purified by a non-naturally occurring process; 3) not occurring in nature; and/or 4) not present as an integral part of an organism. An "isolated" T cell thus in particular refers to a T cell that exists in a non-native environment (in particular a suitable cell culture medium), i.e. apart from the host from which it has been derived. The term "T cell" refers not only to the particular subject cell but to the progeny or potential progeny of such a cell. The term includes primary T cells, secondary T cells and T cell lines. Primary T cells are typically obtained from peripheral blood mononuclear cells (PBMC) derived from a blood sample or a tissue sample (e.g. a tumor tissue sample) and expanded ex vivo. The terms "expanding" and "expansion" in all their grammatical forms are used interchangeably herein with "proliferation"/"proliferating", "propagation"/"propagating", and "growth"/"growing" and refer to an increase in cell number. As used herein the term "ex vivo" refers to cells that are removed from a living organism and are propagated outside the organism (e.g., in a test tube). As used herein, the term "ex vivo", however, preferably does not refer to cells known to propagate only in vitro, such as various cell lines. T cells expanded ex vivo in the presence of L-arginine or (other) BPT ligands can for instance be employed for adoptive T cell therapy (ACT) as described below.

A "suitable cell culture medium" is generally understood as a cell culture medium that allows for cultivation of T cells. "Culture" or "cell culture" refers to the maintenance, growth and/or differentiation of cells in an in vitro environment. The term "cell culture" may encompass the cultivation of individual cells or cell populations. "Cell culture media," "culture media" (singular "medium" in each case), "supplement" and "media supplement" refer to nutritive compositions that cultivate cell cultures. "Cultivation" refers to the maintenance and optionally growth, and/or differentiation of cells in an in vitro environment, typically in a suitable cell culture vessel (i.e. a glass, plastic, metal or other container such as a cell culture dish or flask that provides an environment for culturing cells), for example in a sterile plastic (or coated plastic) vessel. "Cultivation" may utilize a culture medium as a source of nutrients, hormones and/or other factors helpful to propagate and/or sustain the cells. Basal cell culture media may comprise amino acids, vitamins, organic salts, inorganic salts, trace elements, buffering salts, sugars, ATP, and the like and are commercially available. The skilled person will be readily able to choose a cell culture medium (and optionally suitable cell culture supplements) for cultivating T cells in vitro/ex vivo. Examples of basal cell culture media include, without limitations, medium MCDB 153 (for example, Sigma Aldrich Catalog #M7403), medium F12 (for example, Sigma Aldrich Catalog #N6658), medium RPMI 1640 (for example, Sigma Aldrich Catalog #R8758), Dulbecco's Modified of Eagle's medium (DME, for example, Sigma Aldrich Catalog #D5796) available from Sigma-Aldrich, of St. Louis, Mo. Similar media are available from other suppliers (e.g., Invitrogen Corporation, Carlsbad, Calif.).

The cell culture medium may further comprise cell culture supplements such as serums, extracts, growth factors, hormones, cytokines, antigens and the like. Cytokines used in the culture media may include, for example, one or more of the following: growth factors such as epidermal growth factor (EGF), acidic fibroblast growth factor (aFGF), basic fibroblast growth factor (bFGF), hepatocyte growth factor (HGF), insulin-like growth factor 1 (IGF-1), insulin-like growth factor 2 (IGF-2), keratinocyte growth factor (KGF), nerve growth factor (NGF), platelet-derived growth factor (PDGF), transforming growth factor beta (TGF-β3), vascular endothelial cell growth factor (VEGF) transferrin, various interleukins (such as IL-1 through IL-18), various colony-stimulating factors (such as granulocyte/macrophage colony-stimulating factor (GM-CSF)), various interferons (such as IFN-gamma) and other cytokines such as stem cell factor (SCF) and erythropoietin (Epo). These cytokines may be obtained commercially, for example from R&D Systems, Minneapolis, Minn., and may be either natural or recombinant.

Vitamin ingredients which may be included in the cell culture media include ascorbic acid magnesium salt, biotin, choline chloride, D-Ca$^{++}$-pantothenate, folic acid, z'-inositol, menadione, niacinamide, nicotinic acid, paraaminobenzoic acid (PABA), pyridoxal, pyridoxine, riboflavin, thiamine HCl, vitamin A acetate, vitamin $B_{12}$ and vitamin $D_2$. These vitamins may be obtained commercially, for example from Sigma (Saint Louis, Mo.).

Inorganic salt ingredients which may be used in the media of the present invention include $CaCl_2$, KCl, $MgCl_2$, $MgSO_4$, NaCl, $NaHCO_3$, $NaH_2PO_4$ $H_2O$ and ferric citrate chelate or ferrous sulfate chelate. These inorganic salts may be obtained commercially, for example from Sigma (Saint Louis, Mo.).

Trace elements which may be used in the media of the present invention include ions of barium, bromium, cobalt, iodine, manganese, chromium, copper, nickel, selenium, vanadium, titanium, germanium, molybdenum, silicon, iron, fluorine, silver, rubidium, tin, zirconium, cadmium, zinc and aluminum. These ions may be provided, for example, in trace element salts such as $Ba(C_2H_3O_2)_2$, KBr, $CoCl_2$ $6H_2O$, KI, $MnCl_2$ $4H_2O$, $Cr(SO_4)_3$ $15H_2O$, $CuSO_4$ $5H_2O$, $NiSO_4$ $6H_2O$, $H_2SeO_3$, $NaVO_3$, $TiCl_4$, $GeO_2$, $(NH_4)_6Mo_7O_{24}$ $4H_2O$, $Na_2SiO_3$ $9H_2O$, $FeSO_4$ $7H_2O$, NaF, $AgNO_3$, RbCl, $SnCl_2$, $ZrOCl_2$ $8H_2O$, $CdSO_4$ $8H_2O$, $ZnSO_4$ $7H_2O$, $Fe(NO_3)_3$ $9H_2O$, $AlCl_3$ $6H_2O$.

The skilled person will readily be able to determine further ingredients or supplements such as antigens or ligands that are useful for T cell maintenance and/or propagation and (if desired) activation and differentiation. It will be acknowledged that such ingredients or supplements preferably do not interfere with the advantageous capabilities of L-arginine or (other) BPT ligands.

L-arginine is particularly envisaged for use in the in vitro method of the invention. However any (other) BPT ligand (or combinations thereof) may equally be used. L-arginine or (other) BPT ligands are preferably added to the cell culture medium in an amount sufficient to promote the desired T cell function, in particular survival of said T cells. Suitable amounts of L-arginine or (other) BPT ligands are readily ascertainable using routine techniques known in the art. Suitable concentrations L-arginine or (other) BPT ligands can be evaluated by cultivating the T cells in the presence of different concentrations of L-arginine or (other) BPT ligands and assessing T cell survival. Useful methods for determining T cell survival include annexin V staining with fluorescent conjugates (e.g., Alexa Fluor®, Thermo Fisher Scientific, Catalogue #A23202, #A13201, #A35108, #A13202, #A13203, #A23204, #A35109), MTT Tetrazolium Assay (e.g. CellTiter 96 AQueous One Solution Cell Proliferation Assay, Promega Corp., Catalogue #G3580), Resazurin Reduction Assays (e.g., CellTiter-Blue Cell Viability Assay, Promega Corp Catalogue #G8081) or ATP Assays (e.g., CellTiter-Glo® Luminescent Cell Viability Assay, Promega Corp. Catalogue #G7570). The concentration of L-arginine or (other) BPT ligands in the cell culture medium may range between 1 uM to 10 M, including concentrations of at least 1 uM, at least 10 uM, at least 10 uM, at least 1 mM, at least 10 mM, at least 100 mM, or at least 1 M. In particular, L-arginine concentrations used in the in vitro methods of the invention may be at least 1 uM, preferably at least 10 uM, more preferably at least 100 uM, and most preferably at least 1 mM, such as at least 1 mM, at least 2 mM, at least 3 mM, at least 4 mM, at least 5 mM or higher. The present inventors demonstrated that an L-arginine concentration of 3 mM is particularly useful and effectively promotes T cell survival in vitro.

The in vitro cultivation method is envisaged for any of the T cells exemplified herein. The required concentration of the ligand in the cell culture medium will depend inter alia on the type and activity of the employed ligand, the cell culture medium and the type of cultivated T cells and is readily ascertainable using routine methods known in the art.

The in vitro method described herein is useful for a variety of research and therapeutic applications. It is applicable for primary cell culture (i.e. T cells derived from a donor), secondary cell culture (i.e. sub-cultured primary cell culture) or cultivation of T cell lines and a variety of therapeutic applications. The method may comprise further steps depending on the intended application and use of the T cells cultivated according to the method of the invention.

The in vitro method of the invention may comprise a step of activating the cultivated T cells. Cultivated T cells may be activated by contacting the cells with (i) an anti-CD3 and/or anti-CD28 antibody that is optionally immobilized and/or (ii) a MHC-I or MHC-II bound antigen optionally presented by an antigen-presenting cell. Cultivated T cells may also be activated by adding cytokines (such as IL-2) or other ingredients as exemplified above to the cell culture medium. The in vitro method of the invention may comprise a step of enriching a particular T cell subset (e.g. by sorting for a particular cell surface marker such as CD4 or CD8). The in vitro method of the invention may comprise a step of screening the cultivated T cells for their binding specificity towards a preselected antigen or epitope thereof. An "antigen" refers to any substance capable, under appropriate conditions, of inducing a specific immune response and reacting with the products of said immune response, for instance T cells (via their T cell receptors) or antibodies or B cells (via their B cell receptors). Antigens may be soluble substances, such as toxins and foreign proteins, peptides, carbohydrates, lipids or combinations thereof, or particulates, such as bacteria and tissue cells. However, only a portion (or fragment) known as the epitope or antigenic determinant of the antigen interacts with the immune system. Thus, one antigen has at least one epitope, i.e. a single antigen typically has one or more epitopes. In the context of the present invention, the term "epitope" is mainly used to designate T cell epitopes, which are presented on the surface of an antigen-presenting cell, where they are bound to Major Histocompatibility Complex (MHC). T cell epitopes presented by MHC class I molecules are typically, but not exclusively, peptides between 8 and 11 amino acids in length, whereas MHC class II molecules present longer peptides, generally, but not exclusively, between 12 and 25 amino acids in length.

The in vitro method of the invention may comprise a step of genetically modifying (or "engineering") the T cells. Genetic engineering of the T cells can be accomplished using routine techniques known in the art in order to (a) increase expression of BAZ1B, PSIP1 and/or TSN; and/or (b) endow the T cells with a recombinant T cell receptor (TCR) or a chimeric antigen receptor (CAR); and/or (c) increase or induce expression of other effector molecules such as inducible suicide molecule (e.g. herpes simplex virus thymidine kinase (HSV-TK)) or fusion proteins containing a human FAS or caspase death domain and a modified FK506-binding protein (FKBP). In particular, T cells may be genetically modified by transforming the cells with a nucleic acid molecule or vector comprising a polynucleotide that encodes the desired polypeptides/proteins of interest (such as BAZ1B, PSIP1, TSN, a TCR or CAR or other effector molecules). Methods of transforming T cells with nucleic acid molecules or vectors are described in detail below (cf. "In vitro Applications). Specifically, in the in vitro method of the invention may thus include a step of genetically modifying the T cells by transforming said T cells with the nucleic acid molecule and/or the vector according to the invention, which are described in greater detail below.

As explained, the in vitro method described herein finds use in a variety of research and therapeutic application. The present inventors have demonstrated that T cells contacted with L-arginine or (other) BPT ligands in vitro exhibited an increased survival and anti-tumor activity when being re-introduced into appropriate recipients. Accordingly, the in vitro method described herein is considered to be particularly useful for adoptive cell therapy (ACT) applications as described below (e.g. for ex vivo expansion of the T cells).

Adoptive T Cell Therapy

Adoptive cell therapy (ACT), involves the isolation and ex vivo expansion of useful cells, in particular antigen-specific T cells from a patient (autologous transfer) or a suitable donor (allogenic transfer) and their (re-)introduction into the patient. T cells are typically enriched from peripheral blood mononuclear cells (PBMC) obtained from a serum or plasma sample or from (tumor) biopsies yielding tumor infiltrating lymphocytes (TILs). There are different forms of adoptive T cell therapy. ACT may involve the isolation and expansion of one particular T cell from the donor which already exhibits the desired antigen specificity (e.g. from TILs or after administering a respective vaccine to the donor). ACT may also rely on genetically engineering of extracted T cells in order to equip them with recombinant TCRs or chimeric antigen receptors (CARs) of the desired antigen specificity. ACT may thus optionally include one or more steps of (i) screening T cells for the desired antigen specificity; (ii) enriching particular T cell subsets (e.g. by sorting for cell surface markers such as CD4 or CD8); (iii) activating T cells (e.g. by contacting the cells with anti-CD3 and/or anti-CD28 antibodies and/or an MHC-I or MHC-II bound antigen optionally presented by an antigen-presenting cell and/or cytokines (such as IL-2) or other effector molecules); (iv) genetically engineering the T cells for expression of a recombinant TCR, CAR or other effector molecule such as inducible suicide molecules (e.g. herpes simplex virus thymidine kinase (HSV-TK)) or fusion proteins containing a human FAS or caspase death domain and/or a modified FK506-binding protein (FKBP) and/or (v) exposing the T cells to cytokines or growth factors in order to promote proliferation, differentiation and/or activation. The expanded and/or activated T cells are subsequently (re-) introduced into the recipient. ACT can be used, for example, for preventing or treating cancer, infections (infectious diseases) and/or autoimmune diseases.

Albeit ACT is a promising approach of personalized medicine and holds great potential for highly effective treatment of various diseases, such as cancer and/or infection, its application has been hampered by the fact that T cells are often rapidly eliminated after (re-)introduction into the patient and thereby lose their therapeutic efficacy. The present inventors established that L-arginine (or (other) BPT ligands) effectively promote T cell survival and effector functions in vivo when being added to T cells during expansion in vitro.

In a further aspect, the present invention therefore features a BAZ1B, PSIP1 and/or TSN ligand ("BPT ligand") for use in a method of adoptive T cell therapy (ACT). A preferred BPT ligand in accordance with the invention is L-arginine. Accordingly, the present invention further provides L-arginine for use in a method of adoptive T cell therapy (ACT). In this context, ACT is particularly envisaged for treatment or prevention of cancer, infection (infectious diseases) and/or autoimmune diseases.

T Cells and T Cell Immunity

L-arginine and (other) BPT ligands as described herein are envisaged to be capable of effectively modulating T cell mediated immune responses and are therefore considered promising new tools for T cell based immunotherapy, e.g. for treating cancer, infection (infectious diseases) and/or autoimmune diseases.

As is well-known in the art, "T cells" or "T lymphocytes" are an essential part of the immune system. T cells are characterized by the expression of a T cell receptor (TCR), a disulfide-linked membrane-anchored heterodimeric protein normally consisting of the highly variable alpha ($\alpha$) and beta ($\beta$) chains expressed as part of a complex with the invariant CD3 chain molecules. Via their TCR, T cells are capable of specifically recognizing antigens originating from pathogens or tumor cells (tumor-associated antigens, TAA).

T cells originate from hematopoietic stem cells in the bone marrow and mature in the thymus where they multiply and differentiate into CD4$^+$ T cells (also referred to as "helper T cells") or CD8$^+$ T cells (also referred to as "cytotoxic T cells) which migrate to peripheral tissues or circulate in the blood or lymphatic system. Once a naïve T cell recognizes via its TCR a specific presented by an antigen-presenting cell (APC) on an MHC molecule, the T cell is activated and a dynamic proliferation and differentiation process occurs, resulting in formation of both primary effector and long-lived memory T cells. Primary effector T cells are short-lived cells, whereas the subset of memory T cells persists even in the absence of antigen either in the secondary lymphoid organs (central memory cells, $T_{CM}$) or in the recently infected tissues (effector memory cells, $T_{EM}$ cells). Upon re-exposure to a specific antigen, memory T cells undergo fast expansion and cause more effective and faster secondary immune response versus the primary immune response which eliminates infection.

As used herein, the term "T cell" embraces all kinds of T lymphocytes including naïve CD4+ and CD8+ T cells as well as memory and effector subsets of CD4+ and CD8+ T cells. Effector subsets of CD4+ T cells include Type 1 (Th1) and Type 2 (Th2) helper T cells as well as Th2, Th9, Th17, Th22, Treg (regulatory T cells), and Tfh (follicular helper T cells). The effector subsets of CD8+ T cells is referred to as $T_{EFF}$ and is also encompassed by the definition. Memory subsets of CD4+ and CD8+ T cells include CD4+ and CD8+ stem memory $T_{SCM}$ cells, effector memory cells ($T_{EM}$) and CD4+ and CD8+ central memory cells, $T_{CM}$.

Naive conventional T cells and regulatory T cells (effector and memory subtypes) differ in their extracellular, intracellular, epigenetic, and genetic markers, transcription factors, and metabolic pathways. It will be acknowledged that different T cell subsets exert different biological functions and thus mediate different immune responses. For instance, CD4+ cells recognize predominantly exogenous antigens (i.e. derived from extracellular antigens) presented by professional APCs on class II MHC molecules (MHC-II). CD4+ effector cells therefore mostly mediate immune responses against bacteria, protozoa and parasites. CD4+ Th1 helper cells inter alia act on macrophages and mediate immune responses against intracellular bacteria and protozoa. CD4+ Th2 helper cells mainly act on eosinophils, basophils, and mast cells as well as B cells, which are stimulated to differentiate into antibody-producing plasma cells. Thereby, CD4+ Th2 helper cells mainly mediate immune responses against extracellular pathogens and parasites. CD4+ T cells are however also involved in mediating CD8+ T cell responses.

CD8+ cells recognize endogenous antigens presented on class I Molecules (MHC-I) expressed on almost all host cells. Host cells infected with intracellular pathogen (such as a virus) and neoplastic cells present foreign antigens on their MHC-I molecules which are recognized by CD8+ cytotoxic T cells. The CD8+ T cells proliferate and differentiate into CD8+ effector host cells which kill the infected or neoplastic cell by releasing cytotoxic cytokines or expressing ligands that induce apoptosis in the infected or neoplastic target cell.

ACT strategies have largely focused on the infusion of antigen-specific CD8+ T cells (CTL) which can directly kill target cells. However, CD4$^+$ T cells are also useful in ACT because they can activate antigen-specific effector cells and recruit cells of the innate immune system such as macrophages and dendritic cells to assist in antigen presentation. They can also can directly activate antigen-specific CTL and are therefore attractive targets of ACT approaches.

As indicated above, different T cell subsets exert different biological functions and thus mediate different immune responses. For instance, each T cell subset releases specific cytokines that can have either pro- or anti-inflammatory, survival or protective functions and act on different downstream effector cells of the immune system. For example, Th1 effector cells release IFN-gamma and TNF which act on macrophages as and CD8+ T cells; Th2 effector cells release IL-4, IL-5 and IL-13 which induce B cell mediated responses. "T cell mediated immune responses" therefore generally include immune responses directly mediated by T cells (e.g. killing of target cells by cytotoxic T cells) and immune responses that are directly mediated by other effector cells (e.g. B cells) but require T cell functions, e.g. the provision of (co-)stimulatory signals. "T cell mediated immune responses" as used herein therefore include immune responses directly mediated via T cell functions (e.g., cytokine production, and cellular cytotoxicity in response to intracellular pathogens or tumors) as well as immune responses indirectly mediated via T cell functions (e.g., antibody production in response to extracellular pathogens or activation of other cytokine responsive cells such as macrophages, eosinophils, neutrophils and the like (e.g. in response to parasites)). The term "T-cell mediated immune response" particularly refers to include (1) anti-cancer responses and (2) anti-infection responses. "Anti-cancer responses" are immune responses involving the attack and killing of neoplastic cells. "Anti-infection responses" are immune responses involving the attack and killing of infected cells and/or extracellular pathogens or parasites.

In a further aspect, the present invention therefore provides a BAZ1B, PSIP1 and/or TSN ligand ("BPT ligand") for use in a method of modulating a T cell mediated immune response which is an anti-cancer response or an anti-infection response. L-arginine is a preferred BPT ligand. Accordingly, the present invention also features L-arginine for use in a method of modulating a T cell mediated immune response which is an anti-cancer response or an anti-infection response.

Accordingly, in a further aspect the present invention provides a BAZ1B, PSIP1 and/or TSN ligand ("BPT ligand") for use in treating cancer and/or infection. L-arginine is a preferred BPT ligand. Accordingly, the present invention also features L-arginine for use in a method of treating cancer and/or infection.

Nucleic Acids

The present inventors gained novel insights into the effects of BAZ1B, PSIP1 and TSN on T cell function which pave the way for a variety of therapeutic applications. The present invention further relates to nucleic acids and vectors that can be used in a variety of therapeutic approaches and are particularly considered useful in gene therapy.

BAZ1B, PSIP1 and/or TSN Encoding Polynucleotides

In a further aspect, the present invention therefore provides a nucleic acid comprising at least one polynucleotide sequence encoding BAZ1B, PSIP1 or TSN. Specifically, the nucleic acid molecule of the invention comprises a polynucleotide sequence encoding (1) a BAZ1B polypeptide comprising or consisting of the sequence depicted in SEQ ID NO: 1 or an isoform or functional variant thereof, and/or (2) a PSIP1 polypeptide comprising or consisting of the sequence depicted in SEQ ID NO: 2 or an isoform or a functional variant thereof, and/or (3) a TSN polypeptide comprising or consisting of the sequence depicted in SEQ ID NO: 3 or an isoform or a functional variant thereof, and optionally at least one regulatory element operably linked to any one or each of (1) to (3).

Polynucleotide sequences (1) to (3) encoding the indicated polypeptides are also designated "polynucleotide sequences of interest" herein.

The terms "nucleic acid", "nucleic acid molecule", "nucleic acid fragment", "nucleic acid sequence or segment", or "polynucleotide" are used interchangeably herein to refer to deoxyribonucleotides or ribonucleotides and polymers thereof in either single- or double-stranded form, composed of monomers (nucleotides) containing a sugar, phosphate and a nitrogenous base that is either a purine or pyrimidine. A nucleoside comprises a nitrogenous base linked to a sugar molecule. The term "polynucleotide" thus generally includes without limitation probes, oligonucleotides, constructs, genomic DNA, antisense DNA, antisense RNA, cDNA, PCR products, restriction fragments, messenger RNA (mRNA), transfer-messenger-RNA (tmRNA), transfer RNA (tRNA), micro RNA (miRNA), ribosomal RNA (rRNA), small interfering RNA (siRNA), small hairpin RNA (shRNA), PNA, single-stranded RNA (ssRNA), double-stranded RNA (dsRNA), single-stranded DNA (ssDNA), double-stranded DNA (dsDNA), DNA:RNA hybrid molecules, ribozymes, aptamers, mini-genes, gene fragments and combinations thereof; all of the aforementioned with or without regulatory elements, untranslated regions or combinations thereof. As is well-known, deoxyribonucleic acid (DNA) in the majority of organisms is the genetic material while ribonucleic acid (RNA) is involved in the transfer of information contained within DNA into proteins. In the context of the present invention, polynucleotides preferably comprise single stranded, double stranded or partially double stranded nucleic acids which may be DNA or RNA. Particularly envisaged are sense or antisense DNA, cDNA and RNA (in particular mRNA) or combinations thereof.

The length of a polynucleotide is not limited in any respect. Linkages between nucleotides can be phosphodiester linkages, or any other type of linkage such as phosphorothioate and 5'-N-phosphoramidite linkages. A polynucleotide can be produced by biological means (e.g., enzymatically), either in vivo (in a cell) or in vitro (in a cell-free system). A polynucleotide can be chemically synthesized using enzyme-free systems. A polynucleotide can be enzymatically extendable or enzymatically non-extendable.

The term "polynucleotide" is not limited to naturally occurring polynucleotide structures, naturally occurring nucleotides sequences, naturally occurring backbones or naturally occurring internucleotide linkages. One familiar with the art knows well the wide variety of polynucleotide analogues, unnatural nucleotides, non-natural phosphodiester bond linkages and internucleotide analogs that find use with the invention. Polynucleotides may thus include natural nucleosides (e.g., adenosine, thymidine, guanosine, cytidine, uridine, deoxyadenosine, deoxythymidine, deoxyguanosine, and deoxycytidine), nucleoside analogs (e.g., 2-aminoadenosine, 2-thiothymidine, inosine, pyrrolo-pyrimidine, 3-methyl adenosine, C5-propynylcytidine, C5-propynyluridine, C5-bromouridine, C5-fluorouridine, C5-iodouridine, C5-methylcytidine, 7-deazaadenosine, 7-deazaguanosine, 8-oxoadenosine, 8-oxoguanosine, O(6)-methylguanine, and 2-thiocytidine), and/or nucleosides comprising chemically or biologically modified bases, (e.g., methylated bases), intercalated bases, and/or modified sugars (e.g., 2'-fluororibose, ribose, 2'-deoxyribose, arabinose, and hexose). Polynucleotides need not be uniformly modified along the entire length of the molecule. A polynucleotide comprising non-naturally occurring polynucleotide structures, sequences, backbones or internucleotide linkages is referred to as a "modified polynucleotide" herein. For example, different nucleotide modifications, different backbone structures, etc., may exist at various positions in the polynucleotide or oligonucleotide. Any of the polynucleotides described herein may utilize these modifications.

By convention, polynucleotides that are formed by 3'-5' phosphodiester linkages (including naturally occurring polynucleotides) are said to have 5'-ends and 3'-ends because the nucleotide monomers that are incorporated into the polymer are joined in such a manner that the 5' phosphate of one mononucleotide pentose ring is attached to the 3' oxygen (hydroxyl) of its neighbor in one direction via the phosphodiester linkage. Thus, the 5'-end of a polynucleotide molecule generally has a free phosphate group at the 5' position of the pentose ring of the nucleotide, while the 3' end of the polynucleotide molecule has a free hydroxyl group at the 3' position of the pentose ring. Within a polynucleotide molecule, a position that is oriented 5' relative to another position is said to be located "upstream," while a position that is 3' to another position is said to be "downstream." This terminology reflects the fact that polymerases proceed and extend a polynucleotide chain in a 5' to 3' fashion along the template strand. Unless denoted otherwise, whenever a polynucleotide sequence is represented, it will be understood that the nucleotides are in 5' to 3' orientation from left to right.

The nucleic acid molecule disclosed herein and comprising a polynucleotide encoding BAZ1B, PSIP1 and/or TSN may comprise (1) a polynucleotide sequence comprising or consisting of the sequence depicted in SEQ ID NO: 4 or a functional variant thereof, and/or (2) a polynucleotide sequence comprising or consisting of the sequence depicted in SEQ ID NO: 5 or a functional variant thereof, and/or (3) a polynucleotide sequence comprising or consisting of the sequence depicted in SEQ ID NO: 6 or a functional variant thereof; and optionally at least one regulatory element operably linked to any one or each of (1) to (3).

Polynucleotide variants include sequences that contain minor, trivial or inconsequential changes to the reference (or parent) sequence (i.e., in particular, SEQ ID NO: 4-6). For example, minor, trivial or inconsequential changes include changes to the polynucleotide sequence that (i) do not change the amino acid sequence of the encoded polypeptide, (ii) occur outside the protein-coding open reading frame of a polynucleotide, (iii) result in deletions or insertions that may impact the corresponding amino acid sequence, but have little or no impact on the biological function of the polypeptide, and/or (iv) result in the substitution of an amino acid with a chemically similar amino acid in the encoded polypeptide. The variants are therefore envisaged to be functional variants. A sequence variant of a polynucleotide of interest is termed a "functional variant" if retains the biological function of the respective reference polynucleotide sequence, i.e. it encodes (1) a BAZ1B polypeptide comprising or consisting of the sequence depicted in SEQ ID NO: 1 or an isoform or functional variant thereof, and/or (2) a PSIP1 polypeptide comprising or consisting of the sequence depicted in SEQ ID NO: 2 or an isoform or a functional variant thereof, and/or (3) a TSN polypeptide comprising or consisting of the sequence depicted in SEQ ID NO: 3 or an isoform or a functional variant thereof. Functional variants of the aforementioned polynucleotide sequences of interest and preferably comprise or consist of a polynucleotide sequence which is at least 75%, preferably at least 80%, preferably at least 85%, more preferably at least 90%, more preferably at least 95%, more preferably at least 96%, more preferably at least 97%, most preferably at least 98%, most preferably at least 99% or 100% identical to the respective reference sequence.

The polynucleotide sequence of the open reading frame encoding the desired expression product (e.g., a BAZ1B, PSIP1 and/or TSN protein) can be readily isolated from a genomic DNA source, a cDNA source, or can be synthesized (e.g., via PCR). The polynucleotide sequence may further comprise non-coding polynucleotide sequences ("regulatory elements"). Such regulatory elements can be derived from libraries or databases and chemically synthesized and can be included to optimize transcription, mRNA processing and stabilization and translation into the respective amino acid sequence. Regulatory elements can be linked to polynucleotide sequences of interest by ligation at suitable restriction sites or via adapters or linkers inserted into the sequence using restriction endonucleases known to one of skill in the art.

Regulatory Elements

As indicated above, the nucleic acid molecule of the present invention may optionally further comprise at least one regulatory element operably linked to any one or each of the polynucleotide sequences of interest.

The term "operably linked" refers to the linkage of a polynucleotide sequence to another polynucleotide sequence in such a way as to allow the sequences to function in their intended manner. A polynucleotide sequence encoding a protein is for example "operably linked" to a regulatory element when it is ligated to said element in a functional manner which allows expression of the polynucleotide sequence.

The terms "regulatory element" or "regulatory sequence" are used interchangeably and refer to polynucleotide sequences capable of modulating the biological function of an operably linked polynucleotide sequence in a host cell. Regulatory elements for instance include sequences capable of directing or modulating (e.g. increasing) the expression of a protein product from a protein-encoding polynucleotide sequences. The term thus covers elements that promote or regulate transcription, including promoters, core elements required for basic interaction of RNA polymerase and transcription factors, upstream elements, enhancers, and response elements. Regulatory elements that are capable of directing expression in prokaryotes include promoters, operator sequences and a ribosome binding sites. The present invention envisions gene therapy of mammalian hosts, and therefore regulatory elements useful in eukaryotic cells are of particular interest. Such regulatory elements include, without limitation, promoters, enhancers, splicing signals and polyadenylation signals as further described below. Regulatory elements can be of genomic (e.g. viral or eukaryotic) origin or synthetically generated. Commonly used regulatory sequences (such as promoters, enhancers, splice, and polyadenylation sites) of viral origin are derived from Polyoma virus, Adenovirus 2, Simian Virus 40 (SV40), avian sarcoma virus (ASV) and human cytomegalovirus. Preferred regulatory elements are described in detail in the following and include promoters, enhancers and selection markers.

Promoters

"Promoters" or "promoter sequences" are nucleic acid sequences located at the transcription initiation site (typically upstream or 5' of the site of transcription initiation) and initiate transcription of a particular polynucleotide sequence of interest. Promoters can be constitutive or inducible, wherein transcription is initiated only under certain physiological conditions and can be controlled depending upon the host cell, the desired level of expression, the nature of the host cell, and the like.

The choice of suitable promoters typically depend on the type of host cell intended for expression of the polynucleotide of interest and the desired level and/or circumstances of expression. Promoters of interest for use in the nucleic acid molecule described herein include eukaryotic promoters, viral promoters and synthetic promoters, e.g. the β-actin promoter, SV40 early and late promoters, immunoglobulin promoter, human cytomegalovirus (CMV) promoter, retrovirus promoters, and others. The promoter may or may not be associated with enhancers, wherein the enhancers may be naturally associated with the particular promoter or associated with a different promoter.

Enhancers

The term "enhancer" refers to a cis-acting nucleic acid sequence, which enhances the transcription of a polynucleotide sequence and functions in an orientation and position-independent manner. The enhancer can function in any location, either upstream or downstream relative to the transcription initiation site. The enhancer may be any nucleic acid sequence, which is capable of increasing the level of transcription from the promoter when the enhancer is operably linked to the promoter. The choice of suitable enhancers typically depends on the type of host cell intended for expression of the polynucleotide sequence of interest, the employed promoter and the desired level and/or circumstances of expression. Exemplary enhancers the RSV LTR enhancer, baculovirus HR1, HR2 or HR3 enhancers or the CMV immediate early gene product enhancer.

Markers and Other Elements

A marker can be included in order to enable the detection or selection of host cells that have been successfully transformed with (i.e. comprise) the nucleic acid molecule and/or vector of the invention. A marker is typically a gene, which, upon being introduced into the host cell, expresses a dominant phenotype permitting positive selection or detection of cells carrying the gene. Genes of this type are known in the art, and include, inter alia, green fluorescent protein (GFP), yellow fluorescent protein (YFP), red fluorescent protein (REP), luciferase, beta-galactosidase (beta-Gal), beta-glucuronidase, hygromycin-B phosphotransferase gene (hph), the aminoglycoside phosphotransferase gene (neo or aph), the dihydrofolate reductase (DHFR) gene, the adenosine daminase gene (ADA), and the multi-drug resistance (MDR) gene.

Further regulatory elements of interest include an origin of replication that confers the ability to replicate in a desired host cell. Optionally, the nucleic acid molecule may comprise regulatory elements, which effect ligation or insertion into a desired host cell.

Vectors

It is conceivable to use the nucleic acid molecules of the invention for a variety of research or therapeutic applications. In particular, said nucleic acid molecules are envisaged for gene therapy. "Classical" gene therapy involves the introduction of a nucleic acid molecule comprising a polynucleotide sequence of interest into a host cell. To this end, the nucleic acid molecule is often incorporated into a "vector" (also referred to herein as a "vehicle," or "construct"), i.e. a nucleic acid molecule serving as a vehicle of genetic transfer, gene expression, or replication or integration of a polynucleotide in a host cell.

In a further aspect, the present invention therefore provides a vector comprising the nucleic acid molecule of the invention.

A vector can be an artificial chromosome or plasmid, and can be integrated into the host cell genome or exist as an independent genetic element (e.g., episome, plasmid). A vector can exist as a single polynucleotide or as two or more separate polynucleotides. Vectors according to the present invention can be single copy vectors or multicopy vectors (indicating the number of copies of the vector typically maintained in the host cell). Vectors are typically recombinant, i.e. artificial molecules which do not occur in nature. The vector can generally be a DNA or RNA vector present in linear or in circular form, depending on type of vector or type of application. Some circular nucleic acid vectors can be intentionally linearized prior to delivery into a cell.

The term "vector" includes storage vectors, cloning vectors, transfer vectors, expression vectors and the like. A "storage vector" is a vector which allows the convenient storage of a nucleic acid molecule. A "cloning vector" (also referred to as a "shuttle vector") is typically a vector that contains a cloning site containing multiple restriction endonuclease target sequences, which may be used to incorporate nucleic acid molecules into the vector. A cloning vector may be, e.g., a plasmid vector or a bacteriophage vector. A "transfer vector" may be a vector which is suitable for transferring nucleic acid molecules into cells or organisms, for example, viral vectors. An "expression vector" is a vector that is capable of effecting the expression of an expression product—such as a nucleic acid molecule or typically a protein—encoded by one or more polynucleotide sequences carried by the vector when it is present in the appropriate environment. As will be readily understood, the above definitions may overlap to a certain degree, e.g. some viral transfer vectors can also function as expression vectors.

The present invention thus also relates to a vector comprising the nucleic acid molecule described herein.

Expression Vector

Preferably, the vector is an expression vector. Said expression vector is envisaged to be capable of driving and preferably increasing the expression of BZA1B, PSIP1 and/or TSN in a desired host cell, which is preferably a T cell. Introduction of the expression vector of the invention into said T cell preferably renders the T cell more responsive to L-arginine or (other) BPT ligands and promotes favorable T cell functions (including enhanced survival and effector activity).

Any of the methods known in the art for the insertion of polynucleotide sequences into a vector "backbone" may be used to construct expression vectors comprising the nucleic acid of the invention. These methods may include in vitro recombinant DNA and synthetic techniques and genetic recombination. The polynucleotide sequence(s) of interest are typically inserted into the vector in the form of an "expression cassette" consisting of said polynucleotide sequence(s) of interest and of appropriate regulatory elements for their expression. The resulting vector is referred to as a "recombinant" vector because it comprises novel combinations of nucleic acid sequences from the donor genome with the vector nucleic acid sequence. Recombinant vectors comprising the desired polynucleotide sequence can be identified by known techniques including (a) nucleic acid hybridization; (b) presence or absence of "marker" gene functions; and (c) expression of inserted sequences. The vector may comprise additional regulatory elements in its "backbone", e.g. an origin of replication, enhancers, restriction sites, or regulatory elements as described elsewhere herein. The vector may therefore comprise regulatory sequences directing its ligation and integration into the host cell genome etc. It will be understood that the specific design of the expression vector may depend on such factors as the choice of the host cell and the desired amount of the particular expression product, etc.

Types of Vectors

The vector can be a viral or in a non-viral vector. Non-viral vectors include plasmids (integrating or non-integrating), plasmid mini-circles, transposons, cosmids and artificial chromosomes. Such non-viral vectors can be complexed with polymers or lipids or can be provided in the form of "naked" RNA or DNA.

Viral vectors include retroviruses, herpes viruses, lentiviruses, adenoviruses and adeno-associated viruses. Retroviruses, lentiviruses and adeno-associated viruses integrate into host cell DNA and therefore have potential for long term expression in the host. Retroviruses may be selected from murine leukaemia virus (MLV), mouse mammary tumour virus (MMTV), Rouse sarcoma virus (RSV), Moloney murine leukaemia virus (Mo MLV), Fujinami sarcoma virus (FuSV), Moloney murine sarcoma virus (Mo-MSV), Abelson murine leukaemia virus (A-MLV) and Avian erythroblastoma virus (AEV). Lentiviruses may be selected from human immunodeficiency virus (HIV), simian immunodeficiency virus (SIV), feline immunodeficiency virus (Fly), equine infectious anaemia virus (EIAV), caprine arthritis encephalitis virus (CAEV), bovine immunodeficiency virus (BIV) and Jembrana disease virus ODV) based vectors. Adenoviruses may be selected from adenovirus type 5 first and second generation and gutless vectors. Adeno-associated viruses may be selected from all adeno-associated serotypes.

The choice of a suitable expression vector depends inter alia on the host cell intended for expression of the encoded polypeptide sequence(s). As explained previously, expression vectors described herein are considered to be useful for enhancing the expression of the transcriptional regulators BZAB1, PSIP1 and/or TSN which the present inventors identified as important regulators of T cell survival and effector functions. The expression vectors are therefore generally useful for various in vitro methods (and may then be selected for their capability of effectively transforming T cells in order to achieve an increased expression of BZAB1, PSIP1 and/or TSN) and/or for in vivo applications (wherein suitable expression vectors are additionally selected for their safety and therapeutic efficacy when administered to the subject to be treated).

In Vitro Applications

The present invention therefore further relates to an in vitro method of introducing the nucleic acid molecule and/or the vector described herein into a desired host cell, preferably a T cell.

The nucleic acid molecule or vector can be introduced into the host cell using any "transformation" method known in the art. The terms "transduction", "transfection" and "transformation" are used interchangeably herein to refer to the introduction of exogenous (foreign) nucleic acid molecules or vectors into a host cell. Transformation may rely on any known method for the insertion of nucleic acid molecules and/or vectors into a prokaryotic or eukaryotic host cell. The method is selected based on the type of host cell being transformed and may include, but is not limited to, viral infection, electroporation, heat shock, lipofection, calcium phosphate transfection, protoplast fusion and particle bombardment. "Transformed" cells include stably transformed cells in which the inserted nucleic acid molecule or vector is capable of replication either as an autonomously replicating episomal entity or as part of the host cell chromosome. Also included are cells that transiently express the polypeptide sequence(s) of interest. "Transformed" host cells therefore comprise the nucleic acid molecule and/or vector of the invention and/or the polynucleotide sequence(s) delivered by said nucleic acid molecule and/or vector.

The nucleic acid molecule and/or vector of the invention is envisaged to modulate, in particular increase the expression of BZAB1, PSIP1 and/or TSN in the host cell. The host cell is preferably a T cell as defined elsewhere herein. Host cells comprising the nucleic acid molecule or vector described herein therefore preferably exhibit an increased responsiveness towards L-arginine or (other) BPT ligands.

The in vitro method described above may further comprise a step of activating the T cells (e.g. by contacting the cells with an anti-CD3 and/or anti-CD28 antibody that is optionally immobilized and/or an MHC-I or MHC-II bound antigen optionally presented by an antigen-presenting cell and/or cytokines such as IL-2 or other molecules as exemplified elsewhere herein). The method may comprise a step of enriching a particular T cell subset (e.g. by sorting for a particular cell surface marker such as CD4 or CD8). The method may comprise a step of screening the T cells for their binding specificity towards a preselected antigenic target. The method may comprise a step of genetically modifying the T cells for expression of a recombinant T cell receptor (TCR) or chimeric antigen receptor (CAR) or other effector molecules such as inducible suicide molecules.

T cells subjected to genetic modifications and/or treatments such as those described above are particularly envisaged for use in a method of ACT. That is, host cells may be obtained from a suitable donor, and subsequently be cultivated, activated, enriched, screened and/or genetically engineered as described herein. Subsequently, said host cells are typically re-introduced into the patient.

Host Cells

The present invention further features a host cell comprising the nucleic acid molecule and/or vector according to the invention.

As used herein, the term "host cell" refers to a cell into which a nucleic acid molecule and/or a vector according to the invention has been introduced, and which preferably enables the expression of the polynucleotide sequence of interest from the nucleic acid molecule and/or vector. The host cell thus comprises the nucleic acid molecule and/or vector containing polynucleotide sequence(s) of interest.

Accordingly, the host cell be a transformed host cell as described above.

It should be understood that the term "host cell" does not only refer to the particular subject cell but to the progeny or potential progeny of such a cell. As BAZ1B, PSIP1 and TSN are suggested as important modulators of T cell function, the host cell is preferably a T cell as defined elsewhere herein. The term "T cell" includes primary T cells, secondary T cells and T cell lines.

Host cells comprising the nucleic acid molecule and/or vector described herein (also referred to as "engineered host cells") are envisaged to exhibit an increased responsiveness to L-arginine or (other) BPT ligands. Host cells having this property can advantageously be employed in various research or therapeutic applications as described below. It is for instance envisaged that T cells comprising the vector described herein exhibit an enhanced survival capacity and/or effector functions. Such T cells be used for in vitro research applications, but also hold a considerable potential for treatment of diseases that would benefit from modulation of T cell mediated responses in vivo. It is specifically envisaged to employ such engineered host cells with an increased sensitivity towards L-arginine or (other) BPT ligands in methods of ACT, e.g. for treating cancer and/or infection.

Gene Therapy

In a further aspect, the present invention also provides nucleic acid molecules and/or vectors of the invention for use in gene therapy.

"Gene therapy" involves modulating (i.e. restoring, enhancing, decreasing or inhibiting) gene expression in a subject in order to achieve a therapeutic effect. To this end, gene therapy typically encompasses the introduction of foreign nucleic acids (such as DNA, e.g. in the form of genes, or RNA, e.g. siRNA) into cells. The term generally refers to the manipulation of a genome for therapeutic purposes and includes the use of genome-editing technologies for correction of mutations that cause disease, the addition of therapeutic genes to the genome as well as the removal of deleterious genes or genome sequences. In the context of the present invention, gene therapy can be used to enhance the expression of BAZ1B, PSIP1 and/or TSN in target cells (particularly T cells) or to decrease the expression of inhibitors of BAZ1B, PSIP1 and/or TSN or their ligands in order to modulate T cell function and in consequence T cell mediated immune responses.

Gene therapy may involve in vivo or ex vivo transformation of the host cells. Thus, the gene therapy methods according to the invention may comprise the step of (a)

introducing a nucleic acid molecule and/or vector of the invention into a host cell in vivo; or (b) introducing a nucleic acid molecule and/or vector of the invention into a host cell ex vivo and optionally re-introducing the host cell into the subject that served as a donor for said host cell or into another suitable subject. The host cells are preferably T cells. Gene therapy methods according to the invention are envisaged to increase responsiveness of T cells to L-arginine and/or (other) BPT ligands and thereby—inter alia—to promote favorable T cell responses including an increased survival in the host and the generation of memory T lymphocytes (in particular $T_{CM}$) which are capable of boosting an effective secondary immune response upon re-exposure to their cognate antigen.

Ex Vivo Transformation

The gene therapy method according to the invention may involve a step of ex vivo transforming appropriate host cells (preferably T cells) with a nucleic acid molecule and/or vector of the invention. The host cells (preferably T cells) are typically obtained from a subject/donor. Ex vivo transformation in the gene therapy method of the invention may further comprise one or more of the following steps: (i) cultivating the host cells; and (ii) introducing a nucleic acid molecule and/or vector according to the invention into a host cell ex vivo, thereby obtaining transformed host cells (i.e. host cells comprising the nucleic acid molecule and/or vector according to the invention). Transformation of the host cells can be accomplished using any of the techniques described elsewhere herein.

Subsequently, the transformed host cells are typically re-introduced into the subject/donor (autologous transfer) or into another suitable recipient (allogenic transfer). The transformed host cells are preferably administered to the subject in the form of a suitable pharmaceutical composition as described below. If desired, the transformed host cells may be lethally irradiated or treated otherwise in order to abrogate their proliferative potential before being re-introduced into the subject.

In Vivo Transformation

The gene therapy method according to the invention may involve a step of in vivo transforming appropriate host cells (preferably T cells) with a nucleic acid molecule and/or vector of the invention.

Therefore, the nucleic acid molecule and/or vector of the invention is introduced into appropriate host cells (preferably T cells) in vivo. In vivo transformation thus involves the administration of a nucleic acid molecule and/or a vector of the invention to a subject.

Introduction is typically accomplished by administering said nucleic acid molecule and/or vector to the subject in a form that is safe and effective for in vivo transformation and enables expression of the polynucleotide sequence(s) encoding the polypeptides or nucleic acids of interest (e.g. BAZ1B, PSIP1 or TSN) in the subject.

To this end, viral vectors as exemplified elsewhere herein are particularly suitable. Some viral vectors exhibit a natural tropism towards the desired host cells (e.g. T cells) or can be modified accordingly.

The nucleic acid molecule and/or vector of the invention may be administered in the form of a pharmaceutical composition as described below. It is conceivable to administer the nucleic acid molecule and/or vector (or a pharmaceutical composition comprising the same) locally, for instance by injection to the site of interest.

Gene therapy, including a step of in vivo and/or ex vivo transformation of appropriate host cells as described above, are envisaged to render the transformed host cells more sensitive (or responsive) towards L-arginine and/or (other) BPT ligands. The transformed host cells are preferably T cells. It is envisioned that an increased responsiveness towards L-arginine and/or (other) BPT ligands promotes favorable biological functions in the host cell. Specifically, the transformed T cells may exhibit an increased survival capacity in the treated subject and/or increased effector functions (e.g. anti-tumor activity).

In view of the above, the present invention thus features a nucleic acid molecule, a vector and/or a host cell according to the invention for use in a method of gene therapy.

Transformation of host cells ex vivo or in vivo with a nucleic acid molecule and/or vector according to the invention may be part of an ACT approach. Endowing T cells intended for use in ACT e.g. with an increased BAZ1B, PSIP1 and/or TSN expression (by transforming said T cells with a nucleic acid molecule and/or vector according to the invention) is envisaged to enhance the ability of said T cells to survive in the host. Thereby, the nucleic acid molecules and/or vectors according to the invention may aid in overcoming the common problem of low persistence of reinfused T cell in vivo. In a further aspect, the present invention therefore provides a nucleic acid molecule, a vector and/or a host cell according to the invention for use in adoptive cell therapy (ACT).

Transformation of host cells (preferably T cells) with the nucleic acid molecules and/or vectors according to the invention preferably results in an increased sensitivity towards L-arginine or (other) BPT ligands—which is, in turn, expected to affect the biological functions of the transformed T cell and therefore immune responses mediated by said T cell. In a further aspect, the present invention thus provides a nucleic acid molecule, a vector and a host cell according to the invention for use in a method of modulating, preferably enhancing, a T cell mediated immune response in a subject. As indicated elsewhere herein, T cell mediated immune responses of particular interest include anti-cancer responses and anti-infection responses. Accordingly, the present invention further provides a nucleic acid molecule, a vector and a host cell according to the invention for use in a method of treating cancer and/or infection in a subject.

Pharmaceutical Composition

L-arginine, BPT ligands, nucleic acid molecules, vectors and/or host cells disclosed herein can be formulated into a pharmaceutical composition for administration to a subject in need thereof. The pharmaceutical composition is thus envisaged to comprise as an active (or therapeutic) agent at least one of the following: (1) L-Arginine (2) (other) BPT ligands, (3) a nucleic acid molecule of the invention, (4) a vector comprising said nucleic acid molecule and/or (5) a host cell comprising said nucleic acid molecule and/or said vector.

Excipients

The pharmaceutical composition may optionally comprise one or more pharmaceutically acceptable excipients. The term "pharmaceutically acceptable" refers to a compound or agent that is compatible with the one or more active agent(s) and does not interfere with and/or substantially reduce their pharmaceutical activities. Pharmaceutically acceptable excipients preferably have sufficiently high purity and sufficiently low toxicity to make them suitable for administration to a person to be treated. Pharmaceutically acceptable excipients can exhibit different functional roles and include, without limitation, diluents, fillers, bulking agents, carriers, disintegrants, binders, lubricants, glidants, coatings, solvents and co-solvents, buffering agents, preservatives, adjuvants, anti-oxidants, wetting agents, anti-foaming agents, thickening agents, sweetening agents, flavouring agents and humectants. The choice of suitable pharmaceutical excipients depends inter alia on the formulation of the pharmaceutical composition.

For pharmaceutical compositions in liquid form, useful pharmaceutically acceptable excipients include solvents, diluents or carriers such as (pyrogen-free) water, saline solutions such phosphate or citrate buffered saline, fixed oils, vegetable oils, such as, for example, groundnut oil, cottonseed oil, sesame oil, olive oil, corn oil, ethanol, polyols (for example, glycerol, propylene glycol, polyethylene glycol, and the like); lecithin; surfactants; preservatives such as benzyl alcohol, parabens, chlorobutanol, phenol, ascorbic acid, thimerosal, and the like; isotonic agents such as sugars, polyalcohols such as mannitol, sorbitol, or sodium chloride; aluminum monostearate or gelatin; antioxidants such as ascorbic acid or sodium bisulfite; chelating agents such as ethylenediaminetetraacetic acid (EDTA); buffers such as acetates, citrates or phosphates and agents for the adjustment of tonicity such as sodium chloride or dextrose. pH can be adjusted with acids or bases, such as hydrochloric acid or sodium hydroxide.

Liquid pharmaceutical compositions administered via injection and in particular via i.v. injection should be sterile and stable under the conditions of manufacture and storage. Such compositions are typically formulated as parenterally acceptable aqueous solutions that are pyrogen-free, have suitable pH, are isotonic and maintain stability of the active ingredient(s). Exemplary useful excipients for such formulations include physiological saline, pyrogen-free water and/ or 0.9% NaCl or and suitable mixtures thereof.

For pharmaceutical composition in solid form, useful pharmaceutically acceptable excipients include binders such as microcrystalline cellulose, gum tragacanth or gelatin; starch or lactose; sugars, such as, for example, lactose, glucose and sucrose; starches, such as, for example, corn starch or potato starch; cellulose and its derivatives, such as, for example, sodium carboxymethylcellulose, ethylcellulose, cellulose acetate; disintegrants such as alginic acid; lubricants such as magnesium stearate; glidants such as stearic acid, magnesium stearate; calcium sulphate, colloidal silicon dioxide and the like; sweetening agents such as sucrose or saccharin; and/or flavoring agents such as peppermint, methyl salicylate, or orange flavoring.

Formulation

The pharmaceutical composition can be provided in various formulations depending on the desired route of administration. Oral formulations can be provided in the form of a tablet, a capsule, a liquid, a powder or in a sustained release format. Parenteral formulations are typically provided in liquid or in lyophilized form which is reconstituted with a suitable liquid diluent before being administered. Parenteral formulations are thus typically stored in vials, IV bags, ampoules, cartridges, or prefilled syringes and can be administered as injections, inhalants, or aerosols. Topical formulations are provided in the form of a cream, ointment, gel, paste or powder.

Routes of Administration

The pharmaceutical composition can be administered, for example, systemically or locally.

Systemic administration is achieved, for example, via parenteral routes (e.g. via injection and/or infusion), such as intravenous, intra-arterial, intraosseous, intramuscular, subcutaneous, intradermal, transdermal, or transmucosal routes, etc., and enteral routes (e.g. as tablets, capsules, suppositories, via feeding tubes, gastrostomy), such as oral, gastrointestinal or rectal routes, etc. . . . . Preferred routes of systemic administration are intravenous, intramuscular, subcutaneous, oral and rectal administration, whereby intravenous and oral administration are particularly preferred.

Topical administration typically refers to application to body surfaces such as the skin or mucous membranes, whereas the more general term "local administration" additionally comprises application in and/or into specific parts of the body. Routes for local administration also include, for example, inhalational routes, such as nasal, or intranasal routes, administration through the mucous membranes in the body, etc., or other routes, such as epidermal routes, epicutaneous routes (application to the skin) or patch delivery and other local application, e.g. injection anchor infusion, into the organ or tissue to be treated etc. Local administration can be useful to avoid undesired side effects. However, certain routes of administration may provide both, a local and a systemic effect, for example inhalation.

A liquid pharmaceutical composition can be administered by various methods, for example as a spray (e.g., for inhalational, intranasal etc. routes), as a fluid for topical application, by injection, including bolus injection, by infusion, for example by using a pump, by instillation, but also p.o., e.g. as drops or drinking solution, in a patch delivery system etc. Accordingly, for the administration different devices may be used, in particular for injection and/or infusion, e.g. a syringe (including a pre-filled syringe); an injection device (e.g. the INJECT-EASET™ and GENJECTT™ device); an infusion pump (such as e.g. Accu-Chek™); an injector pen (such as the GENPENT™); a needleless device (e.g. MEDDECTOR™ and BIOJECTOR™); or an autoinjector.

The present inventors discovered that L-arginine is advantageously therapeutically effective when administered orally. Oral administration is associated with high levels of patient acceptance and long term compliance and carries the lowest cost. For instance, oral administration of L-arginine has been demonstrated to increase intracellular L-arginine levels and T cell survival in vivo (cf. the appended Examples). Some (other) BPT ligands (e.g. peptides) as well as other active ingredients of the inventive pharmaceutical composition (such as host cells, nucleic acid molecules and vectors) may suitably be administered parenterally, e.g. topically or via i.v. or local (e.g. intra-tumoral) injection.

Dosage

Preferably, L-arginine, (other) BPT ligands, nucleic acid molecule, vector and/or host cell ("active agent(s)") according to the invention are administered to the subject in a therapeutically effective amount. A "therapeutically effective amount", as used herein, is the amount which is sufficient for the alleviation of the symptoms of the disease or condition being treated and/or for prophylaxis of the symptoms of the disease or condition being prevented. In other words, a "therapeutically effective amount" means an amount of the active ingredient that is sufficient to significantly induce a positive modification of a disease or disorder, i.e. an amount of the active ingredient, that elicits the biological or medicinal response in a tissue, system, animal or human that is being sought. Therapeutic efficacy and toxicity of the active agents provided herein can be determined by standard pharmaceutical procedures in cell cultures or experimental animals, e.g., for determining the LD50 (the dose lethal to 50% of the population) and the ED50 (the dose therapeutically effective in 50% of the population). The close ratio between toxic and therapeutic effects is the therapeutic index and can be expressed as the ratio LD50/ED50. Active agents which exhibit large therapeutic indices are generally preferred. The data obtained from the cell culture assays and animal studies can be used in formulating a range of dosage for use in humans. The dosage of such compounds lies preferably within a range of circulating concentrations that include the ED50 with little or no toxicity.

The term also includes the amount of the active agent(s) sufficient to reduce the progression of the disease, for instance to reduce or inhibit the tumor growth or infection. At the same time, however, a "therapeutically effective amount" is preferably small enough to avoid serious side-effects, that is to say to permit a sensible relationship between advantage and risk. The determination of these limits typically lies within the scope of sensible medical judgment. A "therapeutically effective amount" of the active agent(s) will furthermore vary in connection with the particular disease or condition to be treated, characteristics of the patient (including age, physical condition, body weight, sex and diet), concurrent treatments, pharmacokinetic properties of the active agent(s), treatment regime and the desired effect (amelioration vs. complete remission), etc.

For instance, therapeutically effective closes of the active agent(s) described herein may range from about 0.001 mg to 10 mg, preferably from about 0.01 mg to 5 mg, more preferably from about 0.1 mg to 2 mg per dosage unit or from about 0.01 nmol to 1 mmol per dosage unit, in particular from 1 nmol to 1 mmol per dosage unit, preferably from 1 µmol to 1 mmol per dosage unit. It is also envisaged that the therapeutically effective dose of the active agent(s) may range (per kg body weight) from about 0.01 mg/kg to 10 g/kg, preferably from about 0.05 mg/kg to 5 g/kg, more preferably from about 0.1 mg/kg to 2.5 g/kg.

Treatment Regime

The active ingredient(s) may be administered to the patient several times a day, daily, every other day, weekly, or monthly.

Combination Therapy

A pharmaceutical composition may be administered alone or in combination with other active agents, either simultaneously or sequentially. Said other active agents are preferably useful for treating the same desired condition or disease as the active agent(s) or pharmaceutical composition of the invention include e.g. anti-cancer agents or anti-infection agents. Said agents are also referred to as "additional active agents" herein. The pharmaceutical composition can be combined together with additional active agents in one pharmaceutical formulation. Alternatively, the additional active agents can be provided in pharmaceutical formulations for separate (simultaneous or sequential) administration via the same or different administration routes.

For instance, L-arginine and (other) OPT ligands described herein have been shown to be effective for treatment of cancer (cf. the appended examples). Thus, additional active agents to be used in combination therapy include "anti-cancer agents" (also referred to as "anti-neoplastic agents"). Such anti-cancer agents can be grouped into several categories, namely, alkylating agents (including nitrogen mustards such as mechlorethamine, cyclophosphamide, melphalan, chlorambucil, ifosfamide and busulfan; nitrosoureas such as N-Nitroso-N-methylurea (MNU), carmustine (BCNU), lomustine (CCNU) and semustine (MeCCNU), fotemustine and streptozotocin; tetrazines such as dacarbazine, mitozolomide and temozolomide; aziridines such as thiotepa, mytomycin and diaziquone (AZQ); cisplatin and derivatives such as cisplatin, carboplatin and oxaliplatin or others such as procarbazine and hexamethylmelamine), antimetabolites (including anti-folates such as methotrexate and pemetrexed; fluoropyrimidines such as fluorouracil and capecitabine; deoxynucleoside analogues such as cytarabine, gemcitabine, decitabine, fludarabine, nelarabine, cladribine, clofarabine and pentostatin; thiopurines such as thioguanine and mercaptopurine), anti-microtubule agents (including *vinca* alkaloids such as vincristine and vinblastine; semi-synthetic *vinca* alkaloids such as vinorelbine, vindesine and vinflunine; taxanes such as paclitaxel and docetaxel; lignans such as podophyllotoxin), topoisomerase inhibitors (including irinotecan, topotecan, etoposide, doxorubicin, mitoxantrone, teniposide, novobiocin, merbarone and aclarubicin), and cytotoxic antibiotics (including anthracyclines such as doxorubicin, daunorubicin, epirubicin, idarubicin, pirarubicin, aclarubicin, mitoxantron; bleomycins; mitomycin C; mitoxantrone; actinomycin) or combinations thereof.

The active agent(s) described herein are also envisaged for treating infections caused by a variety of pathogenic microorganisms including bacteria, viruses, protozoa and fungi. Therefore, it is also conceivable to use a variety of "anti-infection agents" as additional active agents in combination therapy together with the pharmaceutical composition of the invention. "Anti-infection agents" or "anti-infectives" are agents effective for killing and/or inhibiting the growth of infective microorganism or populations of such microorganisms and include antibiotics, anti-fungal, anti-viral and anti-protozoal agents. As used herein, "antibiotic" means an antibacterial agent. "Antibiotics" are antibacterial agents that may have bacteriostatic or bacteriocidal activity. Non-limiting examples of antibiotics that may be used in combination therapy include tetracyclines (e.g. minocycline), rifamycins (e.g. rifampin), macrolides (e.g. erythromycin), penicillins (e.g. nafcillin), cephalosporins (e.g. cefazolin), other beta-lactam antibiotics (e.g. imipenem, aztreonam), aminoglycosides (e.g. gentamicin), chloramphenicol, sulfonamides (e.g. sulfamethoxazole), glycopeptides (e.g. vancomycin), quinolones (e.g. ciprofloxacin), fusidic acid, trimethoprim, metronidazole, clindamycin, mupirocin, polyenes (e.g. amphotericin B), azoles (e.g. fluconazole) and beta-lactam inhibitors (e.g. sulbactam). Nonlimiting examples of specific antibiotics that may be used include minocycline, rifampin, erythromycin, nafcillin, cefazolin, imipenem, aztreonam, gentamicin, sulfamethoxazole, vancomycin, ciprofloxacin, trimethoprim, metronidazole, clindamycin, teicoplanin, mupirocin, azithromycin, clarithromycin, ofloxacin, lomefloxacin, norfloxacin, nalidixic acid, sparfloxacin, pefloxacin, amifloxacin, enoxacin, fleroxacin, temafloxacin, tosufloxacin, clinafloxacin, sulbactam, clavulanic acid, amphotericin B, fluconazole, itraconazole, ketoconazole, and nystatin, or combinations thereof. "Anti-viral agents" include anti-viral immunoglobulins and binding peptides, biomimetic peptides, chemokine receptor antagonistst (e.g. maraviroc), nucleoside analogues (e.g. acyclovir, ganciclovir, dideoxyinosine, dideoxycytidine, zidovudine, lamuvidine), anti-viral interferons (e.g. IFN-alpha, IFN-beta), adamantane antivirals (e.g. amantadine, rimantadine), viral enzyme inhibitors (e.g. non-nucleoside reverse transcriptase inhibitors (NNRTIs), nucleoside reverse transcriptase inhibitors (NRTIs), protease inhibitors, neuramidase inhibitors, integrase strand transfer inhibitor), NS5A inhibitors, antiviral boosters (e.g. ritonavir, cobicistat) or others (e.g. sofosbuvir, enfuvirtide, foscarnet, fomivirsen). "Anti-fungal agents" or "antimycotics" include polyenes (e.g. amphotericin B, candicidin, filipin, hamycin, natamycin, nystatin), imidazoles (e.g. ifonazole, butoconazole, and clotrimazole), triazoles (e.g. isoconazole, fluconazole, itraconazole, ketoconazole), thiazoles (abafungin), allylamines (e.g. amorolfin, butenafine, naftifine), echinocandins (e.g. anidulafungin, caspofungin, micafungin) and others (e.g. benzoic acid, ciclopirox, flucytosine or 5-fluorocytosine, griseofulvin, tolnaftate, undecylenic acid). "Anti-protozoal agents" include eflornithine, furazolidone, melarsoprol, metronidazole, nifursemizone, nitazoxanide, ornidazole, paromomycin sulfate, pentamidine, pyrimethamine, tinidazole).

Further additional agents include agents supporting immune cell proliferation, survival, differentiation and/or effector functions in vivo, e.g. various cytokines (e.g. IL-2, IL-3, IL-6, IL-11, IL7, IL12, IL15, IL21 alpha, beta or gamma interferon) or growth factors (e.g. granulocyte macrophage colony stimulating factor), and erythropoietin.

The aforementioned additional active agents are envisaged for use in combination therapy with the pharmaceutical compositions provided herein. Combination therapy can involve the use of one additional active agent or combinations thereof, depending on the condition and severity to be treated.

Treatment

L-arginine, BPT ligands, nucleic acid molecules, vectors, host cells and pharmaceutical compositions of the invention are useful for modulating and preferably enhancing T cell mediated immune responses. The aforementioned agents are therefore inter alia useful for treatment, amelioration and/or prophylaxis of diseases which would benefit from stimulation of T cell mediated immune responses in a subject in need thereof.

The term "treatment" or "treating" of a disease includes preventing or protecting against the disease (that is, causing the clinical symptoms not to develop); inhibiting the disease (i.e., arresting or suppressing the development of clinical symptoms; and/or relieving the disease (i.e., causing the regression of clinical symptoms). As will be appreciated, it is not always possible to distinguish between "preventing" and "suppressing" a disease or disorder since the ultimate inductive event or events may be unknown or latent. Accordingly, the term "prophylaxis" will be understood to constitute a type of "treatment" that encompasses both "preventing" and "suppressing." The term "treatment" thus includes "prophylaxis".

Such conditions and disorders include cancer and infection.

The term "subject", "patient" or "individual" as used herein generally includes humans and non-human animals and preferably mammals (e.g., non-human primates, including marmosets, tamarins, spider monkeys, owl monkeys, vervet monkeys, squirrel monkeys, and baboons, macaques, chimpanzees, orangutans, gorillas; cows; horses; sheep; pigs; chicken; cats; dogs; mice; rat; rabbits; guinea pigs; etc.), including chimeric and transgenic animals and disease models. In the context of the present invention, the term "subject" preferably refers a non-human primate or a human, most preferably a human.

As used herein, the term "cancer" refers to a neoplasm or tumor resulting from abnormal uncontrolled growth of cells. Cancer includes benign tumors, which remain localized, and malignant tumors, which invade and destroy neighboring body structures and spread to distant sites by metastasis. Cancer may be associated with a specific cancer antigen that is expressed on cancer cells (also referred to as tumor-associated antigens, or TAA). In ACT, it is possible to enrich for T cells specifically recognizing TAAs, or to provide T cells with TAA specificity by genetic engineering (e.g. by endowing T cells with recombinant TAA-specific TCRs or CARs). Similarly, T cells can be selected for or endowed with antigen specificity against pathogens causing infection. L-arginine or PPT ligands can be used to promote T cell survival and anti-cancer activity in vitro and in vivo.

Examples of cancers which the present invention can be used to prevent or treat include solid tumours and leukaemias, including: apudoma, choristoma, branchioma, malignant carcinoid syndrome, carcinoid heart disease, carcinoma (e.g., Walker, basal cell, basosquamous, Brown-Pearce, ductal, Ehrlich tumour, in situ, Krebs 2, Merkel cell, mucinous, non-small cell lung, oat cell, papillary, scirrhous, bronchiolar, bronchogenic, squamous cell, and transitional cell), histiocytic disorders, leukaemia (e.g., B cell, mixed cell, null cell, T cell, T-cell chronic, HTLV-II-associated, lymphocytic acute, lymphocytic chronic, mast cell, and myeloid), histiocytosis malignant, Hodgkin disease, immunoproliferative small, non-Hodgkin lymphoma, plasmacytoma, reticuloendotheliosis, melanoma, chondroblastoma, chondroma, chondrosarcoma, fibroma, fibrosarcoma, giant cell tumours, histiocytoma, lipoma, liposarcoma, mesothelioma, myxoma, myxosarcoma, osteoma, osteosarcoma, Ewing sarcoma, synovioma, adenofibroma, adenolymphoma, carcinosarcoma, chordoma, cranio-pharyngioma, dysgerminoma, hamartoma, mesenchymoma, mesonephroma, myosarcoma, ameloblastoma, cementoma, odontoma, teratoma, thymoma, trophoblastic tumour, adeno-carcinoma, adenoma, cholangioma, cholesteatoma, cylindroma, cystadenocarcinoma, cystadenoma, granulosa cell tumour, gynandroblastoma, hepatoma, hidradenoma, islet cell tumour, Leydig cell tumour, papilloma, Sertoli cell tumour, theca cell tumour, leiomyoma, leiomyosarcoma, myoblastoma, mymoma, myosarcoma, rhabdomyoma, rhabdomyosarcoma, ependymoma, ganglioneuroma, glioma, medulloblastoma, meningioma, neurilemmoma, neuroblastoma, neuroepithelioma, neurofibroma, neuroma, paraganglioma, paraganglioma nonchromaffin, angiokeratoma, angiolymphoid hyperplasia with eosinophilia, angioma sclerosing, angiomatosis, glomangioma, hemangioendothelioma, hemangioma, hemangiopericytoma, hemangiosarcoma, lymphangioma, lymphangiomyoma, lymphangiosarcoma, pinealoma, carcinosarcoma, chondrosarcoma, cystosarcoma, phyllodes, fibrosarcoma, hemangiosarcoma, leiomyosarcoma, leukosarcoma, liposarcoma, lymphangiosarcoma, myosarcoma, myxosarcoma, ovarian carcinoma, rhabdomyosarcoma, sarcoma (e.g., Ewing, experimental, Kaposi, and mast cell), neoplasms (e.g., bone, breast, digestive system, colorectal, liver, pancreatic, pituitary, testicular, orbital, head and neck, central nervous system, acoustic, pelvic respiratory tract, and urogenital), neurofibromatosis, and cervical dysplasia.

The term "infection" or "infectious disease" relates to the invasion and multiplication of microorganisms such as bacteria, viruses, and parasites that are not normally present within the body. An infection may cause no symptoms and be subclinical, or it may cause symptoms and be clinically apparent. An infection may remain localized, or it may spread through the blood or lymphatic system to become systemic (body wide).

For instance, infections may be caused by viruses including, but are not limited to, Retroviridae (e.g. human immunodeficiency viruses, such as HIV-1 (also referred to as HDTV-III, LAVE or HTLV-III/LAV, or HIV-III; and other isolates, such as HIV-LP; Picornaviridae (e.g. polio viruses, hepatitis A virus; enteroviruses, human Coxsackie viruses, rhinoviruses, echoviruses); Caliciviridae (e.g. strains that cause gastroenteritis); Togaviridae (e.g. equine encephalitis viruses, rubella viruses); Flaviridae (e.g. dengue viruses, encephalitis viruses, yellow fever viruses); Coronaviridae (e.g. coronaviruses); Rhabdoviridae (e.g. vesicular stomatitis viruses, rabies viruses); Filoviridae (e.g. ebola viruses); Paramyxoviridae (e.g. parainfluenza viruses, mumps virus, measles virus, respiratory syncytial virus); Orthomyxoviridae (e.g. influenza viruses); Bungaviridae (e.g. Hantaan viruses, bunga viruses, phleboviruses and Nairo viruses); Arena viridae (hemorrhagic fever viruses); Reoviridae (e.g. reoviruses, orbiviurses and rotaviruses); Birnaviridae; Hepadnaviridae (Hepatitis B virus); Parvoviricla (parvoviruses); Papovaviridae (papilloma viruses, polyoma viruses); Adenoviridae (most adenoviruses); Herpesviridae (herpes simplex virus (HSV) 1 and 2, varicella zoster virus, cytomegalovirus (CMV), herpes virus; Poxviriclae (variola viruses, vaccinia viruses, pox viruses); and Iridoviridae (e.g. African swine fever virus); and unclassified viruses (e.g. the agent of delta hepatitis (thought to be a defective satellite of hepatitis B virus), the agents of non-A, non-B hepatitis (class 1=internally transmitted; class 2=parenterally transmitted (i.e. Hepatitis C); Norwalk and related viruses, and astroviruses).

Other infections may be caused by bacteria including, without limitation, *Pasteurella, Staphylococci; Streptococcus, Escherichia Pseudomonas* species, and *Salmonella* species. Specific examples of infectious bacteria include but are not limited to, *Helicobacter pyloris, Borelia burgdorferi, Legionella pneumophilia, Mycobacteria* sps (e.g. *M. tuberculosis, M. avium, M. intracellulare, M. kansaii, M. gordonae*), *Staphylococcus aureus, Neisseria gonorrhoeae, Neisseria meningitidis, Listeria monocytogenes, Streptococcus pyogenes* (Group A *Streptococcus*), *Streptococcus agalactiae* (Group B *Streptococcus*), *Streptococcus* (*viridans* group), *Streptococcus faecalis, Streptococcus bovis, Streptococcus* (anaerobic sps.), *Streptococcus pneumoniae*, pathogenic *Campylobacter* sp., *Enterococcus* sp., *Haemophilus influenzae, Bacillus antracis, corynebacterium chphthenae, corynebacterium* sp., *Erysipelothrix rhusiopathiae, Clostridium perfringers, Clostridium tetani; Enterobacter aerogenes, Klebsiella pneumoniae, Pasteurella multocida, Bacteroides* sp., *Fusobacterium nucleatum, Streptobacillus moniliformis, Treponema pallidum, Treponema pertenue, Leptospira, Rickettsia,* and *Actinomyces israelli*

L-arginine or (other) BPT ligands, nucleic acid molecules, vectors, host cells and pharmaceutical compositions described herein are useful for treating infections of any kind, including viral infections, bacterial infections, protozoal infections and fungal infections.

Treatment of acute or chronic viral infections are particularly envisaged and include influenza, HIV, cytomegalovirus (CMV), Epstein-Barr (EBV), Hepatitis B (HBV) and Hepatitis C (HCV) infections.

Method

The invention also features a method of modulating a T cell mediated immune response in a subject comprising administering (i) L-arginine or (other) BAZ1B, PSIP1 and/or TSN ligands and/or (ii) a nucleic acid molecule and/or (iii) a vector and/or (iv) a host cell and/or (v) a pharmaceutical composition as described herein to a subject. Further provided herein is a method of treating cancer and/or infection in a subject comprising administering i) L arginine or (other) BAZ1B, PSIP1 and/or TSN ligands and/or (ii) a nucleic acid molecule and/or (iii) a vector and/or (iv) a host cell and/or (v) a pharmaceutical composition as described herein to a subject.

The definitions and embodiments provided in the context of L-arginine, the BPT ligands, nucleic acids, vectors, host cells, pharmaceutical compositions and uses of the invention are equally applicable to the methods of treatment, mutatis mutandis.

The invention particularly comprises the following items:

1. L-arginine for use in a method of modulating a T cell mediated immune response in a subject.
2. L-arginine for the use according to item 1, wherein in said method of modulating a T cell mediated immune response the T cell mediated immune response is enhanced.
3. L-arginine for the use according to item 1 or 2, wherein said T-cell mediated immune response is a T cell mediated anti-cancer response or a T cell mediated anti-infection response.
4. L-arginine for use in a method of treating cancer and/or infection in a subject.
5. L-arginine for use in a method of adoptive T cell therapy.
6. L-arginine for the use according to any one of the preceding items, wherein said ligand is administered orally to the subject.
7. L-arginine for the use according to any one of the preceding items, wherein L-arginine acts a ligand of BAZ1B/PSIP1 and/or TSN.
8. A ligand of BAZ1B/PSIP1 and/or TSN for use in a method of modulating a T cell mediated immune response in a subject.
9. The ligand for the use according to item 8, wherein in said method of modulating a T cell mediated immune response the T cell mediated immune response is enhanced.
10. The ligand for the use according to item 8 or 9, wherein said T-cell mediated immune response is a T cell mediated anti-cancer response or a T cell mediated anti-infection response.
11. A ligand of BAZ1B/PSIP1 and/or TSN for use in a method of treating cancer and/or infection in a subject.
12. A ligand of BAZ1B/PSIP1 and/or TSN for use in a method of adoptive T cell therapy.
13. The ligand for the use according to any one of claims 8 to 12, wherein said ligand is L-arginine.
14. An in vitro method of identifying a BAZ1B/PSIP1 and/or TSN ligand which is capable of modulating a T-cell mediated immune response, comprising: i) cultivating a T cell population in a suitable cell culture medium the presence of IL-2 and a candidate ligand ii) removing IL-2 and said candidate ligand from the cell culture medium iii) determining the level of T cell survival in the presence of the candidate ligand as compared to an untreated control.
15. The method according to item 14, further comprising in step (i) activating the T cells by contacting the T cells with an anti-CD3 antibody and/or an anti-CD28 antibody and/or an MHC-I or MHC-II bound antigen optionally presented by an antigen-presenting cell.
16. A nucleic acid molecule comprising at least one polynucleotide sequence encoding
    (1) a BAZ1B polypeptide comprising or consisting of the sequence depicted in SEQ ID NO: 1 or an isoform or functional variant thereof, and/or
    (2) a PSIP1 polypeptide comprising or consisting of the sequence depicted in SEQ ID NO: 2 or an isoform or a functional variant thereof, and/or
    (3) a TSN polypeptide comprising or consisting of the sequence depicted in SEQ ID NO: 3 or an isoform or a functional variant thereof.
17. The nucleic acid molecule according to item 16, comprising
    (1) a polynucleotide sequence comprising or consisting of the sequence depicted in SEQ ID NO: 4 or a functional variant thereof, and/or (2) a polynucleotide sequence comprising or consisting of the sequence depicted in SEQ ID NO: 5 or a functional variant thereof, and/or (3) a polynucleotide sequence comprising or consisting of the sequence depicted in SEQ ID NO: 6 or a functional variant thereof;

and optionally at least one regulatory element operably linked to any one or each of (1) to (3).

18. The nucleic acid molecule according to any one of items 16 to 17, wherein said nucleic acid molecule is selected from a single or double-stranded DNA or RNA, a DNA:RNA hybrid molecule or combinations thereof.

19. A vector comprising the nucleic acid molecule according to any one of items 16 to 18.

20. The vector according to item 19, wherein said vector is an expression vector.

21. The vector according to item 20 or 21, wherein said vector is selected from a non-viral vector including plasmid DNA, plasmid mini-circles, transposons, cosmids and artificial chromosomes or a viral vector including retroviruses, herpes viruses, lentiviruses, adenoviruses and adeno-associated viruses.

22. The nucleic acid molecule according to any one of items 16 to 18 or the vector according to any one of items 19 to 21 for use in a method of gene therapy in a subject in need thereof.

23. The nucleic acid molecule or the vector for the use according to item 22, wherein the gene therapy method comprises the step of (a) introducing said nucleic acid molecule or vector into a host cell in vivo; or (b) introducing said nucleic acid molecule or vector into a host cell ex vivo and re-introducing the host cell into the subject.

24. The nucleic acid molecule according to any one of items 16 to 18 or the vector according to any one of items 19 to 21 for use in a method of modulating a T cell mediated response in a subject.

25. The nucleic acid molecule according to any one of items 16 to 18 or the vector according to any one of items 19 to 21 for use in a method of treating cancer and/or infection in a subject.

26. An in vitro method of introducing the nucleic acid molecule according to any one of items 16 to 18 and/or the vector according to any one of items 19 to 12 into a host cell.

27. A host cell comprising a nucleic acid molecule according to any one of items 16 to 18 and/or vector according to any one of items 19 to 21. 28. The host cell according to item 27, wherein said T cell expresses an increased amount of BAZ1B, PSIP1 and/or TSN.

29. The host cell according to item 28, wherein said host cell is a T cell.

30. The host T cell according to item 29, wherein said T cell is selected from a naïve, effector, or memory CD8+ cytotoxic T cell, a naïve, effector, or memory CD4+ helper T cell, a natural killer T cell (NKT), a regulatory T cell (Treg) or a gamma delta T cell.

31. The host T cell according to item 29 or 30, wherein said T cell further comprises a (optionally recombinant) T cell receptor (TCR) or a chimeric antigen receptor (CAR) recognizing an antigen presented on neoplastic cells or infected cells.

32. The host cell or host T cell according to item 27 or 31 for use in a method of adoptive cell therapy (ACT).

33. The host cell or host T cell according to item 27 or 31 for use in a method of modulating a T cell mediated immune response in a subject.

34. The host cell or host T cell according to item 27 or 31 for use in a method of treating cancer or infection in a subject.

35. A pharmaceutical composition comprising (i) L-arginine; and/or (ii) a BAZ1B, PSIP1 and/or TSN ligand, and/or (iii) the nucleic acid molecule according to any one of items 16 to 18 and/or (iv) a vector according to any one of items 19 to 21, and/or (v) a host cell according to any one of items 27 to 31, and optionally at least one pharmaceutically acceptable excipient.

36. An in vitro method of contacting an (isolated) T cell with L-arginine or a BAZ1B, PSIP1 and/or TSN ligand.

37. The in vitro method according to item 36, wherein said method is an in vitro cultivation method and comprises contacting an (isolated) T cell with L-arginine or a BAZ1B, PSIP1 and/or TSN ligand in a suitable cell culture medium.

38. The method according to item 36 or 37, wherein said BAZ1B, PSIP1 and/or TSN ligand is L-arginine.

39. The method according to any one of items 36 to 38 wherein L-arginine or said ligand is added to the cell culture medium in an amount sufficient to promote survival of said (isolated) T cell.

40. The method according to any one of items 36 to 39 wherein said method further comprises genetically modifying the T cells.

41. The method according to item 40, wherein modification of the T cells comprises (a) introducing a vector encoding an recombinant T cell receptor (TCR) or a chimeric antigen receptor (CAR) and/or (b) introduction of a vector according to any one of items 19 to 21 into the T cells.

42. A method of modulating a T cell mediated immune response in a subject comprising administering (i) L-arginine and/or a BAZ1B, PSIP1 and/or TSN ligand and/or (ii) a nucleic acid molecule according to any one of items 16 to 18 and/or (iii) a vector according to any one of items 19 to 21 and/or (iv) a host cell according to any one of items 27 to 31 to the subject.

43. A method of treating cancer and/or infection in a subject comprising administering (i) L-arginine and/or a BAZ1B, PSIP1 and/or TSN ligand and/or (ii) a nucleic acid molecule according to any one of items 16 to 18 and/or (iii) a vector according to any one of items 19 to 21 and/or (iv) a host cell according to any one of items 27 to 31 to the subject.

FIGURES

FIG. 1. Metabolic and proteomic profiling reveals distinct changes in L-arginine metabolism in activated human T cells. (A) Schematic view of the experimental approach. (B) Comparison of protein abundances between 72 h-activated (CD3+CD28 antibodies) and freshly isolated non-activated human naïve CD4+ T cells. Closed circles indicate proteins that changed significantly (FDR=0.05, $S_0$=1). Dark grey dots are enzymes of the arginine and proline metabolism that changed significantly. (C) Comparison of metabolite abundances in 72 h-activated and freshly isolated non-activated human naïve CD4+ T cells. Closed circles indicate metabolites that changed significantly (|Log 2 fc|>1, p<0.01). Grey dots are metabolites of the arginine and proline metabolism that changed significantly. Similar changes were observed when 72 h-activated CD4+ T cells were compared with naïve CD4+ T cells cultured overnight in the absence of TCR stimulation.

FIG. 2. L-arginine is rapidly metabolized upon activation (A) Intracellular abundance of L-arginine in non-activated (non-act) and activated naïve CD4+ T cells (CD3+CD28 antibodies). Boxplot, n=30 from three donors, each in a different color; a.u. arbitrary units. (B) Kinetics of $^3$H-L-arginine uptake during a 15 min pulse. Box plot, n=5 from three donors. (C) Uptake, proteome incorporation and intracellular abundance of the indicated amino acids. Barplot (left): $5\times10^4$ cells were activated for 4 days and consumption of amino acids from medium was analyzed. Essential amino acids are in grey; n=4 from four donors, error bars represent s.e.m. Barplot (center): Proteome incorporation of amino acids estimated from the copy numbers of each protein. Heat map (right): Intracellular amino acid abundance relative to naive T cells over time as determined by MS; n=30 from three donors. Leucine and isoleucine could not be distinguished as they have the same mass. (D) Changes in the abundance of metabolites and proteins of the arginine and proline metabolism between non-activated and 72 h-activated CD4+ T cells. Log 2 fold changes of proteins and metabolites are color-coded. Significant changes are in bold (FDR=0.05, $S_0$=1 for proteins; and p<0.05 (two-tailed unpaired Student's t-test), |Log 2 fc|>1 for metabolites). Black dots are metabolites that were not detected by MS. Only enzymes that were detected by MS are shown. (E) Metabolic tracing of L-arginine. 96 h-activated T cells were pulsed with $^{13}C_6$-L-arginine and the metabolic fate was analyzed by LC-MS/MS at different time points. AFL, Apparent fractional labeling; n=4 from two donors. $^{13}$C Citrulline was not detected.

FIG. 3. L-arginine globally influences metabolism of activated human T cells. (A) Human naïve CD4+ T cells were activated in control medium (Ctrl) or in medium supplemented with 3 mM L-arginine (L-Arg) or 3 mM L-ornithine (L-Orn) and harvested at different time points. The heat map shows the difference between the abundance of metabolites in T cells cultured in L-Arg or L-Orn-medium and controls. Shown are only metabolites with a Log 2 fc>1 and an adjusted p value of <0.05; n=12 from two donors. Log 2 fold change between 0 and >+2 for L-Orn and L-Arg exemplarily indicated as "high". (B) Differential analysis of the glycolytic pathway between naïve CD4+ T cells cultured in L-Arg medium or Ctrl medium, 96 h after activation. Log 2 fold changes of proteins and metabolites are color-coded. Proteins or metabolites whose abundance changed significantly are in bold (for proteins FDR=0.005, $S_0$=5, |Log 2 fc|>1, and for metabolites p<0.05 (Student's t-test), |Log 2 fc|>1). 3-P-Glycerate and 2-P-Glycerate could not be distinguished as they have the same mass. (C) 72 h-activated T cells were plated in fresh medium and glucose consumption was determined enzymatically after 24 h; n=9 from three donors. (D) Seahorse experiment performed with activated (96 h) T cells from one donor. Oligomycin was injected after 56 min, FCCP after 96 min, and antimycin (to inhibit the respiratory chain) after 136 min. Data are representative of 5 independent experiments with different donors. (E,F) Relative oxygen consumption rate (OCR) (E) and relative spare respiratory capacity (SRC) (F) of activated (96 h) T cells; n=12 from three donors. ****p<0.0001 (Student's t-test).

FIG. 4. L-arginine limits human T cell differentiation and endows cells with a high survival capacity in vitro. (A, B) Human naïve CD4+ T cells were activated in L-Arg medium or Ctrl medium in the presence of 10 ng/ml IL-12. IFN-γ was quantified in culture supernatants after 5 days (A) or after re-activation for 5 h with PMA/Ionomycin (B); n=9 from three donors. (C) Naïve CD4+ T cells were labeled with CellTrace Violet (CTV) and activated in L-Arg medium or Ctrl medium. On day 10, proliferating $CTV^{lo}$ T cells were stained with an antibody to CCR7 and analyzed by flow cytometry; n=15 from three donors. (D) Naïve CD4+ T cells were activated for 5 days in L-Arg or Ctrl medium in the presence of exogenous IL-2, washed extensively and cultured in Ctrl medium in the absence of IL-2. Shown is the percentage of living T cells as determined by Annexin V staining at different time points after IL-2 withdrawal. One representative experiment out of three performed. (E) Same experiment as in (D). Shown is the difference of living activated CD4+ and CD8+ T cells 5 days after withdrawal of IL-2; n=46, from sixteen donors (CD4+ T cells); n=13, from four donors (CD8+ T cells). (F) Difference of living activated CD4+ T cells 5 days after IL-2 withdrawal. Naïve CD4+ T cells were activated and L-Arg (3 mM) was added to the culture medium at the indicated time points; n=12 from four donors. (G) Difference of living activated CD4+ T cells 5 days after IL-2 withdrawal. Naïve CD4+ T cells were activated in Ctrl medium or medium supplemented with the indicated metabolites (3 mM, except for spermidine 0.1 mM). Ctrl, n=21; D-Arg, n=9; L-lysine, n=18; L-Arg-HCl, n=10; L-Arg+L-Lys, n=12; L-Orn, n=20; L-Cit, L-Pro, n=12; urea, creatine, agmatine, n=6; putrescine, n=18; spermidine, n=8, from at least three donors. (H) Difference of living activated CD4+ T cells 5 days after IL-2 withdrawal. Naïve CD4+ T cells were activated in the presence or absence of nitric oxide synthase inhibitors Dimethylarginine (DiMeArg) or L-NG-Nitroarginine methyl ester (L-NAME), both used at 1 mM. Ctrl and L-Arg, n=26; DiMeArg and L-NAME, n=16; DiMeArg+L-Arg and L-NAME+L-Arg, n=12, from at least three donors. (I) Difference of living activated CD4+ T cells 5 days after IL-2 withdrawal. Naïve CD4+ T cells were activated in absence (Ctrl) or presence of the arginase inhibitors N$^\omega$-Hydroxy-nor-L-arginine (nor-NOHA, 300 μM) and S-(2-boronoethyl)-L-cysteine (BEC, 300 μM); n=21, from seven donors. 0) Same as in (I) but cultures were performed in medium containing 150 μM L-arginine. (K) Effect of norNOHA and BEC on proliferation of CTV-labeled naïve T cells measured 72 h after activation. *p<0.05, p<0.01, *p<0.001, ****p<0.0001 (Student's t-test).

Figure 5:
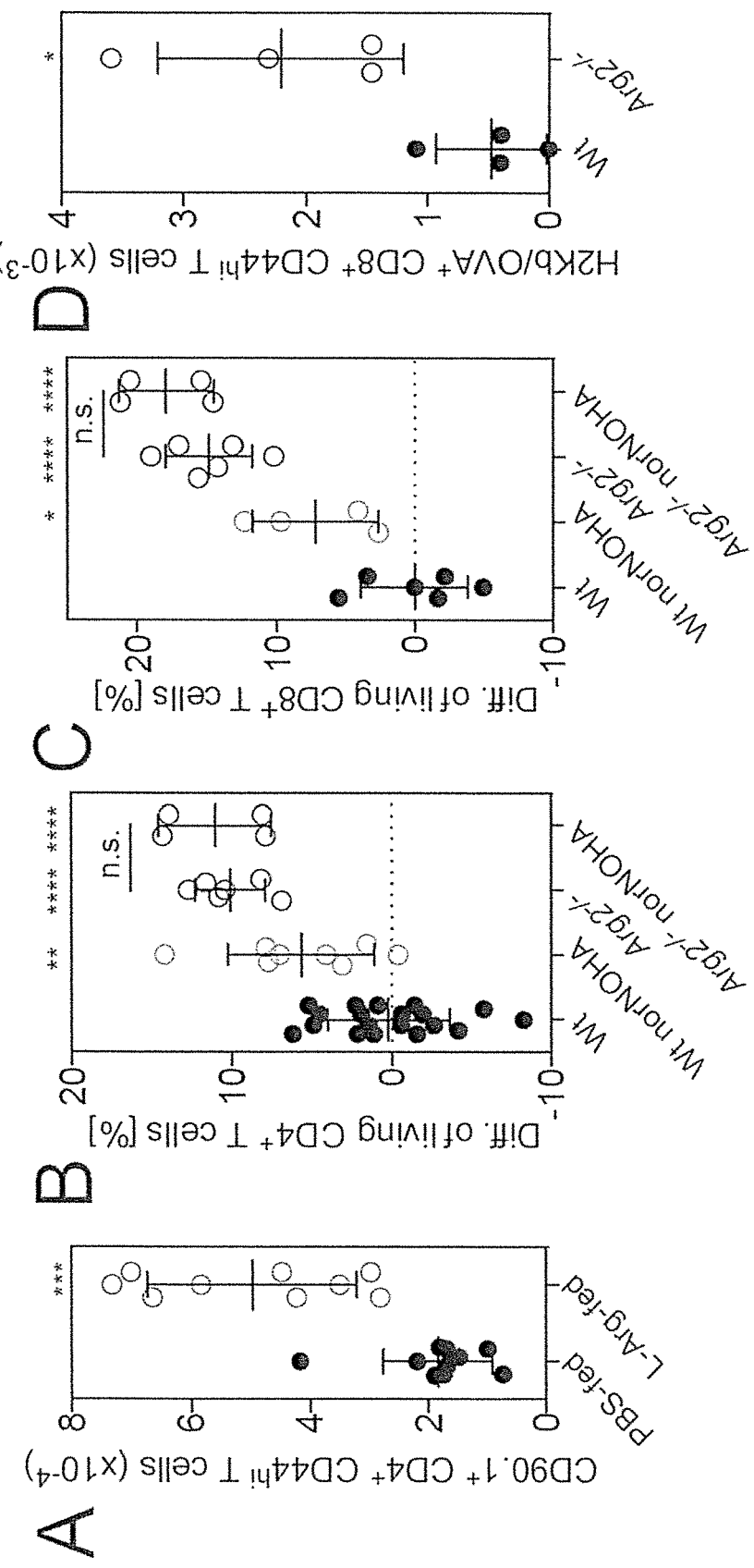

FIG. 5. Increased intracellular L-arginine levels endow mouse T cells with a high survival capacity in vitro and in vivo. (A) BALB/c CD90.1+ CD4+ TCR transgenic T cells specific for the influenza HA110-119 peptide were adoptively transferred into CD90.2+ host mice that were then immunized subcutaneously (s.c.) with HA110-119 in Complete Freund's Adjuvant (CFA). Mice were fed with L-arginine-HCl (1.5 mg/g body weight) or PBS, administrated daily starting 1 day before immunization. Fifteen days later, the amount of CD44hi CD90.1+ CD4+ TCR transgenic T cells in draining lymph nodes was measured by FACS analysis; n=9 from two independent experiments. (B, C) In vitro T cell survival experiment with C56BL/6 wild type (Wt) or Arg2−/− T cells. Naïve CD62Lhi CD44lo CD4+ T cells and CD8+ T cells were activated for 4 days in L-Arg or Ctrl medium in the absence or presence of the arginase inhibitor norNOHA (500 μM). On day 2 exogenous IL-2 was added to the cultures, on clay 4 cells were washed extensively and cultured in medium without IL-2. Shown is the percentage of living CD4+ (B) and CD8+ (C) T cells as determined by Annexin V staining 2 clays after IL-2 withdrawal. Wt, n=6-19; Wt norNOHA, n=6-8; Arg2−/−, n=4-6; Arg2−/− norNOHA, n=4. (D) Equal numbers of CD45.1+Wt and CD45.2+CD90.2+ Arg2−/− naïve CD8+ T cells were transferred into CD45.2+CD90.1+ host mice. Mice were immunized with the OVA257-264 peptide in CFA. 15 days after immunization, the amount of OVA257-264-specific CD44hi CD8+ T cells was measured in draining lymph nodes by flow cytometry using OVA257-264/H-2 Kb multimers; n=4. One representative experiment out of two performed. *p<0.05,  p<0.01, *p<0.001, **** p<0.0001 (Student's t-test).

FIG. 6. BAZ1B, PSIP1 and TSN mediate the L-arginine-dependent reprogramming of T cells towards increased survival capacity. (A) Scheme of the limited proteolysis workflow. (B) Proteins that experience a structural change in response to 1 mM L-arginine but not to 1 mM D-arginine or L-ornithine. Transcriptional regulators are in grey, proteins are grouped according to their functions. Known interactions are indicated based on string-db.org/and genemania.org/. (C) Survival experiment with human CD4+ T cell clones devoid of the indicated proteins. Control (Ctrl), n=39; Cas9-transduced control (Cas9 Ctrl), n=45; BAZ1B-KO, PSIP1-KO, and PTPN6-KO, n=46, n=9, and n=29, respectively. Each T cell clone was analyzed in triplicate. Bars represent the mean±s.e.m. (D) Same as in (C). Cas9 Ctrl, n=20; TSN-KO and B2M-KO, n=23 and n=3, respectively. (E) Percentage of living cells after IL-2 withdrawal of T cells cultured in Ctrl medium. Ctrl, n=39; Cas9 Ctrl, n=45; BAZ1B-KO, PSIP1-KO, and TSN-KO, n=46, n=9, and n=29, respectively. (F-I) Western blots or FACS analysis of T cell clones showing deletion of target proteins. C refers to Cas9 Ctrl clones. Unspecific bands are marked with asterisk. An antibody to tubulin (Tub) was used as a loading control. B2M-KO was verified by staining cells with an antibody against MHC-I. *p<0.05, p<0.01, *p<0.001, *****p<0.0001 (Student's t-test). See also FIG. S6.

FIG. 7. CD8+ T cells with increased L-arginine levels display improved anti-tumor activity in vivo. (A) Survival of activated mouse CD8+OT-I T cells (4 d) after IL-2 withdrawal. Data points represent the difference between the percentage of living T cells from cultures performed in L-Arg medium or Ctrl medium; n=11. (B) CD90.1+CD45.1/ 2+ and CD90.1+CD45.1+ naïve CD8+ OT-I T cells were activated for 4 days in Ctrl medium or L-Arg medium, respectively. Equal numbers of the congenically marked activated OT-I cells were co-transferred into Cd3e-/- mouse and the number of living T cells was measured in pooled spleen and lymph nodes at the indicated time points; n=3 at each time point. (C) Naïve CD8+ OT-I T cells were activated with CD3+CD28 antibodies in L-Arg medium or control (Ctrl) medium. Five days after activation, the percentage of Tcm-like cells (CD44hi, CD62L+) was measured by flow cytometry; n=15. (D) Naïve OT-I CD8+ T cells were activated in L-Arg medium or Ctrl medium and IFN-γ was quantified in culture supernatants after 5 days; n=15. (E) Same as in (D) but T cells were re-activated on day 5 day with PMA/Ionomycin; n=15. (F, G) B16.OVA melanoma cells were injected into C57BL/6 mice and tumors were allowed to grow for 10 days. Naïve OT-I CD8+ T cells were activated in vitro in L-Arg medium or Ctrl medium and injected into tumor bearing mice. Tumor burden (F) and survival (G) were assessed over time. Data are representative of three independent experiments, each performed with 7-9 mice per group. (H) B16.OVA melanoma cells were injected into C57BL/6 mice and tumors were allowed to grow for 6 clays. At day 6, naïve CD8+ OT-I T cells were transferred into tumor bearing mice and at day 7 mice were immunized with OVA peptide. Starting one day before the T cell transfer, PBS or L-arginine (1.5 mg/g body weight) was orally administered daily; n=19 from three independent experiments. Bars represent the s.e.m. *p<0.05, p<0.01, *p<0.001, ****p<0.0001 (Student's t-test). In (G) *p<0.05 as determined by log-rank test comparison between curves.

FIG. 8. Quality control of the proteome dataset, Related to FIG. 1. (A) Sorting of human naïve CD4+ T cells. Shown are FACS plots of cells after enrichment with anti-CD4 magnetic beads. Cells were sorted as CD4+ CCR7+ CD45RA+ and CD8–CD25–. (B) Expression kinetics of indicated marker proteins. Bars represent the s.e.m. of data from different donors, n=7 (for resting cells), n=3 (for 12 h, 72 h), n=2 (for 96 h, 48 h), n=1 (for 24 h). CD25 and CD8 were not identified in resting cells. After activation, expression of CD25 increased whereas CD8 was never detected. (C) Identified protein groups per condition. Taking all conditions together, a total of 9,718 proteins were identified. Per condition two numbers are indicated; the higher number indicates the total identifications and the lower number the mean of the single shots. Samples in grey were measured on a different instrument than samples in black. L-arg refers to 3 mM L-arginine. (D) Relative protein abundance over time shown as a heat map. Log 2 fold changes (FC) are relative to naïve resting T cells. All Log 2 fold changes between 0 and <–6 indicated as "low". The marker for proliferating cells Ki-67 increased abruptly after 48 h, when cells started to proliferate. CD40L expression increased immediately after activation and then decreased to initial levels. A similar expression pattern was observed for CD69, which inhibits egress from lymph nodes (Shiow et al., 2006). The expression of integrins α4 and β7 increased at later time points. (E) Copy numbers of individual subunits of well-characterized protein complexes were plotted against each other. As the Sec23 subfamily includes Sec23A and Sec23B, their copy numbers were added up. The same was done for the subfamily members of Sec24 (A-D). (F) Copy numbers of components of the nuclear pore complex (NPC). The stoichiometry of subunits measured using targeted quantitative proteomics (Ori et al., 2013) is indicated on the graph in red. Shown are copy numbers measured in naïve resting T cells from seven donors. (G) Same as in (F) but shown are copy numbers measured from activated cells (72 h). n=3 from three donors. Note that the numbers of Nup107 increased from 11,464±1620 to 53,091±1471.

FIG. 9. Impact of L-citrulline on metabolism, Related to FIG. 3. (A) Human naïve CD4$^+$ T cells were activated in normal medium or in L-Arg medium. Nitric oxide formation was measured using DAF-FM diacetate at different time points. (B) T cells were activated in control medium (Ctrl, containing 1 mM L-arginine), or in medium supplemented with 3 mM L-arginine (L-Arg) or 3 mM L-citrulline (L-Cit) and harvested at different time points. The heat map shows the difference in the abundance of metabolites in T cells cultured in L-Arg- or L-Cit-medium compared to controls. Shown are only metabolites with a log 2 fold change >1 and an adjusted p value of <0.05. n=6 from one donor. Log 2 fold change between 0 and >+2 for L-Orn, L-Arg and L-Cit exemplarily indicated as "high".

Figure 10:
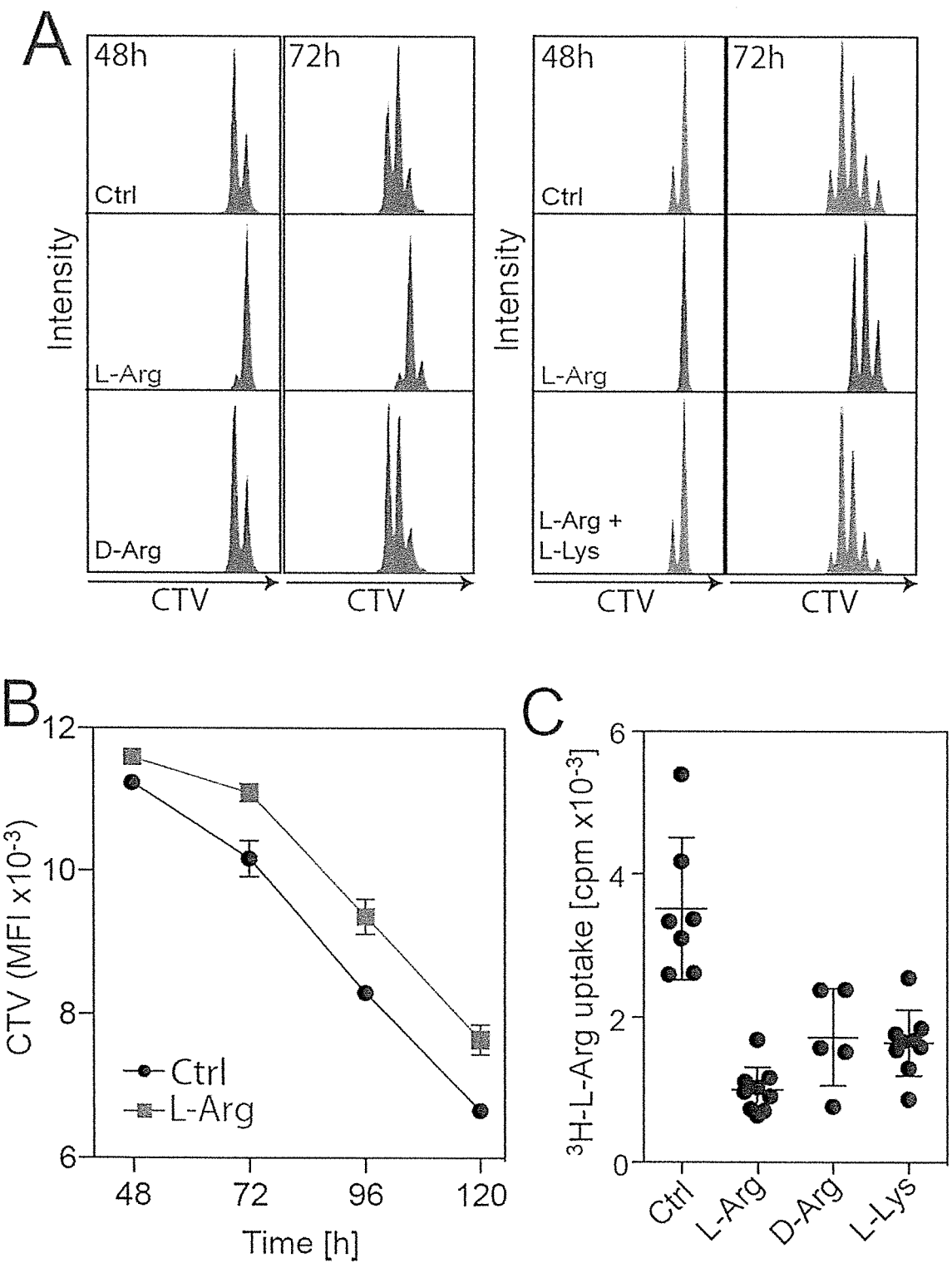

FIG. 10. Effect of L-arginine on the onset of proliferation, Related to FIG. 4. (A) Kinetics of T cell proliferation. Human naïve CD4+ T cells were labeled with CellTrace-Violet (CTV) and activated in Ctrl medium or in L-Arg medium or in medium supplemented with 3 mM D-arginine or 3 mM L-arginine together with 3 mM L-lysine. Cell divisions were monitored at 48 h and 72 h by flow cytometry. (B) CTV-labeled CD4+ T cells were activated in normal medium or L-Arg medium and the dilution of CTV was measured over time by flow cytometry. n=5 from two donors. (C) 3H-L-arginine uptake by 3 day-activated CD4+

T cells during a 15 minutes pulse. Where indicated, 3 mM L-arginine, D-arginine or L-lysine was added to the culture medium as a competitive uptake inhibitor. n=7 for control, n=9 for L-Arg, n=5 for D-Arg, and n=9 for L-Lys. Bars represent the s.e.m.

FIG. 11. L-arginine increases the survival of activated T cells independent of mTOR signaling, Related to FIG. 4. (A) Human naïve CD4$^+$ T cells were activated for 4 days, lysed and the phosphorylation levels of S6K1 (pThr389) and 4E-BP (pThr37/46) were analyzed by Western blot. Rapamycin inhibited the phosphorylation of the mTOR targets, while DMSO or supplementation of the culture medium with 3 mM L-arginine had no effect. T cells hardly proliferated upon activation in culture medium containing no or 20 µM L-lysine and therefore phosphorylation of the target proteins could not be assessed. (B) T cell survival experiment. Human naïve CD4$^+$ T cells were activated in Ctrl medium or in medium containing 100 nM rapamycin. On day 5, cells were washed to withdraw IL-2 and cell survival was measured at different time points (day 5). (C) Same as in (B) but cell survival was only measured 5 days after IL-2 withdrawal. n=7 from seven donors. (D) Metabolic profiling of CD4$^+$ T cells activated in medium containing 100 nM rapamycin. The heat map shows the difference of metabolite abundances between rapamycin-treated cells and controls. n=10 from two donors. Log 2 fold change between 0 and >+2 exemplarily indicated as "high" for rapamycin.

Figure 12:
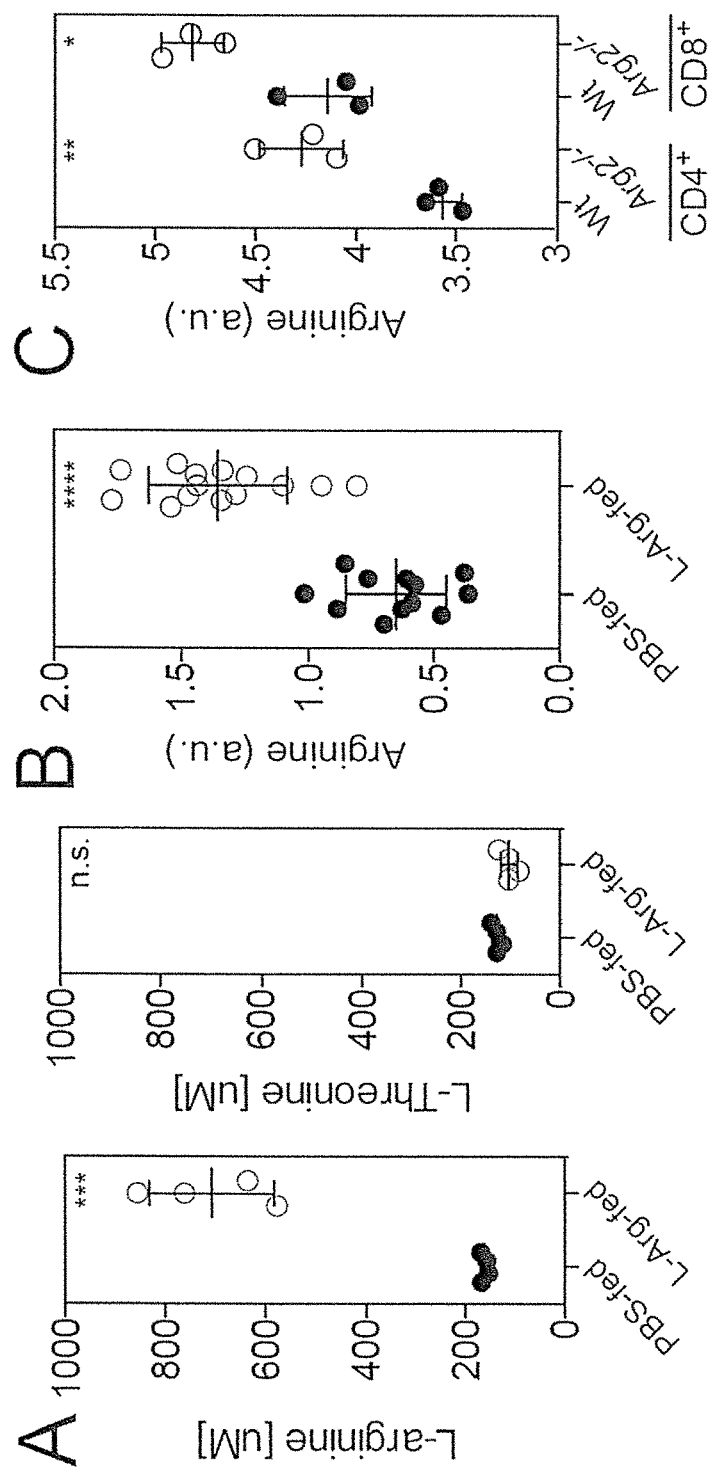

FIG. 12. Oral administration of L-arginine increases L-arginine levels in mouse sera and T cells, Related to FIG. 5. (A) BALB/c mice were administered L-arginine (1.5 mg/g body weight) and sera were collected after 30 minutes. L-arginine and, as a control, L-threonine concentrations were analyzed on a MassTrak amino acid analyzer. n=4. (B) BALB/c mice were immunized with ovalbumin in CFA. Sixty hours later, activated T cells from draining lymph nodes were enriched using magnetic beads coated with antibodies to CD44. Metabolites were extracted using hot 70% ethanol and L-arginine and L-glutamine levels (as an internal standard) were measured using LC-MS/MS. Shown is the ratio between L-arginine and L-glutamine intensities. n=14. (C) Intracellular L-arginine levels of wild type and Arg2$^{-/-}$ CD4$^+$ and CD8$^+$ T cells 4 days after activation. n=3. For statistical tests, a two-tailed unpaired Student's t-test was used throughout, n.s. non significant; *p<0.05; p<0.005; *p<0.0005; ****p<0.0001.

Figure 13:
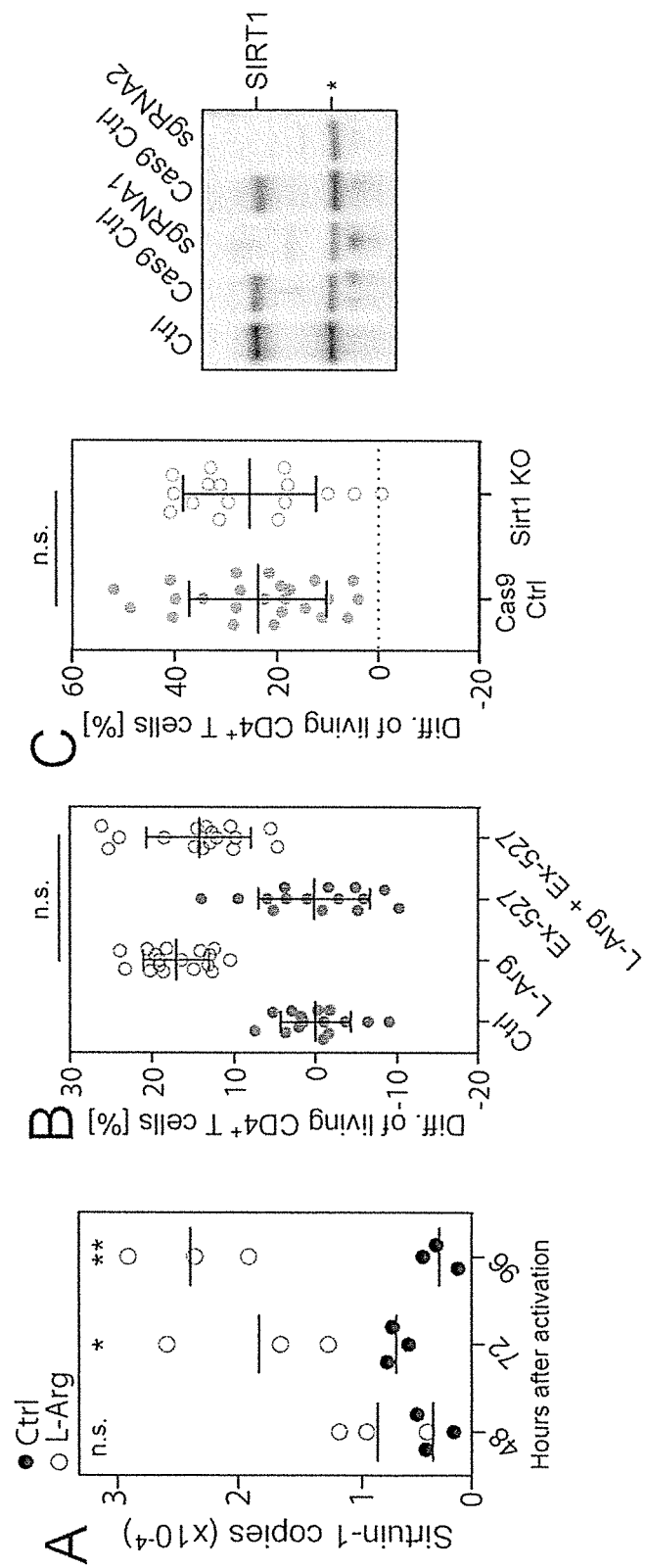

FIG. 13. L-arginine up-regulates Sirtuin-1, Related to FIG. 6. (A) Copy numbers of Sirtuin-1 (SIRT1) as determined by quantitative MS in human naïve CD4$^+$ T cells activated in normal medium or L-Arg-medium. n=3 from three donors. (B) T cell survival experiment. The Sirtuin-1 inhibitor Ex-527 was added at the time point of activation at a concentration of 5 µM. n=16 from four donors. (C) T cell survival experiments with clones expressing Cas9 only, or clones devoid of Sirtuin-1. n=16 from 6 clones. Right panel: Western blot of two different Sirtuin-1 knockout clones generated with different sgRNAs. * unspecific band. For statistical tests, a two-tailed unpaired Student's t-test was used throughout, n.s. non significant; * p<0.05;  p<0.005; * p<0.0005; **** p<0.0001.

EXAMPLES

In the following, particular examples illustrating various embodiments and aspects of the invention are presented. However, the present invention shall not to be limited in scope by the specific embodiments described herein. The following preparations and examples are given to enable those skilled in the art to more clearly understand and to practice the present invention. The present invention, however, is not limited in scope by the exemplified embodiments, which are intended as illustrations of single aspects of the invention only, and methods which are functionally equivalent are within the scope of the invention. Indeed, various modifications of the invention in addition to those described herein will become readily apparent to those skilled in the art from the foregoing description, accompanying figures and the examples below. All such modifications fall within the scope of the appended claims.

Using proteomics, metabolomics and functional approaches the inventors have shown that increased L-arginine levels can exert pleiotropic effects on T cell activation, differentiation and function, ranging from increased bioenergetics and survival to in vivo anti-tumor activity.

The inventors found that activated T cells heavily consume L-arginine and rapidly convert it into downstream metabolites, which lead to a marked decrease in intracellular levels after activation. Addition of exogenous L-arginine to the culture medium increased intracellular levels of free L-arginine and of several other metabolites, and induced a metabolic switch from glycolysis to OXPHOS, thus counteracting the Warburg effect (Vander Heiden et al., 2009). While the mechanism by which L-arginine induces the broad metabolic changes remains elusive, a possible explanation for the switch towards OXPHOS is that increased L-arginine levels up-regulate the serine biosynthesis pathway, which has been shown to fuel the TCA cycle and consequently OXPHOS (Possemato et al., 2011). Suggestive evidence for a link between L-arginine and the functionality of mitochondria has been provided by earlier observations; L-arginine improves mitochondrial function and reduces apoptosis of bronchial epithelial cells after injury induced by allergic airway inflammation (Mabalirajan et al., 2010), and had a beneficial effect for the treatment of patients with a mitochondrial disorder (Koga et al., 2010).

A striking finding is that a two-fold increase in intracellular L-arginine concentrations induces human and mouse T cells to acquire a Tcm-like phenotype with high expression of CCR7 and CD62L and a decreased production of IFN-γ. This may be a consequence of decreased glycolysis induced by L-arginine, as previous studies demonstrated that glycolytic activity supports IFN-γ translation (Chang et al., 2013). Although the inventors observed a delayed onset of cell proliferation, L-arginine-treated T cells progressed through cell division in a way comparable to controls and readily proliferated and differentiated to effector cells upon secondary stimulation. Furthermore, inhibition of arginases in human T cells or deletion of ARG2 in mouse T cells did not affect cell proliferation, suggesting that the downstream fate of L-arginine is less important in T cells than the levels of free L-arginine. L-arginine may induce some of its pleiotropic effects through interfering with arginine methyltransferases, which can affect the functions of various proteins (Geoghegan et al., 2015).

Improved T cell survival is another striking effect induced by elevated intracellular L-arginine levels. Having excluded a role for L-arginine-derived nitric oxide and for the metabolic regulator Sirtuin-1 that has been shown to increase lifespan of lower eukaryotes and reduce glycolytic activity (Rodgers et al., 2005), which in T cells may enhance memory T cell formation and anti-tumor responses (Sukumar et al., 2013), the inventors considered a direct effect of L-arginine on protein functions. Metabolite-protein interactions are more frequent than previously appreciated (Li et al., 2010) and in some cases such interactions may have functional consequences. For instance, cholesterol binds to about 250 proteins (Hulce et al., 2013) and succinate, an intermediate of the TCA cycle, stabilizes HIF-1α in macrophages, leading to increased secretion of IL-1β (Tannahill et al., 2013). The inventors took advantage of a novel method that allows proteome-wide probing of metabolite-protein interactions without modifying metabolites (Feng et al., 2014) and identified several proteins that changed their structure in the presence of L-arginine, which were likely sensors required to mediate the metabolic and functional response. The inventors provide evidence that three nuclear proteins (BAZ1B, PSIP1, and TSN) were required in T cells for mediating L-arginine's effect on survival. BAZ1B is a transcriptional regulator containing a PHD domain that supposedly binds to methylated histones. PSIP1 is a transcriptional co-activator implicated in protection from apoptosis (Ganapathy et al., 2003). Interestingly, the structural changes induced by L-arginine affect the PHD domain of BAZ1B and the AT-hook DNA-binding domain of PSIP1, which may affect DNA binding and lead to the induction of the pro-survival program. Finally, TSN, a small DNA and RNA binding protein, has been implicated in DNA repair, regulation of mRNA expression and RNA interference (Jaendling and McFarlane, 2010) and can thus influence the cellular phenotype in various ways. The conclusion that these three proteins are involved in the pro-survival effect mediated by L-arginine is based on the analysis of several different knock out T cell clones. Yet, there was variability in the response to L-arginine, which may suggest compensatory mechanisms. This would be consistent with the finding that several independent proteins can sense L-arginine and contribute to the improved survival capacity. Future studies are needed to clarify the mechanism of how L-arginine affects the structure and functions of the identified sensors in vivo and how this translates into increased survival.

While the inventors addressed the response to elevated L-arginine levels, it is well established that T cells also sense L-arginine depletion, as it may occur in tumor microenvironments or when myeloid suppressor cells degrade L-arginine through ARG1 (Bronte and Zanovello, 2005). The inventors have shown that moderately reduced uptake of L-arginine has a negative impact on T cell survival without affecting proliferation. However, when L-arginine was completely depleted from the culture medium, T cells no longer proliferated (data not shown and Rodriguez et al., 2007). Lack of L-arginine in T cells can be sensed by GCN2, leading to an amino acid starvation response (Rodriguez et al., 2007) and by SLC38A9, leading to inhibition of mTOR (Rebsamen et al., 2015; Wang et al., 2015), which in turn inhibits T cell growth and proliferation.

The present findings that T cells with increased L-arginine levels display improved anti-tumor activity may be due to a combination of phenotypic changes, including improved survival capacity, metabolic adaptations, and maintenance of a Tcm-like phenotype. L-arginine may also impact on other cell types in vivo, e.g. oral administration of L-arginine to healthy volunteers has been shown to enhance the numbers and activity of natural killer cells (Park et al., 1991). Future work is needed to address the exact mechanism by which L-arginine acts in vivo and favors memory T cell formation and anti-tumor responses.

Generally, metabolite levels can be influenced without genetic manipulations, offering the possibility for therapeutic applications. The beneficial effect of L-arginine on T cell survival and anti-tumor functionality may be exploited therapeutically, for instance to improve adoptive T cell therapies. Additionally, the dataset on the dynamics of the proteome and metabolome during the T cell response constitute a framework for future studies addressing the complex interplay between metabolism and cellular functions.

Example 1: Global Proteomic and Metabolomic Changes Following Activation of Human Naïve $CD4^+$ T Cells To investigate the metabolic adaptations underlying T cell activation, the inventors analyzed the cellular proteome and metabolome of human primary naïve T cells using high-resolution mass spectrometry. Naïve $CD45RA^+$ $CCR7^+$ $CD4^+$ T cells were sorted up to >98% purity from blood of healthy donors (FIG. 8A) and either analyzed immediately after sorting or at different time points following activation with antibodies to CD3 and CD28. After cell lysis, proteins were digested and analyzed by liquid chromatography-coupled mass spectrometry (LC-MS) (Meissner and Mann, 2014; Nagaraj et al., 2011). In parallel, polar metabolites were extracted from cells at each time point and analyzed by non-targeted flow-injection metabolomics, a semi-quantitative method that allowed us a rapid and deep profiling of metabolites, with the limitations that isobaric compounds cannot be discriminated and of possible in-source degradation (Fuhrer et al., 2011) (FIG. 1A). For a detailed description of the applied materials and methods, reference is made to Ex. 9 and in particular to Ex. 9.5-9.10.

The inventors identified a total of 9,718 proteins, quantified the abundance of 7,816 at each time point, and estimated their absolute copy numbers. Expression profiles of characteristic T cell proteins were in agreement with the literature and copy numbers of proteins that form stable complexes were in correct ratios (FIG. 8B-8G). Non-targeted metabolomics led to the identification of 429 distinct ion species, which were putatively mapped to human metabolites.

A comparative analysis of the proteome and metabolome of 72 h-activated and non-activated naïve T cells identified 2,824 proteins whose relative expression changed significantly (Welch-test, FDR=0.05, $S_0=1$), reflecting the fundamental morphological and functional alterations that T cells undergo upon activation (FIG. 16). Up-regulated proteins were enriched in enzymes of several metabolic pathways, including nucleotide synthesis, folate-mediated one-carbon metabolism, as well as arginine and proline metabolism. Out of 429 metabolites, 49 increased significantly (Log 2 fold change (fc)>1; P<0.01), but only 14 were less abundant in activated T cells, of which three, arginine, ornithine and N-acetylornithine, belonged to the same metabolic pathway (FIG. 1C).

Collectively, these data provide a comprehensive resource on the dynamics occurring in the proteome and metabolome of activated human primary naïve $CD4^+$ T cells.

Example 2: Intracellular L-Arginine is Rapidly Metabolized in Activated T Cells

Based on the data obtained, the inventors inspected the changes in the arginine metabolism more closely.

The decrease in intracellular arginine occurred abruptly between 24 and 48 hours after T cell activation (FIG. 2A). This finding was surprising in view of the high concentration of L-arginine in the medium (1 mM) and of the high uptake rate of $^3$H-L-arginine (Ex. 9.12) in activated T cells, which exceeded the requirement for protein synthesis by more than two-fold (FIGS. 2C and 2B).

To gain insights into the metabolic fate of L-arginine, the inventors analyzed the activation-induced changes in metabolites and proteins of the surrounding metabolic network (FIG. 2D). For a detailed description of the applied materials and methods, reference is made to Ex. 9 and in particular to Ex. 9.5-9.7 and 9.12.

While metabolites around the urea cycle were decreased, the arginine transporter cationic amino acid transporter 1 (CAT-1) and the enzymes arginase 2 (ARG2), ornithine aminotransferase (OAT) and spermidine synthase (SRM), which are required for the conversion of L-arginine into ornithine, L-proline and spermidine, respectively, were up-regulated. These findings suggest that L-arginine was rapidly converted into downstream metabolites. Indeed, $^{13}$C-L-arginine tracing experiments showed an immediate and strong accumulation of $^{13}$C in ornithine, putrescine, agmatine and, to a lower extent, in spermidine and proline (FIG. 2E). Addition of the arginase inhibitor norNOHA did not affect the conversion of L-arginine into agmatine, but markedly reduced the conversion into ornithine, putrescine, spermidine and proline (FIG. 2E). This indicated that in T cells L-arginine is mainly catabolized through arginase, likely through mitochondrial ARG2, since the cytosolic enzyme arginase 1 (ARG1) was undetectable in T cells.

Collectively, these data show that L-arginine is avidly taken up by activated T cells in amounts exceeding the requirements for protein synthesis and can be rapidly converted by metabolic enzymes into downstream metabolites.

Example 3: Elevated L-Arginine Levels Regulate Several Metabolic Pathways

Because activated T cells showed a drop in their intracellular arginine concentration—while all other amino acids either remained steady or increased—the inventors assessed the consequences of increasing L-arginine availability on metabolism.

The inventors first performed a kinetic metabolome analysis of naïve T cells activated in standard medium (containing 1 mM L-arginine) or in medium in which the concentration of L-arginine was increased 4-fold. Intracellular arginine and ornithine levels were increased 1.5-2.5-fold at all time points in T cells activated in L-arginine-supplemented medium as compared to controls (FIG. 3A), while nitric oxide, which is generated from L-arginine by nitric oxide synthase (NOS), did not increase (FIG. 9A). Notably, at late time points after activation (72 h-120 h), several other metabolites, including intermediates of the urea cycle, nucleotides, sugar derivatives, and amino acids, were increased (FIG. 3A). In contrast, an increased availability of L-arginine's downstream metabolites L-ornithine or L-citrulline (added to the culture medium at the same concentration as L-arginine) only had minor effects on metabolism (FIGS. 3A and 9B).

These findings suggest that L-arginine directly regulates several metabolic pathways in activated T cells.

A proteome analysis showed that the expression of 202 out of 7,243 proteins was significantly different in T cells activated in L-arginine-supplemented medium, indicating that T cells were reprogrammed under the influence of increased intracellular L-arginine levels.

In particular, PC, PCK2 and FBP1, which promote gluconeogenesis, were increased, while glucose transporters and glycolytic enzymes were decreased (FIG. 3B). Indeed, these T cells consumed less glucose (FIG. 3C), indicating that the glycolytic flux was diminished by L-arginine supplementation. Moreover, the serine biosynthesis pathway that branches from glycolysis, as well as several intermediates of the mitochondrial tricarboxylic acid (TCA) cycle, were up-regulated (FIG. 3B).

Consistent with the fact that the TCA cycle fuels OXPHOS, L-arginine supplementation increased oxygen consumption 1.7 fold, and augmented the mitochondrial spare respiratory capacity (SRC) (FIG. 3D-3F). Oxygen consumption was measured as described in Ex. 9.13. Collectively, these data demonstrate that an increase in intracellular L-arginine levels skewed the metabolism in activated T cells from glycolysis towards mitochondrial OXPHOS.

Example 4: L-Arginine Influences Human T Cell Proliferation, Differentiation and Survival Naïve T cells start to divide after an initial period of growth that lasts 24-40 hours. Subsequently, they divide rapidly and differentiate into effector T cells that produce inflammatory cytokines, such as IFN-gamma, and into memory T cells that survive through homeostatic mechanisms (Schluns and Lefrancois, 2003; Surh et al., 2006).

The inventors therefore asked whether elevated intracellular L-arginine concentrations affect the fate of activated T cells. For a detailed description of the applied materials and methods, reference is made to Ex. 9 and in particular to Ex. 9.14-9.16.

Naïve CD4$^+$ T cells activated in L-arginine-supplemented medium showed a slightly delayed onset of proliferation, but once proliferation started, doubling rates were comparable to controls (FIGS. 10A and 10B). The onset of proliferation was not affected by D-arginine or by addition of L-lysine (a competitive inhibitor of L-arginine uptake, FIG. 10A) to L-arginine-supplemented cultures (FIG. 10C). Cell proliferation was determined as described in Ex. 9.16.

Importantly, T cells activated in L-arginine-supplemented medium secreted much less IFN-gamma than T cells cultured in control medium (FIG. 4A). However, when these cells were re-activated, they were able to secrete IFN-gamma in comparable amounts (FIG. 4B), indicating that T cells primed in the presence of high L-arginine concentrations retained the capacity to differentiate into Th1 effector cells upon secondary stimulation. Since low production of cytokines is characteristic of CCR7$^+$ lymph node-homing Tcm cells (Sallusto et al., 1999), the inventors analyzed the expression of CCR7 on day 10 after activation and found a higher fraction of proliferating CCR7$^+$ T cells in L-arginine supplemented cultures than in control cultures (FIG. 4C). Cytokine release was determined as described in Ex. 9.15.

Collectively, these data indicate that increased intracellular L-arginine levels limit T cell differentiation and maintain cells in a Tcm-like state.

To test whether L-arginine affects T cell survival, the inventors activated human naïve CD4$^+$ and CD8$^+$ T cells, expanded them in the presence of IL-2 or IL-15 and measured their viability upon cytokine withdrawal (Ex. 9.14).

Strikingly, L-arginine supplementation significantly increased the survival of activated CD4$^+$ and CD8$^+$ T cells when cultured in the absence of exogenous cytokines (FIGS. 4D and 4E). L-arginine was most effective when added during the first 48 hours following T cell activation (FIG. 4F). Conversely, L-lysine or D-arginine, which both inhibit L-arginine uptake (FIG. 10C), decreased T cell survival significantly (FIG. 4G), indicating that reduced availability of intracellular L-arginine negatively affects T cell survival.

L-arginine's downstream metabolites ornithine, citrulline, proline, urea, and creatine, as well as nitric oxide, had no effect, while agmatine, putrescine or spermidine decreased T cell survival (FIGS. 4G and 4H). L-arginine-HCl enhanced T cell survival to a similar extent than free base L-arginine, ruling out a possible influence of pH. The increased T cell survival induced by elevated intracellular L-arginine concentration was independent of mTOR signaling (Araki et al., 2009), based on the finding that L-arginine supplementation did not change phosphorylation levels of two targets of mTOR (p70 S6K1 and 4E-BP) and inhibition of mTOR by rapamycin, although enhancing T cell survival, affected metabolism in an entirely different way than L-arginine (FIG. 11A-11D).

To further support the notion that L-arginine regulates T cell survival, the inventors inhibited arginase (that converts L-arginine into L-ornithine) with norNOHA or BEC, which increase intracellular L-arginine levels (Monticelli et al., 2016).

Inhibition of arginase significantly increased the survival capacity of activated CD4$^+$ T cells, even in medium containing physiological levels of L-arginine (150 µM) (FIGS. 4I and 4J). Inhibition of arginase did not affect proliferation (FIG. 4K), indicating that polyamines can be synthesized from other sources than L-arginine, i.e. from L-glutamate (Wang et al., 2011), a finding that is consistent with the experiments showing that polyamine synthesis only partially depends on L-arginine (FIG. 2E).

Collectively, these data indicate that elevated intracellular L-arginine levels directly induced metabolic changes and longevity of human CD4$^+$ and CD8$^+$ T cells, independently of mTOR signaling or downstream metabolites.

Example 5: L-Arginine Influences Mouse T Cell Survival In Vivo

To address the impact of changes in intracellular L-arginine levels in vivo, the inventors performed experiments in mice.

Naïve TCR transgenic CD4$^+$ T cells specific for a hemagglutinin peptide (HA$_{110-119}$) were adoptively transferred into BALB/c mice that received daily supplements of L-arginine (1.5 mg/g body weight) or PBS as a control. This amount of arginine doubled the daily dietary intake present in chow. Mice were immunized with HA$_{110-119}$ in CFA and the amount of transgenic T cells in draining lymph nodes was measured 15 days later. Three times more CD44$^{hi}$ CD4$^+$ TCR transgenic T cells were recovered in mice fed with L-arginine compared to control mice (Ex. 9.24, FIG. 5A). In control experiments, the inventors found that 30 minutes after oral administration, L-arginine levels in the serum increased from about 160 µM to 700 µM (FIG. S5A) and intracellular L-arginine levels of CD44$^{hi}$ activated T cells increased approximately two fold (FIG. 12B). For a detailed description of the applied materials and methods, reference is made to Ex. 9 and in particular to Ex. 9.24.

The inventors then analyzed CD4$^+$ and CD8$^+$ T cells from Arg2-deficient mice (Ex. 9.23). For a detailed description of the applied materials and methods, reference is made to Ex. 9 and in particular to Ex. 9.23.

When compared to wild type T cells, Arg2$^{-/-}$ T cells showed 20% higher baseline intracellular L-arginine levels (FIG. 5C) and when stimulated in vitro with antibodies to CD3 and CD28, they survived significantly longer than wild type T cells after IL-2 withdrawal (FIGS. 5B and 5C). Moreover, activation in the presence of the arginase inhibitor norNOHA, while increasing the survival of wild type T cells, did not affect survival of Arg2$^{-/-}$ T cells (FIGS. 5B and 5C), indicating that in mouse T cells L-arginine degradation occurred mainly by ARG2. Finally, equal numbers of congenically marked wild type and Arg2$^{-/-}$ CD8$^+$ T cells were co-transferred into wild type mice that were immunized with the ovalbumin-peptide SIINFEKL (OVA$_{257-264}$) in CFA. Fifteen days after immunization, the number of Kb-restricted OVA$_{257-264}$-specific CD44$^{hi}$ CD8$^+$ T cells was measured in lymph nodes using multimer staining. As shown in FIG. 5D, OVA-specific Arg2$^{-/-}$ T cells were more numerous than OVA-specific wild type T cells. Taken together, these findings provide evidence that the intracellular L-arginine concentration, which can be elevated by dietary supplementation, can increase the survival capacity of antigen-activated T cells in vivo.

Example 6: Global Analysis of Structural Changes Identifies Putative L-Arginine Sensors To elucidate the mechanism by which L-arginine promotes T cell survival, the inventors first examined the list of differentially expressed proteins and found among the top hits Sirtuin-1, a histone deacetylase, which is known to increase the lifespan of different organisms (Tissenbaum and Guarente, 2001).

However, a role for Sirtuin-1 was excluded based on the findings that human naïve T cells activated in the presence of the Sirtuin-1 inhibitor Ex-527 and Sirtuin-1-deficient T cells generated using the CRISPR/Cas9 technology displayed a L-arginine-mediated increase in survival comparable to controls (FIG. 13).

Given that L-arginine directly promotes T cell survival, the inventors set out to identify putative protein interactors that may be modified by binding of L-arginine and initiate the pro-survival program.

Therefore, the inventors probed structural changes across the T cell proteome that occur in response to L-arginine following a recently developed workflow (Feng et al., 2014) (FIG. 6A). T cells were homogenized and incubated in the absence or presence of 1 mM L-arginine, D-arginine or L-ornithine. Subsequently, samples were subjected to limited proteolysis with proteinase K (Ex. 9.11), which preferentially cleaves flexible regions of a protein. After denaturation and trypsin digestion, peptide mixtures were analyzed by LC-MS (Ex. 9.8-9.11). As trypsin cleaves polypeptides specifically after lysine or arginine, cleavages after other amino acids were introduced by proteinase K, leading to half-tryptic peptides. Significant changes in the abundances of half-tryptic peptides (fc>5, p<0.05, >2 peptides per protein) were used as readout for structural changes induced by the addition of metabolites. For a detailed description of the applied materials and methods, reference is made to Ex. 9 and in particular to Ex. 9.8-9.11.

Because L-arginine, but not D-arginine or L-ornithine, promoted T cell survival, the inventors searched for proteins that were exclusively affected by L-arginine and were cleaved by proteinase K at identical sites in all samples from six donors.

Out of 5,856 identified proteins, the inventors found 20 candidates that fulfilled these stringent criteria (FIG. 6B). These proteins differed widely in molecular weight and abundance, excluding a bias towards large or abundant proteins. Most candidates associated with four functional groups: mRNA splicing, DNA repair, regulation of the cytoskeleton, and the ribosome, while seven were transcriptional regulators (in orange in FIG. 6B). Thus, the global approach revealed several proteins with various functions that structurally respond to elevated intracellular L-arginine levels.

Example 7: BAZ1B, PSIP1, and TSN are Required for the L-Arginine-Mediated Effect on T Cell Survival To test whether selected candidates identified through the structural analysis were involved in the L-arginine-mediated survival benefit, the inventors generated gene knockout human T cell clones using the CRISPR/Cas9 system that were screened for loss of the corresponding protein by Western blot or flow cytometry. For a detailed description of the applied materials and methods, reference is made to Ex. 9 and in particular to Ex. 9.18.

Knockout of PTPN6 (Shp-1) or B2M did not alter the effect of L-arginine on T cell survival (FIGS. 6C and 6D), while no viable clones were obtained after knockout of XRCC6, AC/N7 and SSB (not shown). Strikingly, knockout of the transcriptional regulators BAZ1B, PSIP1 and TSN significantly reduced L-arginine's beneficial effect on T cell survival (FIGS. 6C, 6D and 6F-6J). Importantly, when cultured in control medium prior to the IL-2 withdrawal (cf. Ex. 9.16), T cell clones lacking these transcriptional regulators proliferated and survived like controls (FIG. 6E), indicating that their viability was unaffected but they were unable to sense increased L-arginine levels and to induce the pro-survival program. Taken together, these data provide evidence that BAZ1B, PSIP1 and TSN interact with L-arginine and play a role in the reprogramming of T cells towards increased survival capacity.

Example 8: L-Arginine Improves Anti-Tumor T Cell Response In Vivo

Since L-arginine increased the survival capacity of human and mouse T cells and favors the formation of Tcm-like cells that have been shown to be superior than effector memory T cells (Tem) in eradicating tumors in mouse models (Klebanoff et al., 2005), the inventors reasoned that increased intracellular L-arginine levels might positively affect anti-tumor T cell responses in vivo.

The inventors stimulated naïve TCR transgenic $CD8^+$ OT-I T cells specific for the $OVA_{257-264}$ peptide in control or L-arginine-supplemented medium for 4 days and measured their survival in vitro following IL-2 withdrawal and in vivo after adoptive transfer into lymphogenic $Cd3e^{-/-}$ mice. For a detailed description of the applied materials and methods, reference is made to Ex. 9 and in particular to Ex. 9.19-9.22.

Consistent with the previous data, L-arginine endowed OT-I T cells with a higher survival capacity both in vitro and in vivo (FIGS. 7A and 7B). Moreover, these T cells maintained a Tcm-like state and secreted less IFN-γ than controls after in vitro priming but upon reactivation, they produced even more IFN-γ than controls (FIG. 7C-E). Remarkably, when adoptively transferred into wild type mice bearing B16 melanoma tumors expressing the OVA antigen, L-arginine-treated OT-I T cells mounted a superior anti-tumor response, as measured by the reduction of tumor size and by the increased survival of mice (FIGS. 7F and 7G). Naïve OT-I T cells primed in vivo by OVA+CFA immunization of tumor-bearing mice that were fed with L-arginine were also superior in mediating an anti-tumor response compared to OT-I T cells primed in mice fed with PBS (FIG. 7H). Collectively, these data demonstrate that elevated L-arginine levels increased the survival capacity of $CD8^+$ T cells and their anti-tumor activity in vivo.

Example 9: Experimental Model and Subject Details

Example 9.1 Human Primary T Cells

Blood from healthy donors was obtained from the Swiss Blood Donation Center of Basel and Lugano, and used in compliance with the Federal Office of Public Health

Example 9.2: Mice

Wild type (Wt) C57BL/6J and BALB/c mice were obtained from Harlan (Italy). $Cd3e^{-/-}$ C57BL/6 mice, which lack all T cells but exhibit organized lymphoid organ structures and normal B cell development, have been described previously (Malissen et al., 1995). OT-I (JAX 003831) mice were bred and maintained on a $Rag1^{-/-}$ (JAX 002216) background. Wt C57BL/6 mice with different CD45 and CD90 alleles were bred in the inventors' facility, and crossed with $Rag1^{-/-}$ OT-I transgenic mice, to perform adoptive transfer experiments. $Arg2^{-/-}$ C57BL/6 (JAX 020286) mice were kindly provided by W. Reith. Hemagglutinin (HA) TCR-transgenic (6.5) BALB/c mice (Kirberg et al., 1994) specific for peptide 111-119 from influenza HA were kindly provided by J. Kirberg and bred in the inventor's facility. All mice were bred and maintained under specific pathogen-free conditions. Animals were treated in accordance with guidelines of the Swiss Federal Veterinary Office and experiments were approved by the Dipartimento della Sanità e Socialità of Canton Ticino.

Example 9.3: Isolation of Human T Cells

Peripheral blood mononuclear cells (PBMCs) were isolated by Ficoll gradient centrifugation. $CD4^+$ T cells were enriched with magnetic microbeads (Miltenyi Biotec). Naïve $CD4^+$ T cells were sorted as $CD4^+$ $CCR7^+$ $CD45RA^+$ $CD25^-$ $CD8^-$ on a FACS Aria III cell sorter (BD Biosciences). For cell staining, the following antibodies were used: anti-CD4-APC (allophycocyanin), clone 13B8.2; anti-CD8-APC, clone B9.11; anti-CD8-FITC (fluorescein isothiocyanate), clone B9.11; anti-CD4-FITC, clone 13B8.2; anti-CD45RA-PE (phycoerythrin), clone alb11; anti-CD25-FITC, clone B1.49.9 (all from Beckman Coulter); anti-CCR7-Brilliant Violet 421, clone G043H7 (Biolegend).

Example 9.4: Cell Culture

Cells were cultured in RPMI-1640 medium supplemented with 2 mM glutamine, 1% (v/v) non-essential amino acids, 1% (v/v) sodium pyruvate, penicillin (50 U $ml^{-1}$), streptomycin (50 μg $ml^{-1}$; all from Invitrogen), and 5% (v/v) human serum (Swiss Blood Center). Human T cells were activated with plate bound anti-CD3 (5 μg/ml, clone TR66) and anti-CD28 (1 μg/ml, clone CD28.2, BD Biosciences) for 48 h. Then, cells were cultured in IL-2 containing media (500 U/ml).

Example 9.5: Metabolomics

Naïve $CD4^+$ T cells were either analyzed directly after isolation or at different time points after activation with CD3 and CD28 antibodies. Cells were washed twice in 96-well plates with 75 mM ammonium carbonate at pH 7.4 and snap frozen in liquid nitrogen. Metabolites were extracted three times with hot (>70° C.) 70% ethanol. Extracts were analyzed by flow injection—time of flight mass spectrometry on an Agilent 6550 QTOF instrument operated in the negative mode, as described previously (Fuhrer et al., 2011). Typically 5,000-12,000 ions with distinct mass-to-charge (m/z) ratio could be identified in each batch of samples. Ions were putatively annotated by matching their measured mass to that of the compounds listed by the KEGG database for *Homo sapiens*, allowing a tolerance of 0.001 Da. Only deprotonated ions (without adducts) were considered in the analysis. In case of multiple matching, such as in the case of structural isomers, all candidates were retained.

Example 9.6 Metabolic Flux Experiments

Naïve CD4+ T cells were activated and 4 days, later extensively washed and pulsed with L-arginine free RPMI medium containing 1 mM [U-$^{13}$C]-L-Arginine hydrochloride (Sigma). After increasing pulse-times, cells were washed and snap frozen in liquid nitrogen. Metabolites were extracted and analyzed by HILIC LC-MS/MS.

Example 9.7: Detection of Amino Acids and Polyamines by HILIC LC-MS/MS

Supernatants from extraction were dried at 0.12 mbar to complete dryness in a rotational vacuum concentrator setup (Christ, Osterode am Harz, Germany) and dried metabolite extracts were stored at −80° C. Dry metabolite extracts were resuspended in 100 µl water and 5 µl were injected on an Agilent HILIC Plus RRHD column (100×2.1 mm×1.8 µm; Agilent, Santa Clara, Calif., USA). A gradient of mobile phase A (10 mM ammonium formate and 0.1% formic acid) and mobile phase B (acetonitrile with 0.1% formic acid) was used as described previously (Link et al., 2015). Flow rate was held constant at 400 µl/min and metabolites were detected on a 5500 QTRAP triple quadrupole mass spectrometer in positive MRM scan mode (SCIEX, Framingham, Mass., USA).

Example 9.8: Sample Preparation for Proteome MS Analysis

Samples were processed as described by (Hornburg et al., 2014). In brief, cell pellets were washed with PBS and lysed in 4% SDS, 10 mM HEPES (pH 8), 10 mM DTT. Cell pellets were heat-treated at 95° C. for 10 min and sonicated at 4° C. for 15 min (level 5, Bioruptor, Diagenode). Alkylation was performed in the dark for 30 min by adding 55 mM iodoacetamide (IAA). Proteins were precipitated overnight with acetone at −20° C. and resuspended the next day in 8 M Urea, 10 mM Hepes (pH 8). A two-step proteolytic digestion was performed. First, samples were digested at room temperature (RT) with LysC (1:50, w/w) for 3 h. Then, they were diluted 1:5 with 50 mM ammoniumbicarbonate (pH 8) and digested with trypsin (1:50, w/w) at RT overnight. The resulting peptide mixtures were acidified and loaded on C18 StageTips (Rappsilber et al., 2007). Peptides were eluted with 80% acetonitrile (ACN), dried using a SpeedVac centrifuge (Eppendorf, Concentrator plus, 5305 000.304), and resuspended in 2% ACN, 0.1% trifluoroacetic acid (TFA), and 0.5% acetic acid. For deeper proteome analysis a peptide library was built. For this, peptides from naive and activated T cells were separated according to their isoelectric point on dried gel strips with an immobilized pH gradient (SERVA IPG BlueStrips, 3-10/11 cm) into 12 fractions as described by Hubner et al., 2008 (Hubner et al., 2008).

Example 9.9: LC-MS/MS for Analysis of Proteome

Peptides were separated on an EASY-nLC 1000 HPLC system (Thermo Fisher Scientific, Odense, Denmark) coupled online to a Q Exactive mass spectrometer via a nanoelectrospray source (Thermo Fisher Scientific) (Michalski et al., 2011). Peptides were loaded in buffer A (0.5% formic acid) on in house packed columns (75 µm inner diameter, 50 cm length, and 1.9 µm C18 particles from Dr. Maisch GmbH, Germany). Peptides were eluted with a non-linear 270 min gradient of 5-60% buffer B (80% ACN, 0.5% acetic acid) at a flow rate of 250 nl/min and a column temperature of 50° C. Operational parameters were real-time monitored by the SprayQC software (Scheltema and Mann, 2012). The Q Exactive was operated in a data dependent mode with a survey scan range of 300-1750 m/z and a resolution of 70,000 at m/z 200. Up to 5 most abundant isotope patterns with a charge ≥2 were isolated with a 2.2 Th wide isolation window and subjected to higher-energy C-trap dissociation (HCD) fragmentation at a normalized collision energy of 25 (Olsen et al., 2007). Fragmentation spectra were acquired with a resolution of 17,500 at m/z 200. Dynamic exclusion of sequenced peptides was set to 45 s to reduce the number of repeated sequences. Thresholds for the ion injection time and ion target values were set to 20 ms and 3E6 for the survey scans and 120 ms and 1E5 for the MS/MS scans, respectively. Data was acquired using the Xcalibur software (Thermo Scientific).

Example 9.10: Analysis of Proteomics Data

MaxQuant software (version 1.3.10.18) was used to analyze MS raw files (Cox and Mann, 2008). MS/MS spectra were searched against the human Uniprot FASTA database (Version May 2013, 88,847 entries) and a common contaminants database (247 entries) by the Andromeda search engine (Cox et al., 2011). Cysteine carbamidomethylation was applied as fixed and N-terminal acetylation and methionine oxidation as variable modification. Enzyme specificity was set to trypsin with a maximum of 2 missed cleavages and a minimum peptide length of 7 amino acids. A false discovery rate (FDR) of 1% was required for peptides and proteins. Peptide identification was performed with an allowed initial precursor mass deviation of up to 7 ppm and an allowed fragment mass deviation of 20 ppm. Nonlinear retention time alignment of all measured samples was performed in MaxQuant. Peptide identifications were matched across different replicates within a time window of 1 min of the aligned retention times. A library for 'match between runs' in MaxQuant was built from additional single shot analysis at various time points as well as from OFF gel fractionated peptides of naïve and memory CD4 T cells. Protein identification required at least 1 razor peptide. A minimum ratio count of 1 was required for valid quantification events via MaxQuant's Label Free Quantification algorithm (MaxLFQ)(Cox and Mann, 2008; Luber et al., 2010). Data were filtered for common contaminants and peptides only identified by side modification were excluded from further analysis. In addition, it was required to have a minimum of two valid quantifications values in at least one group of replicates. Copy numbers were estimated based on the protein mass of cells (Wisniewski et al., 2012). the inventors found the protein mass of a naïve T cell to be 25 pg and of an activated T cell 75 pg.

Example 9.11: Limited Proteolysis and Mass Spectrometry

Naïve CD4+ T cells were washed twice with PBS and homogenized on ice under non-denaturing conditions (20 mM Hepes, 150 mM KCl and 10 mM $MgCl_2$, pH 7.5,) using a tissue grinder (Wheaton, Millville, N.J., NSA). Homogenates were further passed several times through a syringe (0.45×12 mm) on ice. Next, cell debris was removed by centrifugation and protein concentration of supernatants was determined by BCA assay (BCA Protein Assay Kit, Thermo Scientific, Rockford, Ill., USA). L-arginine, D-arginine or L-ornithine was added to homogenates to a final concentration of 1 nmol per µg total protein, and incubated for 5 minutes at room temperature. As a control, samples without added metabolites were processed in parallel. Then, proteinase K from *Tritirachium album* (Sigma) was added at an enzyme to substrate ratio of 1:100, followed by an incubation of 5 minutes at room temperature. The digestion was stopped by boiling the reaction mixture for 3 minutes. Proteins were denatured by adding 10% sodium deoxycholate (DOC) solution (1:1, v/v) to the reaction mixture, followed by a second boiling step of 3 minutes. Disulfide bridges were reduced with 5 mM Tris(2-carboxyethyl)phosphine hydrochloride (Thermo Scientific) at 37° C. for 30 minutes and subsequently free cysteines were alkylated with 40 mM IAA at 25° C. for 30 minutes in the dark. DOC concentration of the mixture was diluted to 1% with 0.1 M ammonium bicarbonate (AmBiC) prior to a stepwise protein digestion with LysC (1:100, w/w) for 4 hours at 37° C. and trypsin (1:100, w/w) overnight at 37° C. The resulting peptide mixture was acidified to pH<2, loaded onto Sep-Pak tC18 cartridges (Waters, Milford, Mass., USA), desalted and eluted with 80% acetonitrile. Peptide samples were dried using a vacuum centrifuge and resuspended in 0.1% formic acid for analysis by mass spectrometry.

Peptides were separated using an online EASY-nLC 1000 HPLC system (Thermo Fisher Scientific) operated with a 50 cm long in house packed reversed-phase analytical column (Reprosil Pur C18 Aq, Dr. Maisch, 1.9 µm) (Reprosil Pur C18 Aq, Dr. Maisch, 1.9 µm) before being measured on a Q-Exactive Plus (QE+) mass spectrometer. A linear gradient from 5-25% acetonitrile in 240 min at a flowrate of 300 nl/min was used to elute the peptides from the column. Precursor ion scans were measured at a resolution of 70,000 at 200 m/z and 20 MS/MS spectra were acquired after higher-energy collision induced dissociation (HCD) in the Orbitrap at a resolution of 17,500 at 200 m/z per scan. The ion count threshold was set at 1,00 to trigger MS/MS, with a dynamic exclusion of 25 s. Raw data were searched against the *H. sapiens* Uniprot database using SEQUEST embedded in the Proteome Discoverer software (both Thermo Fisher Scientific). Digestion enzyme was set to trypsin, allowing up to two missed cleavages, one non-tryptic terminus and no cleavages at KP (lysine-proline) and RP (arginine-proline) sites. Precursor and fragment mass tolerance was set at 10 ppm and 0.02 Da, respectively. Carbamidomethylation of cysteines (+57.021 Da) was set as static modification whereas oxidation (+15.995 Da) of methionine was set as dynamic modification. False discovery rate (FDR) was estimated by the Percolator (embedded in Proteome Discoverer) and the filtering threshold was set to 1%.

Label-free quantitation was performed using the Progenesis-Q1 Software (Nonlinear Dynamics, Waters). Raw data files were imported directly into Progenesis for analysis. MS1 feature identification was achieved by importing the filtered search results (as described above) from Proteome Discoverer into Progenesis to map the corresponding peptides based on their m/z and retention times. Annotated peptides were then quantified using the areas under their extracted ion chromatograms. Pairwise comparisons were performed with the untreated (no metabolite added) sample as a reference and peptide fold changes were calculated using three biological replicates per condition where the statistical significance was assessed with a two-tailed heteroscedastic Student's t-Test. A fold change was considered significant with an absolute change >5 and a corresponding p-value <0.05. Only proteins with two or more peptides changing significantly (according to the aforementioned criteria) were taken into consideration.

Example 9.12: Quantitative Amino Acid Uptake and Calculation of Proteome Incorporation 150,000 freshly isolated naïve CD4+ T cells were activated with plate bound CD3 and CD28 antibodies and cultured in the same medium for four days. As a control, medium without cells was co-cultured. Then cell supernatants and control media were analyzed by quantitative amino acid analysis (MassTrak, Waters) at the functional genomics center in Zurich. Amino acid uptake was calculated as the difference between control media and cell supernatants. At the time of the measurement, the inventors counted on average 1 Mio cells. the inventors then calculated how much of each amino acid is incorporated into the proteome of 850,000 cells based on the amino acid sequences and copy numbers of each protein. Average copy numbers from the time point 72 h were used.

Example 9.12: $^3$H-Arginine Uptake Assay

Arginine uptake was measured as previously described for glutamine uptake (Carr et al., 2010). Briefly, resting or activated T cells were resuspended at a concentration of $1.5 \times 10^7$ cells/ml in serum-free RPMI 1640 lacking L-arginine. 50 µl 8% sucrose/20% perchloric acid were layered to the bottom of a 0.5 ml Eppendorf tube and 200 µl 1-bromododecane on top of it (middle layer), followed by 50 µl L-arginine-free medium containing 1.5 mCi L-[2,3,4-$^3$H]-arginine-monohydrochloride (Perkin Elmer). Then, 100 µl cell suspension was added to the top layer and cells were allowed to take up radiolabeled L-arginine for 15 min at room temperature. Cells were then spun through the bromododecane into the acid/sucrose. This stops the reaction and separates cells from unincorporated $^3$H-L-arginine. The bottom layer containing the cells was carefully removed and analyzed by liquid scintillation. As controls cell-free media were used.

Example 9.13: Measurements of Oxygen Consumption Rate (OCR)

Measurements were performed using a Seahorse XF-24 extracellular flux analyzer (Seahorse Bioscience). Naïve CD4+ T cells were sorted and activated with plate-bound CD3 and CD28 antibodies in complete medium or medium supplemented with 3 mM L-arginine. Four days later (in the morning), cells were pooled, carefully count and plated ($7 \times 10^5$ cells/well) in serum-free unbuffered RPMI-1640 medium (Sigma) onto Seahorse cell plates coated with Cell-Tak (BD Bioscience). The serum-free unbuffered medium was not supplemented with L-arginine. Oligomycin (1.4 μM, Sigma), Carbonyl cyanide-4-(trifluoromethoxy) phenylhydrazone (FCCP, 0.6 μM, Sigma) and antimycin (1.4 μM, Sigma) were injected.

Example 9.14: IL-2 Withdrawal Assay and Assessment of Cell Viability

Naïve CD4 T cells were activated with plate-bound CD3 and CD28 antibodies. 48 h after activation IL-2 was added to culture media (500 U ml$^{-1}$). After a further 3 days of culturing, cells were washed, counted and equal cell numbers were plated in medium devoid of IL-2. The withdrawal medium was no longer supplemented with e.g. L-arginine. Cell viability was assessed with annexin V.

Example 9.15: Cytokine Analysis $10^5$ naïve T cells were stimulated with plate bound anti-CD3 (5 μg ml$^{-1}$) and anti-CD28 (1 μg ml$^{-1}$) in the presence of IL-12 (10 ng/ml, R&D Systems) to polarize cells towards a Th1 phenotype. After 48 h, cells were transferred into U-bottom plates and IL-2 (10 ng/ml, R&D Systems) was added. Three days later, supernatants were collected and interferon-γ was quantified using FlowCytomix assays (eBioscience). Samples were analyzed on a BD LSR Fortessa FACS instrument and quantification was performed with the FlowCytomix Pro 3.0 software. For re-stimulation, cells were cultured for 5 h in the presence of 0.2 μM phorbol 12-myristate 13-acetate (PMA) and 1 μg/ml ionomycin (both from Sigma).

Example 9.16: Glucose Consumption Assay

The amount of glucose in media was determined using the Glucose (GO) Assay Kit from Sigma. Consumption was calculated as the difference between glucose content in reference medium (co-incubated medium without cells) and cell supernatants.

Example 9.17: Analysis of Phosphorylation Levels of 4E-BP and S6K1

Naïve CD4$^+$ T cells were activated with plate-bound antibodies to CD3 and CD28. Four days after activation, cells were lysed and analyzed by Western blot with the following antibodies obtained from Cell Signaling Technology. Phospho-p70 S6K(Thr389) #9205; p70 S6 Kinase #9202; Phospho-4E-BP1 (Thr37/46) #2855; 4E-BP1 #9644. Rapamycin (Sigma) was used at 100 nM.

Example 9.18: CRISPR/Cas9-Mediated Gene Disruption

Two to four short guide RNAs (sgRNAs) (Table 1) per gene were designed using the online tool provided by the Zhang laboratory (tools.genome-engineering.org). Oligonucleotide pairs with BsmBI-compatible overhangs were annealed and cloned into the lentiviral vector lentiCRISPR v2 (Addgene plasmid #52961) (Sanjana et al., 2014). For virus production, HEK 293T/17 cells were transfected with lentiCRISPR v2, psPAX2 (Addgene #12260) and pMD2.G (Addgene plasmid #12259) at a 8:4:1 ratio using polyethylenimine and cultured in Dulbecco's modified Eagle medium supplemented with 10% fetal bovine serum (FBS), 1 sodium pyruvate, 1% non-essential amino acids, 1% Kanamycin, 50 Units/ml Penicillin/Streptomycin and 50 μM β-mercaptoethanol. The medium was replaced 12 h after transfection and after a further 48 h virus was harvested from supernatant. Cell debris was removed by centrifugation (10 min at 2000 rpm followed) followed by ultra-centrifugation (2.5 hours at 24,000 rpm) through a sucrose cushion.

Freshly isolated naïve CD4$^+$ T cells were lentivirally transduced and activated with plate-bound CD3 and CD28 antibodies. 48 h after activation IL-2 was added to culture media (500 U/ml$^{-1}$). 6 days after activation, cells were cultured for 2 days in medium supplemented with 1 μg/ml puromycin to select for cells expressing the lentiCRISPR v2 vector. Subsequently, cells were cultured in normal medium followed by additional two days in medium containing puromycin for a second selection step. Then, single cell clones were generated by limiting dilution as described in (Messi et al., 2003).

To screen for clones with disrupted target genes, individual clones were lysed with sample buffer containing 80 mM Tris pH 6.8, 10.5% glycerol, 2% SDS and 0.00004% Bromophenol blue. Lysate of 100,000 cells was separated by SDS-PAGE followed, blotted onto PVDF membranes and analyzed with antibodies to target proteins, Baz1B (Abeam, ab50850), PSIP1 (Bethyl, A300-848A), DDX17 (Abeam, ab180190), PTPN6 (Santa Cruz, sc-287) or TSN (Sigma, HPA059561). As loading control membranes were reprobed with an antibody to beta-tubulin (Sigma, T6074). To screen for clones with disrupted B2M, single cell clones were stained with an antibody to MHC-1 (eBioscience, HLA-ABC-FITC) and analyzed by flow cytometry.

Example 9.19: Isolation and Culturing of Mouse CD8$^+$ T Cells

Naïve CD8$^+$ OT-I cells were isolated from Rag1$^{-/-}$ OT-I transgenic mice. Lymph nodes and spleens were harvested and homogenized using the rubber end of a syringe and cell suspensions were filtered through a fine mesh. Cells were first enriched with anti-CD8 magnetic beads (CD8a, Ly-2 MicroBeads, mouse, Miltenyi Biotec) and then sorted on a FACSAria III Cell Sorter (BD Biosciences) to obtain cells with a CD44$^{lo}$ CD62L$^{hi}$ CD8$^+$ phenotype. OT-I cells (CD90.1$^+$) were cultured for 2 days in αCD3/αCD28 (2 ug/ml) bound to NUNC 96 well MicroWell™ MaxiSorp™ plates, (Sigma-Aldrich M9410) in the presence or absence of 3 mM L-arginine in the culture medium. On clay 2 cells were transferred to U-bottom plates and cultured for 2 additional days in the presence of IL-2 (500 U/ml).

Example 9.20: Adoptive T Cell Transfers and Survival Experiments

CD90.1$^+$ CD45.1/2$^+$ OT-I cells were activated with plate-bound antibodies to CD3 and CD28 in control medium. OT-I cells with a different congenic marker (CD90.1$^+$ CD45.1$^+$) were activated in L-arginine-supplemented medium. At day 4, equal cell numbers were injected into the tail vein of Cd3e$^{-/-}$ host mice. To study the expansion of OT-I effector cells, host mice were sacrificed after 1, 3, 6, and 10 days post transfer and CD90.1$^+$ OT-I T cells from lymphoid organs (spleen and lymph nodes) were enriched with anti-CD90.1 micro beads (Miltenyi Biotec), stained and analysed by FACS. The following monoclonal antibodies were used α-CD8α (53-6.7), α-CD44 (1M7), α-CD62L (MEL-14), α-CD90.1 (OX-7), α-CD90.2 (30-H12), α-CD45.1 (A20), α-CD45.2 (104).

Example 9.21: Tumor Experiments: In Vitro Activation of T Cells

B16-OVA melanoma cells were cultured in RPMI 1640 plus 10% FCS, 1% penicillin/streptomycin and 2 mM glutamine. Before injection into mice, cells were trypsinized and washed twice in PBS. Then, $5\times10^5$ cells were subcutaneously injected in the dorsal region of Wt C57BL/6 mice. Ten days post injection, $5\times10^6$ OT-I cells, that have been activated in vitro as described above, were injected into the tail vein of tumor-bearing mice. The size of tumors was measured in a blinded fashion using calipers.

Example 9.22: Tumor Experiments: In Vivo Priming of T Cells

B16-OVA melanoma cells were cultured and injected into Wt C57BL/6 mice as described above. Five clays post injection, when tumors were very small, mice were γ-irradiated (5 Gy) and 24 hours later they received $4\times10^5$ OT-I cells intravenously (i.v.). The clay after mice were immunized intraperitoneally (i.p.) with SIINFEKL peptide ($OVA_{257-264}$) in Inject Alum Adjuvant (Thermo Fisher Scientific). L-Arg (1.5 g/Kg body weight) or PBS, as control, was daily orally administrated, starting one clay before T cell transfer and until the end of the experiment. The size of tumors was measured in a blinded fashion using calipers.

Example 9.23: Experiments with $Arg2^{-/-}$ Mouse T Cells

For in vitro experiments, $5\times10^4$ FACS-sorted naïve T cells were activated with plate-bound antibodies to CD3 (2 μg/ml) and CD28 (2 μg/ml). Two days after activation, T cells were transferred into U-bottom plates and IL-2 was added to culture media. Four clays after activation, cells were washed extensively and plated in medium devoid of IL-2. Cell viability was measured two days after IL-2 withdrawal by Annexin V staining. For in vivo experiments, $10^6$ FACS-sorted Wt $CD8^+$ naïve T cells ($CD45.1^+$) were transferred together with $10^6$ FACS-sorted $Arg2^{-/-}CD8^+$ naïve T cells ($CD45.2^+$, $CD90.2^x$), into slightly γ-irradiated (3 Gy) Wt mice ($CD45.2^+$, $CD90.1^+$). The day after, host mice were immunized subcutaneously (s.c.) with MHC class-I binding peptide SIINFEKL (Chicken Ovalbumin, OVA, amino acids 257-264, 15 μg/mouse) emulsified in Complete Freund's Adjuvant, CFA. CFA was prepared by adding 4 mg/ml of *M. tuberculosis* H37RA (Difco) to Incomplete Freund's Adjuvant, IFA (BD Biosciences). SIINFEKL peptide ($OVA_{257-264}$) was obtained from Servei de Proteòmica, Pompeu Fabra University, Barcelona, Spain. On day 15 post immunization, mice were euthanized and draining lymph nodes were collected and analyzed by flow cytometry. Cells were counted according to the expression of congenic markers and by gating on live $CD4^{hi}$, H-2 $Kb/OVA_{257-264}$ multimer$^+$, $CD8^+$ cells. The H-2 $Kb/OVA_{257-264}$ multimers were purchased from TCMetrix.

Example 9.24: Mouse Experiments with Dietary L-Arginine $2\times10^5$ $CD90.1^+$ $CD4^+$ HA TCR-transgenic T cells, on a BALB/c background, were adoptively transferred in Wt $CD90.2^4$ BALB/c mice. The day after, host mice were immunized s.c. with influenza $HA_{110-119}$ peptide (purchased from Anaspec) emulsified in CFA. L-Arg (1.5 g/kg body weight) or PBS, as control, was daily orally administrated, starting 1 day before T cell transfer and until the end of the experiment. Draining lymph nodes were analyzed on day 15 post immunization for the presence of transferred transgenic memory $CD44^{hi}$ $CD90.1^+$ $CD4^+$ T cells. Sera were collected 30 min after oral L-arginine administration to mice and L-arginine and L-threonine concentrations in sera were measured on a MassTrak (Waters) instrument at the functional genomics center in Zurich. To determine intracellular L-arginine levels, activated T cells were isolated from draining lymph nodes 60 hours after activation and 30 min after the daily L-arginine administration. Metabolites were extracted with hot 70% ethanol and analyzed by HILIC LC-MS/MS.

Example 9.25: Quantification and Statistical Analysis

Statistical parameters including the exact value of n, the definition of center, dispersion and precision measures (mean±SEM) and statistical significance are reported in the Figures and Figure Legends. Data is judged to be statistically significant when p<0.05 by two-tailed Student's t test. In Figures, asterisks denote statistical significance as calculated by Student's t test (*, p<0.05; , p<0.01; *, p<0.001; ****, p<0.0001). Survival significance in adoptive cell transfer studies was determined by a Log-rank test. Statistical analysis was performed in R or GraphPad PRISM 6.

Example 9.26: Proteome Data

Data analysis was performed using the Perseus software and the R statistical computing environment. Missing values were imputed with a normal distribution of 30% in comparison to the standard deviation of measured values and a 1.8 standard deviation down-shift of the mean to simulate the distribution of low signal values (Hubner et al., 2010). Statistical significance between time points was evaluated by one-way ANOVA for each proteinGroup using a FDR of 0.1% and $S_0$ of 2 ($S_0$ sets a threshold for minimum fold change), unless otherwise noted (Tusher et al., 2001). For pairwise comparison, t-test statistic was applied with a permutation based FDR of 5% and $S_0$ of 1.

Example 9.27: Enrichment Analysis

Univariate test was performed on either all proteins or metabolites by t-test with unequal variance (Welch Test). The resulting P-values were adjusted using the Benjamini-Hochberg procedure. Enrichment analysis was performed as suggested by Subramanian et al. (Subramanian et al., 2005). Both for metabolomics and proteomics data, the inventors applied a permissive filtering with adj. p-value less or equal than 0.1 and absolute log 2(fold-change) larger or equal than 0.5. Enrichment P-values were calculated by the Fisher's exact test for all incremental subsets of filtered features ranked by the p-value. For the 261 pathways defined by KEGG, the lowest P-value was retained as a reflection of the best possible enrichment given by the data independently of hard cut-offs. Eventually, enrichment P-values were corrected for multiple testing by the Benjamini-Hochberg method. In general, enrichments with an adjusted P-value <0.05 were considered significant. Pathway enrichments were calculated independently for proteomics and metabolomics data. For metabolome-based enrichments, structural isomers in pathway were condensed and counted only once to account for the fact that the employed technology cannot distinguish between metabolite with identical molecular weight.

Example 9.28: Data and Software Availability

All software is freely or commercially available and is listed in the Key Resource Table.

TABLE 1 sgRNAs used in this study

| Target | sg | Target sequence | SEQ ID NO |
|---|---|---|---|
| SIRT1 | 1 | TCG TAC AAG TTG TCG GCC AG | 7 |
| SIRT1 | 2 | CAG ATT AGT AGG CGG CTT GA | 8 |
| SIRT1 | 3 | TAC CCA GAA CAT AGA CAC GC | 9 |
| ACIN1 | 1 | GAG TTC TGA GTG GTA ATC GA | 10 |
| ACIN1 | 2 | GGT ACT CGG GTC CGT CCC GA | 11 |
| B2M | 1 | GAG TAG CGC GAG CAC AGC TA | 12 |
| B2M | 2 | CCT GAR TCT TTG GAG TAC GC | 13 |
| BAZ1B | 1 | AGT ATG AAG CCC GCT TGG AA | 14 |
| BAZ1B | 2 | ATT TGG ACG TGC AAG AGT AC | 15 |
| BAZ1B | 3 | AAC GGC TTC ACC AGC GGG AA | 16 |
| BAZ1B | 4 | AAA GGT ACA GTG AGC GCA TT | 17 |
| PTPN6 | 1 | GGT TTC ACC GAG ACC TCA GT | 18 |
| PTPN6 | 2 | GGA CAC CTC GGC CCT TGA GC | 19 |
| PSIP1 | 1 | GGA CAC CTC GGC CCT TGA GC | 20 |
| PSIP1 | 2 | AAA AGA GCC GGA TAA AAA AG | 21 |
| SSB | 1 | TCC TTT AGA AAC TTG TCC CG | 22 |
| SSB | 2 | GGA TGA AGG CTG GGT ACC TT | 23 |
| TSN | 1 | TGA AAT CCT TTC TCC CGA TC | 24 |
| TSN | 2 | AAC CTG TAA TAC TGT TCA GC | 25 |
| XRCC6 | 1 | CTC TGC TTC TTC ATC GCC CT | 26 |
| XRCC6 | 2 | ATC CGT GGC CCA TCA TGT CT | 27 |

REFERENCES

Alves, N. L., Derks, I. A., Berk, E., Spijker, R., van Lier, R. A., and Eldering, E. (2006). The Noxa/Mcl-1 axis regulates susceptibility to apoptosis under glucose limitation in dividing T cells. Immunity 24, 703-716.

Araki, K., Turner, A. P., Shaffer, V. O., Gangappa, S., Keller, S. A., Bachmann, M. F., Larsen, C. P., and Ahmed, R. (2009). mTOR regulates memory CD8 T-cell differentiation. Nature 460, 108-112.

Bensimon, A., Heck, A. J., and Aebersold, R. (2012). Mass spectrometry-based proteomics and network biology. Annu. Rev. Biochem. 81, 379-405.

Blagih, J., Coulombe, F., Vincent, E. E., Dupuy, F., Galicia-Vazquez, G., Yurchenko, E., Raissi, T. C., van der Windt, G. J., Viollet, B., Pearce, E. L., et al. (2015). The energy sensor AMPK regulates T cell metabolic adaptation and effector responses in vivo. Immunity 42, 41-54.

Bronte, V., and Zanovello, P. (2005). Regulation of immune responses by L-arginine metabolism. Nat. Rev. Immunol. 5, 641-654.

Chang, C. H., Curtis, J. D., Maggi, L. B., Jr., Faubert, B., Villarino, A. V., O'Sullivan, D., Huang, S. C., van der Windt, G. J., Blagih, J., Qiu, J., et al. (2013). Posttranscriptional control of T cell effector function by aerobic glycolysis. Cell 153, 1239-1251.

Chang, C. H., Qiu, J., O'Sullivan, D., Buck, M. D., Noguchi, T., Curtis, J. D., Chen, Q., Gindin, M., Gubin, M. M., van der Windt, G. J., et al. (2015). Metabolic Competition in the Tumor Microenvironment Is a Driver of Cancer Progression. Cell 162, 1229-1241.

Cui, G., Staron, M. M., Gray, S. M., Ho, P. C., Amezquita, R. A., Wu, J., and Kaech, S. M. (2015). IL-7-Induced Glycerol Transport and TAG Synthesis Promotes Memory CD8(+) T Cell Longevity. Cell 161, 750-761.

De Rosa, V., Galgani, M., Porcellini, A., Colamatteo, A., Santopaolo, M., Zuchegna, C., Romano, A., De Simone, S., Procaccini, C., La Rocca, C., et al. (2015). Glycolysis controls the induction of human regulatory T cells by modulating the expression of FOXP3 exon 2 splicing variants. Nat. Immunol. 16, 1174-1184.

Feng, Y., De Franceschi, G., Kahraman, A., Soste, M., Melnik, A., Boersema, P. J., de Laureto, P. P., Nikolaev, Y., Oliveira, A. P., and Picotti, P. (2014). Global analysis of protein structural changes in complex proteomes. Nat. Biotechnol. 32, 1036-1044.

Fox, C. J., Hammerman, P. S., and Thompson, C. B. (2005). Fuel feeds function: energy metabolism and the T-cell response. Nat. Rev. Immunol. 5, 844-852.

Fuhrer, T., Heer, D., Begemann, B., and Zamboni, N. (2011). High-throughput, accurate mass metabolome profiling of cellular extracts by flow injection-time-of-flight mass spectrometry. Anal. Chem. 83, 7074-7080.

Ganapathy, V., Daniels, T., and Casiano, C. A. (2003). LEDGF/p75: a novel nuclear autoantigen at the crossroads of cell survival and apoptosis. Autoimmun. Rev. 2, 290-297.

Geoghegan, V., Guo, A., Trudgian, D., Thomas, B., and Acuto, O. (2015). Comprehensive identification of arginine methylation in primary T cells reveals regulatory roles in cell signalling. Nat. Commun. 6, 6758.

Gett, A. V., Sallusto, F., Lanzavecchia, A., and Geginat, J. (2003). T cell fitness determined by signal strength. Nat. Immunol. 4, 355-360.

Grohmann, U., and Bronte, V. (2010). Control of immune response by amino acid metabolism. Immunol. Rev. 236, 243-264.

Ho, P. C., Bihuniak, J. D., Macintyre, A. N., Staron, M., Liu, X., Amezquita, R., Tsui, Y. C., Cui, G., Micevic, G., Perales, J. C., et al. (2015). Phosphoenolpyruvate Is a Metabolic Checkpoint of Anti-tumor T Cell Responses. Cell 762, 1217-1228.

Hulce, J. J., Cognetta, A. B., Niphakis, M. J., Tully, S. E., and Cravatt, B. F. (2013). Proteome-wide mapping of cholesterol-interacting proteins in mammalian cells. Nat. Methods 10, 259-264.

Jaendling, A., and McFarlane, R. J. (2010). Biological roles of translin and translin-associated factor-X: RNA metabolism comes to the fore. Biochem. J. 429, 225-234.

Kaech, S. M., and Cui, W. (2012). Transcriptional control of effector and memory CD8+ T cell differentiation. Nat. Rev. Immunol. 12, 749-761.

Klebanoff, C. A., Gattinoni, L., Torabi-Parizi, P., Kerstann, K., Carclones, A. R., Finkelstein, S. E., Palmer, D. C., Antony, P. A., Hwang, S. T., Rosenberg, S. A., et al. (2005). Central memory self/tumor-reactive CD8+ T cells confer superior antitumor immunity compared with effector memory T cells. Proc. Natl. Acad. Sci. USA 102, 9571-9576.

Li, X., Gianoulis, T. A., Yip, K. Y., Gerstein, M., and Snyder, M. (2010). Extensive in vivo metabolite-protein interactions revealed by large-scale systematic analyses. Cell 143, 639-650.

Maciver, N. J., Jacobs, S. R., Wieman, H. L., Wofford, J. A., Coloff, J. L., and Rathmell, J. C. (2008). Glucose metabolism in lymphocytes is a regulated process with significant effects on immune cell function and survival. J. Leuk. Biol. 84, 949-957.

MacIver, N. J., Michalek, R. D., and Rathmell, J. C. (2013). Metabolic regulation of T lymphocytes. Annu. Rev. Immunol. 31, 259-283.

Meissner, F., and Mann, M. (2014). Quantitative shotgun proteomics: considerations for a high-quality workflow in immunology. Nat. Immunol. 15, 112-117.

Monticelli, L. A., Buck, M. D., Flamar, A. L., Saenz, S. A., Tait Wojno, E. D., Yudanin, N. A., Osborne, L. C., Hepworth, M. R., Tran, S. V., Rodewald, H. R., et al. (2016). Arginase 1 is an innate lymphoid-cell-intrinsic metabolic checkpoint controlling type 2 inflammation. Nat. Immunol. 17, 656-665.

Nagaraj, N., Wisniewski, J. R., Geiger, T., Cox, J., Kircher, M., Kelso, J., Paabo, S., and Mann, M. (2011). Deep proteome and transcriptome mapping of a human cancer cell line. Mol. Syst. Biol. 7, 548.

Park, K. G., Hayes, P. D., Garlick, P. J., Sewell, H., and Eremin, O. (1991). Stimulation of lymphocyte natural cytotoxicity by L-arginine. Lancet 337, 645-646.

Pearce, E. L., Poffenberger, M. C., Chang, C. H., and Jones, R. G. (2013). Fueling immunity: insights into metabolism and lymphocyte function. Science 342, 1242454.

Pearce, E. L., Walsh, M. C., Cejas, P. J., Harms, G. M., Shen, H., Wang, L. S., Jones, R. G., and Choi, Y. (2009). Enhancing CD8 T-cell memory by modulating fatty acid metabolism. Nature 460, 103-107.

Possemato, R., Marks, K. M., Shaul, Y. D., Pacold, M. E., Kim, D., Birsoy, K., Sethumadhavan, S., Woo, H. K., Jang, H. G., Jha, A. K., et al. (2011). Functional genomics reveal that the serine synthesis pathway is essential in breast cancer. Nature 476, 346-350.

Rebsamen, M., Pochini, L., Stasyk, T., de Araujo, M. E., Galluccio, M., Kandasamy, R. K., Snijder, B., Fauster, A., Rudashevskaya, E. L., Bruckner, M., et al. (2015). SLC38A9 is a component of the lysosomal amino acid sensing machinery that controls mTORC1. Nature 519, 477-481.

Rodgers, J. T., Lerin, C., Haas, W., Gygi, S. P., Spiegelman, B. M., and Puigserver, P. (2005). Nutrient control of glucose homeostasis through a complex of PGC-1alpha and SIRT1. Nature 434, 113-118.

Rodriguez, P. C., Quiceno, D. G., and Ochoa, A. C. (2007). L-arginine availability regulates T-lymphocyte cell-cycle progression. Blood 109, 1568-1573.

Rolf, J., Zarrouk, M., Finlay, D. K., Foretz, M., Viollet, B., and Cantrell, D. A. (2013). AMPKalpha1: a glucose sensor that controls CD8 T-cell memory. Eur. J. Immunol. 43, 889-896.

Sallusto, F., Lanzavecchia, A., Araki, K., and Ahmed, R. (2010). From vaccines to memory and back. Immunity 33, 451-463.

Sallusto, F., Lenig, D., Forster, R., Lipp, M., and Lanzavecchia, A. (1999). Two subsets of memory T lymphocytes with distinct homing potentials and effector functions. Nature 407, 708-712.

Savitski, M. M., Reinhard, F. B., Franken, H., Werner, T., Savitski, M. F., Eberhard, D., Martinez Molina, D., Jafari, R., Dovega, R. B., Klaeger, S., et al. (2014). Tracking cancer drugs in living cells by thermal profiling of the proteome. Science 346, 1255784.

Schluns, K. S., and Lefrancois, L. (2003). Cytokine control of memory T-cell development and survival. Nat. Rev. Immunol. 3, 269-279.

Sinclair, L. V., Rolf, J., Emslie, E., Shi, Y. B., Taylor, P. M., and Cantrell, D. A. (2013). Control of amino-acid transport by antigen receptors coordinates the metabolic reprogramming essential for T cell differentiation. Nat. Immunol. 74, 500-508.

Siska, P. J., and Rathmell, J. C. (2015). T cell metabolic fitness in antitumor immunity. Trends Immunol. 36, 257-264.

Surh, C. D., Boyman, O., Purton, J. F., and Sprent, J. (2006). Homeostasis of memory T cells. Immunol. Rev. 277, 154-163.

Tannahill, G. M., Curtis, A. M., Adamik, J., Palsson-McDermott, E. M., McGettrick, A. F., Goel, G., Frezza, C., Bernard, N. J., Kelly, B., Foley, N. H., et al. (2013). Succinate is an inflammatory signal that induces IL-1 beta through HIF-1alpha. Nature 496, 238-242.

Tissenbaum, H. A., and Guarente, L (2001). Increased dosage of a sir-2 gene extends lifespan in $Caenorhabclitis$ $elegans$. Nature 410, 227-230.

van der Windt, G. J., Everts, B., Chang, C. H., Curtis, J. D., Freitas, T. C., Amiel, E., Pearce, E. J., and Pearce, E. L. (2012). Mitochondrial respiratory capacity is a critical regulator of CD8+ T cell memory development. Immunity 36, 68-78.

Wang, R., Dillon, C. P., Shi, L. Z., Milasta, S., Carter, R., Finkelstein, D., McCormick, L. L., Fitzgerald, P., Chi, H., Munger, J., et al. (2011). The transcription factor Myc controls metabolic reprogramming upon T lymphocyte activation. Immunity 35, 871-882.

Wang, R., and Green, D. R. (2012). Metabolic checkpoints in activated T cells. Nat. Immunol. 73, 907-915.

Wang, S., Tsun, Z. Y., Wolfson, R. L., Shen, K., Wyant, G. A., Plovanich, M. E., Yuan, E. D., Jones, T. D., Chantranupong, L., Comb, W., et al. (2015). Metabolism. Lysosomal amino acid transporter SLC38A9 signals arginine sufficiency to mTORC1. Science 347, 188-194.

Zamboni, N., Saghatelian, A., and Patti, G. J. (2015). Defining the metabolome: size, flux, and regulation. Molecular Cell 58, 699-706.

The invention claimed is:

1. A method of treating cancer in a subject in need thereof by adoptive T cell therapy, the method comprising:
   a) contacting a therapeutically effective amount of T cells ex vivo with a therapeutically effective amount of L-arginine or a derivative thereof to form a population of expanded T cells; and
   b) administering a therapeutically effective amount of the population of expanded T cells to the subject.

2. The method according to claim 1, wherein the L-arginine derivative is selected from the group consisting of L-arginine hydrochloride, L-arginine malate, L-arginine methyl ester and L-arginine ethyl ester.

3. The method according to claim 1, wherein the adoptive T cell therapy comprises autologous transfer or allogenic transfer of T cells.

4. The method according to claim 1, wherein the T cells are enriched from peripheral blood mononuclear cells (PBMC) obtained from a serum or plasma sample or from tumor biopsies yielding tumor infiltrating lymphocytes (TILs).

5. The method according to claim 1, wherein the T cells expanded ex vivo are antigen-specific T cells.

6. The method according to claim 1, wherein the adoptive T cell therapy comprises the isolation and expansion of a T cell from a donor which exhibits a desired antigen specificity.

7. The method according to claim 1, further comprising genetically engineering the T cells in order to equip them with recombinant T cell receptors (TCRs) or chimeric antigen receptors (CARs) of a desired antigen specificity.

8. The method according to claim 1, further comprising cultivating the T cells in a cell culture medium.

9. The method according to claim 8, further comprising activating the cultivated T cells.

10. The method according to claim 1, wherein the adoptive T cell therapy further comprises one or more of the following steps:
   (i) screening the T cells for a desired antigen specificity;
   (ii) enriching a particular T cell subset;
   (iii) activating the T cells;
   (iv) genetically engineering the T cells for expression of a recombinant T cell receptor (TCR), chimeric antigen receptor (CAR) or other effector molecule; and/or
   (v) exposing the T cells to cytokines or growth factors in order to promote proliferation, differentiation and/or activation.

* * * * *